(12) United States Patent
Krinke et al.

(10) Patent No.: US 8,906,022 B2
(45) Date of Patent: Dec. 9, 2014

(54) APPARATUS AND METHODS FOR SECURING A BONE IMPLANT

(75) Inventors: Todd A. Krinke, Buffalo, MN (US);
Steve D. Kruse, St. Michael, MN (US);
Kyle Taylor, Brooklyn Park, MN (US);
Stefan J. Hertel, Minneapolis, MN (US); Michael P. Brenzel, St. Paul, MN (US); Paul Hindrichs, Plymouth, MN (US); Alex A. Peterson, Maple Grove, MN (US)

(73) Assignee: Conventus Orthopaedics, Inc., Maple Grove, MN (US)

( * ) Notice: Subject to any disclaimer, the term of this patent is extended or adjusted under 35 U.S.C. 154(b) by 246 days.

(21) Appl. No.: 13/043,190

(22) Filed: Mar. 8, 2011

(65) Prior Publication Data

US 2011/0218626 A1 Sep. 8, 2011

Related U.S. Application Data

(60) Provisional application No. 61/311,494, filed on Mar. 8, 2010, provisional application No. 61/378,822, filed on Aug. 31, 2010.

(51) Int. Cl.
*A61B 17/56* (2006.01)
*A61B 17/68* (2006.01)
*A61B 17/88* (2006.01)
*A61B 17/80* (2006.01)

(52) U.S. Cl.
CPC ............. *A61B 17/68* (2013.01); *A61B 17/8858* (2013.01); *A61B 17/8061* (2013.01)
USPC .......................................................... 606/63

(58) Field of Classification Search
USPC .................................... 606/62–64, 300–321
See application file for complete search history.

(56) References Cited

U.S. PATENT DOCUMENTS 1,362,513 A 12/1919 Skinner
1,344,327 A 6/1920 Wilson
(Continued)

FOREIGN PATENT DOCUMENTS

AU 2006247498 A1 12/2007
AU 1885263 A1 2/2008
(Continued)

OTHER PUBLICATIONS

App No. PCT/US/2011/027597 International Search Report.
(Continued)

*Primary Examiner* — Ellen C Hammond
*Assistant Examiner* — Stuart S Bray
(74) *Attorney, Agent, or Firm* — Weiss & Arons LLP

(57) ABSTRACT

Apparatus and methods for securing a bone implant are provided. The implant may be an expandable implant. The implant may be a non-expandable implant. The implant may be for repairing a bone fracture. The implant may be secured to a bone by anchors. The implant may include anchor receiving features. The anchor receiving features may be configured to direct an anchor into cortical bone. The anchor receiving features may be configured to receive an anchor driven through cortical bone. The implant may include bone engaging members configured to engage cancellous bone. An implant may include different profiles. The different profiles may be configured to secure the implant. The profiles may be configured to support the bone. The implant may have different flexing properties configured to position the implant in the bone. The implant may be positioned to receive an anchor driven through an outside of the bone.

54 Claims, 49 Drawing Sheets

(56) References Cited

U.S. PATENT DOCUMENTS

| | | |
|---|---|---|
| 1,493,240 A | 5/1924 | Bohn |
| 1,685,380 A | 9/1928 | Shultz |
| 2,137,710 A | 12/1937 | Anderson |
| 2,485,531 A | 1/1948 | Dzus et al. |
| 2,493,598 A | 1/1950 | Rozek |
| 2,537,070 A | 1/1951 | Longfellow |
| 2,580,821 A | 1/1952 | Nicola |
| 2,730,101 A | 1/1956 | Hoffman |
| 2,780,223 A | 2/1957 | Haggland |
| 3,143,915 A | 8/1964 | Tendler |
| 3,143,916 A | 8/1964 | Rice |
| 3,181,533 A | 5/1965 | Heath |
| 3,495,586 A | 2/1970 | Regenbogen |
| 3,517,128 A | 6/1970 | Hines |
| 3,593,342 A | 7/1971 | Niebauer et al. |
| 3,623,164 A | 11/1971 | Bokros |
| 3,640,280 A | 2/1972 | Slanker et al. |
| 3,702,611 A | 11/1972 | Fishbein |
| 3,710,789 A | 1/1973 | Ersek |
| 3,744,488 A | 7/1973 | Cox |
| 3,745,590 A | 7/1973 | Stubstad |
| 3,759,257 A | 9/1973 | Fischer et al. |
| 3,760,802 A | 9/1973 | Fischer et al. |
| 3,779,239 A | 12/1973 | Fischer et al. |
| 3,805,775 A | 4/1974 | Fischer et al. |
| 3,828,790 A | 8/1974 | Curtiss et al. |
| 3,886,600 A | 6/1975 | Kahn et al. |
| 3,909,853 A | 10/1975 | Lennox |
| 3,917,249 A | 11/1975 | Constantine |
| 3,946,445 A | 3/1976 | Bentley et al. |
| 3,970,075 A | 7/1976 | Sindelar et al. |
| 3,986,504 A | 10/1976 | Avila |
| 3,992,726 A | 11/1976 | Freeman et al. |
| 4,036,107 A | 7/1977 | Constantine |
| 4,091,806 A | 5/1978 | Aginsky |
| 4,124,026 A | 11/1978 | Berner et al. |
| 4,156,296 A | 5/1979 | Johnson et al. |
| 4,180,871 A | 1/1980 | Hamas |
| 4,190,044 A | 2/1980 | Wood |
| 4,193,139 A | 3/1980 | Walker |
| 4,194,250 A | 3/1980 | Walker |
| 4,203,444 A | 5/1980 | Bonnell et al. |
| 4,204,531 A | 5/1980 | Aginsky |
| 4,213,208 A | 7/1980 | Marne |
| 4,227,518 A | 10/1980 | Aginsky |
| 4,229,840 A | 10/1980 | Gristina |
| 4,231,121 A | 11/1980 | Lewis |
| 4,262,665 A | 4/1981 | Roalstad et al. |
| 4,273,128 A | 6/1981 | Lary |
| 4,274,398 A | 6/1981 | Scott et al. |
| 4,275,717 A | 6/1981 | Bolesky |
| 4,293,962 A | 10/1981 | Fuson |
| 4,313,434 A | 2/1982 | Segal |
| 4,349,922 A | 9/1982 | Agee |
| 4,352,212 A | 10/1982 | Greene et al. |
| 4,430,991 A | 2/1984 | Darnell |
| 4,453,539 A | 6/1984 | Raftopoulos et al. |
| 4,473,070 A | 9/1984 | Matthews et al. |
| 4,485,816 A | 12/1984 | Krumme |
| 4,502,554 A | 3/1985 | Jones |
| 4,519,100 A | 5/1985 | Wills et al. |
| 4,522,200 A | 6/1985 | Stednitz |
| 4,548,199 A | 10/1985 | Agee |
| 4,572,186 A | 2/1986 | Gould et al. |
| 4,573,448 A | 3/1986 | Kambin |
| 4,585,000 A | 4/1986 | Hershenson |
| 4,590,930 A | 5/1986 | Kurth et al. |
| 4,601,290 A | 7/1986 | Effron et al. |
| 4,611,594 A | 9/1986 | Grayhack et al. |
| 4,627,434 A | 12/1986 | Murray |
| 4,634,445 A | 1/1987 | Helal |
| 4,643,177 A | 2/1987 | Sheppard et al. |
| 4,644,951 A | 2/1987 | Bays |
| 4,646,738 A | 3/1987 | Trott |
| 4,655,203 A | 4/1987 | Tormala et al. |
| 4,660,557 A | 4/1987 | Collis |
| 4,662,371 A | 5/1987 | Whipple et al. |
| 4,665,906 A | 5/1987 | Jervis |
| 4,669,237 A | 6/1987 | Constantine |
| 4,674,488 A | 6/1987 | Nashef et al. |
| 4,705,027 A | 11/1987 | Klaue |
| 4,721,103 A | 1/1988 | Freedland |
| 4,730,608 A | 3/1988 | Schlein |
| 4,731,087 A | 3/1988 | Sculco et al. |
| 4,751,922 A | 6/1988 | DiPietropolo |
| 4,777,942 A | 10/1988 | Frey et al. |
| 4,782,833 A | 11/1988 | Einhorn et al. |
| 4,790,302 A | 12/1988 | Colwill et al. |
| 4,809,793 A | 3/1989 | Hailey |
| 4,820,305 A | 4/1989 | Harms et al. |
| 4,875,474 A | 10/1989 | Border |
| 4,886,062 A | 12/1989 | Wiktor |
| 4,914,818 A | 4/1990 | Hall et al. |
| 4,921,478 A | 5/1990 | Solano et al. |
| 4,941,466 A | 7/1990 | Romano |
| 4,946,459 A | 8/1990 | Bradshaw et al. |
| 4,954,126 A | 9/1990 | Wallsten |
| 4,955,916 A | 9/1990 | Carignan et al. |
| 4,969,888 A | 11/1990 | Scholten et al. |
| 4,973,257 A | 11/1990 | Lhotak |
| 4,978,349 A | 12/1990 | Frigg |
| 4,998,539 A | 3/1991 | Delsanti |
| 5,002,546 A | 3/1991 | Romano |
| 5,015,255 A | 5/1991 | Kuslich |
| 5,030,201 A | 7/1991 | Palestrant |
| 5,035,714 A | 7/1991 | Willert et al. |
| 5,053,036 A | 10/1991 | Perren et al. |
| 5,059,193 A | 10/1991 | Kuslich |
| 5,062,845 A | 11/1991 | Kuslich et al. |
| 5,066,296 A | 11/1991 | Chapman et al. |
| 5,067,957 A | 11/1991 | Jervis |
| 5,071,407 A | 12/1991 | Termin et al. |
| 5,084,050 A | 1/1992 | Draenert |
| 5,100,423 A | 3/1992 | Fearnot |
| 5,102,413 A | 4/1992 | Poddar |
| 5,108,404 A | 4/1992 | Scholten et al. |
| 5,108,435 A | 4/1992 | Gustavson et al. |
| 5,112,333 A | 5/1992 | Fixel |
| 5,113,846 A | 5/1992 | Hiltebrandt et al. |
| 5,116,335 A | 5/1992 | Hannon et al. |
| 5,122,134 A | 6/1992 | Borzone et al. |
| 5,139,497 A | 8/1992 | Tilghman et al. |
| 5,151,103 A | 9/1992 | Tepic et al. |
| 5,169,402 A | 12/1992 | Elloy |
| 5,171,284 A | 12/1992 | Branemark |
| 5,174,374 A | 12/1992 | Hailey |
| 5,180,382 A | 1/1993 | Frigg et al. |
| 5,190,545 A | 3/1993 | Corsi et al. |
| 5,190,546 A | 3/1993 | Jervis |
| 5,190,548 A | 3/1993 | Davis |
| 5,197,966 A | 3/1993 | Sommerkamp |
| 5,197,967 A | 3/1993 | Wilson |
| 5,197,971 A | 3/1993 | Bonutti |
| 5,201,741 A | 4/1993 | Dulebohn |
| 5,203,773 A | 4/1993 | Green |
| 5,221,261 A | 6/1993 | Termin et al. |
| 5,236,431 A | 8/1993 | Gogolewski et al. |
| 5,242,017 A | 9/1993 | Hailey |
| 5,242,461 A | 9/1993 | Kortenbach et al. |
| 5,250,048 A | 10/1993 | Gundolf |
| 5,263,955 A | 11/1993 | Baumgart et al. |
| 5,269,785 A | 12/1993 | Bonutti |
| 5,275,602 A | 1/1994 | Shimizu et al. |
| 5,275,608 A | 1/1994 | Forman et al. |
| 5,281,225 A | 1/1994 | Vicenzi |
| 5,281,226 A | 1/1994 | Davydov et al. |
| 5,286,249 A | 2/1994 | Thibodaux |
| 5,307,790 A | 5/1994 | Byrne |
| 5,314,486 A | 5/1994 | Zang et al. |
| 5,326,205 A | 7/1994 | Anspach et al. |
| 5,334,184 A | 8/1994 | Bimman |
| 5,358,405 A | 10/1994 | Imai |
| 5,376,097 A | 12/1994 | Phillips |
| 5,376,100 A | 12/1994 | Lefebvre |

(56) References Cited

U.S. PATENT DOCUMENTS

| | | |
|---|---|---|
| 5,378,239 A | 1/1995 | Termin et al. |
| 5,380,328 A | 1/1995 | Morgan |
| 5,397,320 A | 3/1995 | Essig et al. |
| 5,415,660 A | 5/1995 | Campbell et al. |
| 5,423,823 A | 6/1995 | Schmieding |
| 5,431,671 A | 7/1995 | Nallakrishnan |
| 5,437,665 A | 8/1995 | Munro |
| 5,437,674 A | 8/1995 | Worcel et al. |
| 5,439,464 A | 8/1995 | Shapiro |
| 5,445,639 A | 8/1995 | Kuslich et al. |
| 5,454,365 A | 10/1995 | Bonutti |
| 5,458,599 A | 10/1995 | Adobbati |
| 5,458,648 A | 10/1995 | Berman et al. |
| 5,467,763 A | 11/1995 | McMahon et al. |
| D365,634 S | 12/1995 | Morgan |
| 5,474,557 A | 12/1995 | Mai |
| 5,480,447 A | 1/1996 | Skiba |
| 5,496,277 A | 3/1996 | Termin et al. |
| 5,496,330 A | 3/1996 | Bates et al. |
| 5,499,981 A | 3/1996 | Kordis |
| 5,501,695 A | 3/1996 | Anspach et al. |
| 5,505,734 A | 4/1996 | Caniggia et al. |
| 5,509,919 A | 4/1996 | Young |
| 5,512,037 A | 4/1996 | Russell et al. |
| 5,527,316 A | 6/1996 | Stone et al. |
| 5,531,792 A | 7/1996 | Huene |
| 5,536,267 A | 7/1996 | Edwards et al. |
| 5,540,693 A | 7/1996 | Fisher |
| 5,545,162 A | 8/1996 | Huebner |
| 5,554,163 A | 9/1996 | Shturman |
| 5,556,408 A | 9/1996 | Farhat |
| 5,571,098 A | 11/1996 | Domankevitz et al. |
| 5,571,189 A | 11/1996 | Kuslich |
| 5,582,577 A | 12/1996 | Lund et al. |
| 5,582,618 A | 12/1996 | Chin et al. |
| 5,586,983 A | 12/1996 | Sanders et al. |
| 5,586,985 A | 12/1996 | Putnam et al. |
| 5,586,990 A | 12/1996 | Hahnen et al. |
| 5,591,169 A | 1/1997 | Benoist |
| 5,591,170 A | 1/1997 | Spievack et al. |
| 5,597,378 A | 1/1997 | Jervis |
| 5,602,935 A | 2/1997 | Yoshida et al. |
| 5,620,414 A | 4/1997 | Campbell |
| 5,620,445 A | 4/1997 | Brosnahan et al. |
| 5,624,440 A | 4/1997 | Huebner |
| 5,624,447 A | 4/1997 | Myers |
| 5,626,580 A | 5/1997 | Brosnahan |
| 5,645,589 A | 7/1997 | Li |
| 5,658,280 A | 8/1997 | Issa |
| 5,658,283 A | 8/1997 | Huebner |
| 5,660,188 A | 8/1997 | Groiso |
| 5,662,649 A | 9/1997 | Huebner |
| 5,667,509 A | 9/1997 | Westin |
| 5,676,545 A | 10/1997 | Jones |
| 5,676,699 A | 10/1997 | Gogolewski et al. |
| 5,681,310 A | 10/1997 | Yuan et al. |
| 5,683,389 A | 11/1997 | Orsak |
| 5,685,826 A | 11/1997 | Bonutti |
| 5,693,011 A | 12/1997 | Onik |
| 5,697,981 A | 12/1997 | Ison et al. |
| 5,707,374 A | 1/1998 | Schmidt |
| 5,709,697 A | 1/1998 | Ratcliff et al. |
| 5,718,704 A | 2/1998 | Medoff |
| 5,725,541 A | 3/1998 | Anspach, III et al. |
| 5,728,047 A | 3/1998 | Edoga |
| 5,728,098 A | 3/1998 | Sherman et al. |
| 5,730,704 A | 3/1998 | Avitall |
| 5,741,266 A | 4/1998 | Moran et al. |
| 5,741,282 A | 4/1998 | Anspach et al. |
| 5,758,713 A | 6/1998 | Fallet |
| 5,779,703 A | 7/1998 | Benoist |
| 5,792,106 A | 8/1998 | Mische |
| 5,810,721 A | 9/1998 | Mueller et al. |
| 5,814,044 A | 9/1998 | Hooven |
| 5,817,098 A | 10/1998 | Albrektsson et al. |
| 5,824,095 A | 10/1998 | Di Maio, Jr. et al. |
| 5,827,289 A | 10/1998 | Reiley et al. |
| 5,827,312 A | 10/1998 | Brown et al. |
| D403,069 S | 12/1998 | Drewry et al. |
| 5,853,054 A | 12/1998 | McGarian et al. |
| 5,876,399 A | 3/1999 | Chia et al. |
| 5,879,352 A | 3/1999 | Filoso et al. |
| 5,879,355 A | 3/1999 | Ullmark |
| 5,885,258 A | 3/1999 | Sachdeva et al. |
| 5,885,282 A | 3/1999 | Szabo |
| 5,888,196 A | 3/1999 | Bonutti |
| 5,891,147 A | 4/1999 | Moskovitz et al. |
| 5,893,850 A | 4/1999 | Cachia |
| 5,897,556 A | 4/1999 | Drewry et al. |
| 5,908,423 A | 6/1999 | Kashuba et al. |
| 5,915,036 A | 6/1999 | Grunkin et al. |
| 5,919,195 A | 7/1999 | Wilson et al. |
| 5,925,039 A | 7/1999 | Landingham |
| 5,928,239 A | 7/1999 | Mirza |
| 5,935,127 A | 8/1999 | Border |
| 5,938,699 A | 8/1999 | Campbell |
| 5,941,878 A | 8/1999 | Medoff |
| 5,951,467 A | 9/1999 | Picha et al. |
| 5,951,556 A | 9/1999 | Faccioli et al. |
| 5,957,884 A | 9/1999 | Hooven |
| 5,964,698 A | 10/1999 | Fowle |
| 5,976,134 A | 11/1999 | Huebner |
| 5,980,525 A | 11/1999 | Bryant et al. |
| 5,984,932 A | 11/1999 | Yoon |
| 5,984,937 A | 11/1999 | Morse et al. |
| 5,997,538 A | 12/1999 | Asnis et al. |
| 6,001,099 A | 12/1999 | Huebner |
| 6,015,406 A | 1/2000 | Goble et al. |
| 6,019,762 A | 2/2000 | Cole |
| 6,019,947 A | 2/2000 | Kucherov |
| 6,033,412 A | 3/2000 | Losken et al. |
| 6,045,564 A | 4/2000 | Walen |
| 6,048,309 A | 4/2000 | Flom et al. |
| 6,053,922 A | 4/2000 | Krause et al. |
| 6,056,750 A | 5/2000 | Lob |
| 6,068,642 A | 5/2000 | Johnson et al. |
| 6,068,648 A | 5/2000 | Cole et al. |
| 6,074,392 A | 6/2000 | Durham |
| 6,093,162 A | 7/2000 | Fairleigh et al. |
| 6,096,040 A | 8/2000 | Esser |
| 6,113,603 A | 9/2000 | Medoff |
| 6,120,472 A | 9/2000 | Singer |
| 6,120,504 A | 9/2000 | Brumback et al. |
| 6,123,704 A | 9/2000 | Hajianpour |
| 6,126,662 A | 10/2000 | Carmichael et al. |
| 6,127,597 A | 10/2000 | Beyar et al. |
| 6,129,762 A | 10/2000 | Li |
| 6,142,935 A | 11/2000 | Flom et al. |
| 6,143,012 A | 11/2000 | Gausepohl |
| 6,149,651 A | 11/2000 | Drewry et al. |
| 6,149,689 A | 11/2000 | Grundei |
| 6,156,069 A | 12/2000 | Amstutz |
| 6,162,223 A | 12/2000 | Orsak et al. |
| 6,162,224 A | 12/2000 | Huebner |
| 6,171,309 B1 | 1/2001 | Huebner |
| 6,174,312 B1 | 1/2001 | Laminger |
| 6,197,027 B1 | 3/2001 | Hajianpour |
| 6,200,330 B1 | 3/2001 | Benderev et al. |
| 6,216,573 B1 | 4/2001 | Moutafis et al. |
| 6,221,074 B1 | 4/2001 | Cole et al. |
| 6,221,102 B1 | 4/2001 | Baker et al. |
| 6,224,600 B1 | 5/2001 | Protogirou |
| 6,224,604 B1 | 5/2001 | Suddaby |
| 6,231,576 B1 | 5/2001 | Frigg et al. |
| 6,235,043 B1 | 5/2001 | Reiley et al. |
| 6,238,417 B1 | 5/2001 | Cole |
| 6,241,734 B1 | 6/2001 | Scribner et al. |
| 6,248,110 B1 | 6/2001 | Reiley et al. |
| 6,258,096 B1 | 7/2001 | Seki |
| 6,261,289 B1 | 7/2001 | Levy |
| 6,280,474 B1 | 8/2001 | Cassidy et al. |
| 6,296,639 B1 | 10/2001 | Truckai et al. |
| 6,299,642 B1 | 10/2001 | Chan |
| 6,302,915 B1 | 10/2001 | Cooney et al. |

(56) References Cited

U.S. PATENT DOCUMENTS

| | | |
|---|---|---|
| 6,306,141 B1 | 10/2001 | Jervis |
| 6,312,467 B1 | 11/2001 | Mcgee |
| 6,319,255 B1 | 11/2001 | Grundei et al. |
| 6,322,591 B1 | 11/2001 | Ahrens |
| 6,331,166 B1 | 12/2001 | Burbank et al. |
| 6,332,885 B1 | 12/2001 | Martella |
| 6,332,886 B1 | 12/2001 | Green et al. |
| 6,348,053 B1 | 2/2002 | Cachia |
| 6,364,909 B1 | 4/2002 | Mcgee |
| 6,365,555 B1 | 4/2002 | Moser et al. |
| 6,375,666 B1 | 4/2002 | Mische |
| 6,383,188 B2 | 5/2002 | Kuslich et al. |
| 6,402,753 B1 | 6/2002 | Cole et al. |
| 6,411,729 B1 | 6/2002 | Grunkin |
| 6,416,517 B2 | 7/2002 | Harder et al. |
| 6,423,070 B1 | 7/2002 | Zeppelin |
| 6,440,138 B1 | 8/2002 | Reiley et al. |
| 6,447,514 B1 | 9/2002 | Stalcup et al. |
| 6,447,515 B1 | 9/2002 | Meldrum |
| 6,447,518 B1 | 9/2002 | Krause et al. |
| 6,454,810 B1 | 9/2002 | Lob |
| 6,468,207 B1 | 10/2002 | Fowler |
| 6,475,789 B1 | 11/2002 | Cech et al. |
| 6,488,685 B1 | 12/2002 | Manderson |
| 6,491,694 B1 | 12/2002 | Orsak |
| 6,511,481 B2 | 1/2003 | von Hoffmann et al. |
| 6,517,541 B1 | 2/2003 | Sesic |
| 6,527,775 B1 | 3/2003 | Warburton |
| 6,533,788 B1 | 3/2003 | Orbay |
| 6,540,770 B1 | 4/2003 | Tornier et al. |
| 6,544,267 B1 | 4/2003 | Cole et al. |
| 6,554,833 B2 | 4/2003 | Levy et al. |
| 6,575,878 B1 | 6/2003 | Choy |
| 6,575,973 B1 | 6/2003 | Shekalim |
| 6,575,978 B2 | 6/2003 | Peterson et al. |
| 6,582,467 B1 | 6/2003 | Teitelbaum et al. |
| 6,585,736 B2 | 7/2003 | Hajianpour |
| 6,585,770 B1 | 7/2003 | White et al. |
| 6,610,839 B1 | 8/2003 | Morin et al. |
| 6,613,052 B1 | 9/2003 | Kinnett |
| 6,613,054 B2 | 9/2003 | Scribner et al. |
| 6,617,110 B1 | 9/2003 | Cech et al. |
| 6,632,224 B2 | 10/2003 | Cachia et al. |
| 6,641,616 B1 | 11/2003 | Grundei |
| 6,645,210 B2 | 11/2003 | Manderson |
| 6,648,890 B2 | 11/2003 | Culbert et al. |
| 6,652,585 B2 | 11/2003 | Lange |
| 6,656,187 B1 | 12/2003 | Camino |
| 6,656,219 B1 | 12/2003 | Wiktor |
| 6,660,009 B1 | 12/2003 | Azar |
| 6,660,041 B1 | 12/2003 | Grundei |
| 6,676,665 B2 | 1/2004 | Foley et al. |
| 6,679,886 B2 | 1/2004 | Weikel et al. |
| 6,682,565 B1 | 1/2004 | Krishnan |
| 6,685,706 B2 | 2/2004 | Padget et al. |
| 6,689,138 B2 | 2/2004 | Léchot et al. |
| 6,692,496 B1 | 2/2004 | Wardlaw |
| 6,701,174 B1 | 3/2004 | Krause et al. |
| 6,709,433 B1 | 3/2004 | Schoenefeld |
| 6,711,432 B1 | 3/2004 | Krause et al. |
| 6,712,073 B2 | 3/2004 | Manderson |
| 6,712,858 B1 | 3/2004 | Grungei et al. |
| 6,719,761 B1 | 4/2004 | Reiley et al. |
| 6,719,793 B2 | 4/2004 | McGee et al. |
| 6,746,451 B2 | 6/2004 | Middleton et al. |
| 6,749,611 B2 | 6/2004 | Venturini et al. |
| 6,755,831 B2 | 6/2004 | Putnam et al. |
| 6,755,862 B2 | 6/2004 | Keynan |
| 6,761,722 B2 | 7/2004 | Cole et al. |
| 6,767,350 B1 | 7/2004 | Lob |
| 6,775,401 B2 | 8/2004 | Hwang et al. |
| 6,780,185 B2 | 8/2004 | Frei et al. |
| 6,783,530 B1 * | 8/2004 | Levy ..................... 606/63 |
| 6,783,532 B2 | 8/2004 | Steiner et al. |
| 6,783,533 B2 | 8/2004 | Green et al. |
| 6,793,655 B2 | 9/2004 | Orsak |
| 6,793,659 B2 | 9/2004 | Putnam |
| 6,811,568 B2 | 11/2004 | Minamikawa |
| 6,827,723 B2 | 12/2004 | Carson |
| 6,827,743 B2 | 12/2004 | Eisermann et al. |
| 6,849,051 B2 | 2/2005 | Sramek et al. |
| 6,852,128 B2 | 2/2005 | Lange |
| 6,866,665 B2 | 3/2005 | Orbay |
| 6,887,243 B2 | 5/2005 | Culbert |
| 6,890,333 B2 | 5/2005 | von Hoffmann et al. |
| 6,893,444 B2 | 5/2005 | Orbay |
| 6,908,465 B2 | 6/2005 | von Hoffmann et al. |
| 6,911,046 B2 | 6/2005 | Schulter |
| 6,913,605 B2 | 7/2005 | Fletcher et al. |
| 6,923,813 B2 | 8/2005 | Phillips et al. |
| 6,923,817 B2 | 8/2005 | Carson et al. |
| 6,923,828 B1 | 8/2005 | Wiktor |
| 6,926,720 B2 | 8/2005 | Castañeda |
| 6,932,086 B1 | 8/2005 | Hajianpour |
| 6,942,666 B2 | 9/2005 | Overaker et al. |
| 6,942,668 B2 | 9/2005 | Padget et al. |
| 6,949,101 B2 | 9/2005 | McCleary et al. |
| 6,951,561 B2 | 10/2005 | Warren et al. |
| 6,975,894 B2 | 12/2005 | Wehrli et al. |
| 6,984,248 B2 | 1/2006 | Hyde, Jr. |
| 6,986,771 B2 | 1/2006 | Paul et al. |
| 6,989,011 B2 | 1/2006 | Paul et al. |
| 6,991,656 B2 | 1/2006 | Mears |
| 7,008,425 B2 | 3/2006 | Phillips |
| 7,008,428 B2 | 3/2006 | Cachia et al. |
| 7,008,430 B2 | 3/2006 | Dong et al. |
| 7,011,662 B2 | 3/2006 | Lechot et al. |
| 7,018,332 B1 | 3/2006 | Masson et al. |
| 7,018,380 B2 | 3/2006 | Cole |
| 7,022,069 B1 | 4/2006 | Masson et al. |
| 7,025,789 B2 | 4/2006 | Chow et al. |
| 7,041,104 B1 | 5/2006 | Cole et al. |
| 7,041,138 B2 | 5/2006 | Lange |
| 7,048,542 B2 | 5/2006 | Von Arx et al. |
| 7,052,498 B2 | 5/2006 | Levy et al. |
| 7,063,701 B2 | 6/2006 | Michelson |
| 7,070,601 B2 | 7/2006 | Culbert et al. |
| 7,090,676 B2 | 8/2006 | Huebner et al. |
| 7,097,646 B2 | 8/2006 | Schantz |
| 7,097,648 B1 | 8/2006 | Globerman et al. |
| 7,122,033 B2 * | 10/2006 | Wood .......................... 606/41 |
| 7,122,043 B2 | 10/2006 | Greenhalgh et al. |
| 7,122,052 B2 | 10/2006 | Greenhalgh |
| 7,131,995 B2 | 11/2006 | Biedermann et al. |
| 7,137,987 B2 | 11/2006 | Patterson et al. |
| 7,141,054 B2 | 11/2006 | Vandewalle |
| 7,141,067 B2 | 11/2006 | Jones et al. |
| 7,147,640 B2 | 12/2006 | Huebner et al. |
| 7,153,307 B2 | 12/2006 | Scribner et al. |
| 7,153,309 B2 | 12/2006 | Huebner et al. |
| 7,160,302 B2 | 1/2007 | Warburton |
| 7,160,331 B2 | 1/2007 | Cooney et al. |
| 7,172,595 B1 | 2/2007 | Goble |
| 7,175,625 B2 | 2/2007 | Culbert |
| 7,179,024 B2 | 2/2007 | Greenhalgh |
| 7,189,237 B2 | 3/2007 | Huebner |
| 7,189,240 B1 | 3/2007 | Dekel |
| 7,195,589 B1 | 3/2007 | Masson et al. |
| 7,195,633 B2 | 3/2007 | Medoff et al. |
| 7,214,227 B2 | 5/2007 | Colleran et al. |
| 7,220,282 B2 | 5/2007 | Kuslich et al. |
| 7,229,441 B2 | 6/2007 | Trieu et al. |
| 7,235,079 B2 | 6/2007 | Jensen et al. |
| 7,237,556 B2 | 7/2007 | Smothers et al. |
| 7,255,712 B1 | 8/2007 | Steinberg |
| 7,258,692 B2 | 8/2007 | Thelen et al. |
| 7,264,622 B2 | 9/2007 | Michelson |
| 7,267,678 B2 | 9/2007 | Medoff |
| 7,282,053 B2 | 10/2007 | Orbay |
| 7,294,130 B2 | 11/2007 | Orbay |
| 7,300,449 B2 | 11/2007 | Mische et al. |
| 7,306,603 B2 | 12/2007 | Boehm et al. |
| 7,306,683 B2 | 12/2007 | Cheung et al. |
| 7,311,711 B2 | 12/2007 | Cole |

(56) References Cited

U.S. PATENT DOCUMENTS

| | | | |
|---|---|---|---|
| D560,128 S | 1/2008 | Diederich et al. |
| 7,322,938 B2 | 1/2008 | Burbank et al. |
| 7,326,249 B2 | 2/2008 | Lange |
| 7,329,228 B2 | 2/2008 | Burbank et al. |
| 7,341,601 B2 | 3/2008 | Eisermann et al. |
| 7,344,539 B2 | 3/2008 | Serhan et al. |
| 7,354,453 B2 | 4/2008 | McAfee |
| 7,422,360 B2 | 9/2008 | Kozyuk |
| 7,465,318 B2 | 12/2008 | Sennett et al. |
| 7,476,226 B2 | 1/2009 | Weikel et al. |
| 7,481,815 B2 | 1/2009 | Fernandez |
| 7,485,119 B2 | 2/2009 | Thelen et al. |
| 7,488,320 B2 | 2/2009 | Middleton |
| 7,488,329 B2 | 2/2009 | Thelen et al. |
| D589,147 S | 3/2009 | Colleran et al. |
| 7,500,977 B2 | 3/2009 | Assell et al. |
| 7,507,241 B2 | 3/2009 | Levy et al. |
| 7,520,879 B2 | 4/2009 | Justis et al. |
| 7,563,263 B2 | 7/2009 | Orbay et al. |
| 7,569,061 B2 | 8/2009 | Colleran |
| 7,578,824 B2 | 8/2009 | Justin et al. |
| 7,588,575 B2 | 9/2009 | Colleran et al. |
| 7,588,577 B2 | 9/2009 | Fencl et al. |
| 7,588,588 B2 | 9/2009 | Spitler et al. |
| 7,601,152 B2 | 10/2009 | Levy et al. |
| 7,611,515 B2 | 11/2009 | Wolford et al. |
| 7,621,950 B1 | 11/2009 | Globerman et al. |
| 7,632,277 B2 | 12/2009 | Woll et al. |
| 7,632,310 B2 | 12/2009 | Clifford et al. |
| 7,666,226 B2 | 2/2010 | Schaller |
| 7,670,339 B2 | 3/2010 | Levy et al. |
| 7,670,374 B2 | 3/2010 | Schaller |
| 7,670,375 B2 | 3/2010 | Schaller |
| 7,682,364 B2 | 3/2010 | Reiley et al. |
| 7,695,471 B2 | 4/2010 | Cheung et al. |
| 7,695,502 B2 | 4/2010 | Orbay et al. |
| 7,704,251 B2 | 4/2010 | Huebner et al. |
| 7,708,742 B2 | 5/2010 | Scribner et al. |
| 7,713,271 B2 | 5/2010 | Warburton et al. |
| 7,722,612 B2 | 5/2010 | Sala et al. |
| 7,722,626 B2 | 5/2010 | Middleman et al. |
| 7,727,264 B2 | 6/2010 | Orbay et al. |
| 7,731,720 B2 | 6/2010 | Sand et al. |
| 7,749,232 B2 | 7/2010 | Salerni |
| 7,758,500 B2 | 7/2010 | Boyd et al. |
| 7,785,368 B2 | 8/2010 | Schaller |
| 7,806,929 B2 | 10/2010 | Brown |
| 7,811,291 B2 | 10/2010 | Liu et al. |
| 7,828,802 B2 | 11/2010 | Levy et al. |
| 7,837,612 B2 | 11/2010 | Gill et al. |
| 7,842,041 B2 | 11/2010 | Liu et al. |
| 7,846,162 B2 | 12/2010 | Nelson et al. |
| 7,879,103 B2 | 2/2011 | Gertzman et al. |
| 7,905,909 B2 | 3/2011 | Orbay et al. |
| 7,909,825 B2 | 3/2011 | Saravia et al. |
| 7,909,873 B2 | 3/2011 | Tan-Malecki et al. |
| 7,914,533 B2 | 3/2011 | Nelson et al. |
| 7,931,689 B2 | 4/2011 | Hochschuler et al. |
| 7,942,875 B2 | 5/2011 | Nelson et al. |
| 7,959,634 B2 | 6/2011 | Sennett |
| 7,959,638 B2 | 6/2011 | Osorio et al. |
| 7,959,683 B2 | 6/2011 | Semler et al. |
| 7,967,827 B2 | 6/2011 | Osorio et al. |
| 7,967,865 B2 | 6/2011 | Schaller |
| 7,972,340 B2 | 7/2011 | Sand et al. |
| 7,988,735 B2 | 8/2011 | Yurek et al. |
| 8,007,498 B2 | 8/2011 | Mische |
| RE42,757 E | 9/2011 | Kuslich et al. |
| 8,021,365 B2 | 9/2011 | Phan |
| 8,021,366 B2 | 9/2011 | Phan |
| 8,043,334 B2 | 10/2011 | Fisher et al. |
| 8,057,544 B2 | 11/2011 | Schaller |
| 8,105,236 B2 | 1/2012 | Malandain et al. |
| 8,109,933 B2 | 2/2012 | Truckai et al. |
| 8,114,084 B2 | 2/2012 | Betts |
| 8,118,952 B2 | 2/2012 | Gall et al. |
| 8,128,627 B2 | 3/2012 | Justin et al. |
| 8,152,737 B2 | 4/2012 | Burbank et al. |
| 8,157,804 B2 | 4/2012 | Betts |
| 8,226,719 B2 | 7/2012 | Melsheimer et al. |
| 8,241,335 B2 | 8/2012 | Truckai et al. |
| 8,287,538 B2 * | 10/2012 | Brenzel et al. ............... 606/62 |
| 8,287,539 B2 | 10/2012 | Nelson et al. |
| 8,287,541 B2 | 10/2012 | Nelson et al. |
| 8,317,791 B2 | 11/2012 | Phan |
| 8,353,911 B2 | 1/2013 | Goldin et al. |
| 8,366,773 B2 | 2/2013 | Schaller et al. |
| 8,409,211 B2 | 4/2013 | Baroud |
| 8,430,879 B2 | 4/2013 | Stoneburner et al. |
| 8,439,917 B2 | 5/2013 | Saravia et al. |
| 8,491,591 B2 | 7/2013 | Fürderer |
| 8,496,657 B2 * | 7/2013 | Bonutti et al. ............... 606/62 |
| 8,496,658 B2 | 7/2013 | Stoneburner et al. |
| 8,568,413 B2 | 10/2013 | Mazur et al. |
| 2001/0018588 A1 | 8/2001 | Harder et al. |
| 2001/0034526 A1 | 10/2001 | Kuslich et al. |
| 2001/0053912 A1 | 12/2001 | Frigg |
| 2002/0013600 A1 | 1/2002 | Scribner et al. |
| 2002/0015517 A1 | 2/2002 | Hwang et al. |
| 2002/0029081 A1 | 3/2002 | Scarborough et al. |
| 2002/0032444 A1 * | 3/2002 | Mische ............... 606/63 |
| 2002/0055742 A1 | 5/2002 | Lieberman |
| 2002/0055785 A1 | 5/2002 | Harris |
| 2002/0068974 A1 | 6/2002 | Kuslich et al. |
| 2002/0111629 A1 | 8/2002 | Phillips |
| 2002/0111690 A1 | 8/2002 | Hyde |
| 2002/0120269 A1 | 8/2002 | Lange |
| 2002/0120270 A1 | 8/2002 | Trieu et al. |
| 2002/0123750 A1 | 9/2002 | Eisermann et al. |
| 2002/0133153 A1 | 9/2002 | Hyde |
| 2002/0133156 A1 | 9/2002 | Cole |
| 2002/0133172 A1 | 9/2002 | Lambrecht et al. |
| 2002/0133175 A1 | 9/2002 | Carson |
| 2002/0138149 A1 | 9/2002 | Hyde |
| 2002/0143329 A1 | 10/2002 | Serhan et al. |
| 2002/0143333 A1 | 10/2002 | von Hoffmann et al. |
| 2002/0143334 A1 | 10/2002 | Hoffmann et al. |
| 2002/0143335 A1 | 10/2002 | von Hoffmann et al. |
| 2002/0147451 A1 * | 10/2002 | McGee ............... 606/62 |
| 2002/0147455 A1 | 10/2002 | Carson |
| 2002/0165461 A1 | 11/2002 | Hayzelden et al. |
| 2002/0171208 A1 | 11/2002 | Lechot et al. |
| 2002/0173813 A1 | 11/2002 | Peterson et al. |
| 2002/0183758 A1 | 12/2002 | Middleton et al. |
| 2002/0191823 A1 | 12/2002 | Wehrli et al. |
| 2003/0040805 A1 | 2/2003 | Minamikawa |
| 2003/0055373 A1 | 3/2003 | Sramek et al. |
| 2003/0055425 A1 | 3/2003 | Hajianpour |
| 2003/0069582 A1 | 4/2003 | Culbert |
| 2003/0069645 A1 | 4/2003 | Ball et al. |
| 2003/0083660 A1 | 5/2003 | Orbay |
| 2003/0083662 A1 | 5/2003 | Middleton |
| 2003/0093076 A1 | 5/2003 | Venturini et al. |
| 2003/0097132 A1 | 5/2003 | Padget et al. |
| 2003/0097133 A1 | 5/2003 | Green et al. |
| 2003/0105461 A1 | 6/2003 | Putnam |
| 2003/0109932 A1 | 6/2003 | Keynan |
| 2003/0120273 A1 | 6/2003 | Cole |
| 2003/0130660 A1 | 7/2003 | Levy et al. |
| 2003/0153918 A1 | 8/2003 | Putnam et al. |
| 2003/0187449 A1 | 10/2003 | McCleary et al. |
| 2003/0216738 A1 | 11/2003 | Azar |
| 2003/0220641 A1 | 11/2003 | Thelen et al. |
| 2003/0220644 A1 | 11/2003 | Thelen et al. |
| 2003/0220646 A1 | 11/2003 | Thelen et al. |
| 2003/0220698 A1 | 11/2003 | Mears et al. |
| 2003/0225407 A1 | 12/2003 | Estrada |
| 2004/0039384 A1 | 2/2004 | Boehm et al. |
| 2004/0044413 A1 | 3/2004 | Schulter |
| 2004/0049192 A1 | 3/2004 | Shimizu |
| 2004/0078082 A1 | 4/2004 | Lange |
| 2004/0087956 A1 | 5/2004 | Weikel et al. |
| 2004/0092946 A1 | 5/2004 | Bagga et al. |
| 2004/0102777 A1 | 5/2004 | Huebner |

(56) References Cited

U.S. PATENT DOCUMENTS

| | | |
|---|---|---|
| 2004/0102778 A1 | 5/2004 | Huebner et al. |
| 2004/0102788 A1 | 5/2004 | Huebner et al. |
| 2004/0106925 A1 | 6/2004 | Culbert |
| 2004/0138665 A1 | 7/2004 | Padget et al. |
| 2004/0143264 A1 | 7/2004 | McAfee |
| 2004/0153080 A1 | 8/2004 | Dong et al. |
| 2004/0153114 A1 | 8/2004 | Reiley et al. |
| 2004/0153115 A1 | 8/2004 | Reiley et al. |
| 2004/0167528 A1 | 8/2004 | Schantz |
| 2004/0167625 A1 | 8/2004 | Beyar et al. |
| 2004/0181221 A1 | 9/2004 | Huebner et al. |
| 2004/0193163 A1 | 9/2004 | Orbay |
| 2004/0193164 A1 | 9/2004 | Orbay |
| 2004/0193165 A1 | 9/2004 | Orbay |
| 2004/0193251 A1 | 9/2004 | Rudnick et al. |
| 2004/0193267 A1 | 9/2004 | Jones et al. |
| 2004/0208717 A1 | 10/2004 | Greenhalgh |
| 2004/0214311 A1 | 10/2004 | Levy |
| 2004/0220678 A1 | 11/2004 | Chow et al. |
| 2004/0230193 A1 | 11/2004 | Cheung et al. |
| 2004/0236327 A1 | 11/2004 | Paul et al. |
| 2004/0236328 A1 | 11/2004 | Paul et al. |
| 2004/0236339 A1 | 11/2004 | Pepper |
| 2004/0249375 A1 | 12/2004 | Agee et al. |
| 2004/0260289 A1 | 12/2004 | Padget et al. |
| 2004/0260297 A1 | 12/2004 | Padget et al. |
| 2004/0267269 A1 | 12/2004 | Middleton et al. |
| 2005/0010231 A1 | 1/2005 | Myers |
| 2005/0015129 A1 | 1/2005 | Mische |
| 2005/0015154 A1 | 1/2005 | Lindsey et al. |
| 2005/0033366 A1 | 2/2005 | Cole et al. |
| 2005/0043733 A1 | 2/2005 | Eisermann et al. |
| 2005/0065522 A1 | 3/2005 | Orbay |
| 2005/0065523 A1 | 3/2005 | Orbay |
| 2005/0065524 A1 | 3/2005 | Orbay |
| 2005/0065526 A1 | 3/2005 | Drew et al. |
| 2005/0070902 A1 | 3/2005 | Medoff |
| 2005/0085813 A1 | 4/2005 | Spitler et al. |
| 2005/0085818 A1 | 4/2005 | Huebner |
| 2005/0085824 A1 | 4/2005 | Castaneda |
| 2005/0085921 A1 | 4/2005 | Gupta et al. |
| 2005/0113836 A1 | 5/2005 | Lozier et al. |
| 2005/0113892 A1 | 5/2005 | Sproul |
| 2005/0119749 A1 | 6/2005 | Lange |
| 2005/0124972 A1 | 6/2005 | Mische et al. |
| 2005/0125066 A1 | 6/2005 | Mcafee |
| 2005/0131407 A1 | 6/2005 | Sicvol et al. |
| 2005/0143734 A1 | 6/2005 | Cachia et al. |
| 2005/0154331 A1 | 7/2005 | Christie et al. |
| 2005/0159749 A1* | 7/2005 | Levy et al. ............ 606/72 |
| 2005/0177172 A1 | 8/2005 | Acker et al. |
| 2005/0182399 A1 | 8/2005 | Levine |
| 2005/0197537 A1 | 9/2005 | Bonadio et al. |
| 2005/0209557 A1 | 9/2005 | Carroll et al. |
| 2005/0216000 A1 | 9/2005 | Colleran et al. |
| 2005/0216007 A1 | 9/2005 | Woll et al. |
| 2005/0228391 A1 | 10/2005 | Levy et al. |
| 2005/0234472 A1 | 10/2005 | Huebner |
| 2005/0240190 A1 | 10/2005 | Gall et al. |
| 2005/0240193 A1 | 10/2005 | Layne et al. |
| 2005/0245928 A1 | 11/2005 | Colleran et al. |
| 2005/0251142 A1 | 11/2005 | Hoffmann et al. |
| 2005/0261779 A1 | 11/2005 | Meyer |
| 2005/0267483 A1 | 12/2005 | Middleton |
| 2005/0273138 A1 | 12/2005 | To et al. |
| 2005/0277936 A1 | 12/2005 | Siravo et al. |
| 2005/0277978 A1 | 12/2005 | Greenhalgh |
| 2005/0283154 A1 | 12/2005 | Orbay et al. |
| 2005/0283159 A1 | 12/2005 | Amara |
| 2005/0288676 A1 | 12/2005 | Schnieders et al. |
| 2006/0004362 A1 | 1/2006 | Patterson et al. |
| 2006/0004462 A1 | 1/2006 | Gupta |
| 2006/0009771 A1 | 1/2006 | Orbay et al. |
| 2006/0015123 A1 | 1/2006 | Fencl et al. |
| 2006/0036240 A1 | 2/2006 | Colleran et al. |
| 2006/0036244 A1 | 2/2006 | Spitler et al. |
| 2006/0047787 A1 | 3/2006 | Agarwal et al. |
| 2006/0052788 A1 | 3/2006 | Thelen et al. |
| 2006/0058621 A1 | 3/2006 | Wehrli et al. |
| 2006/0058826 A1 | 3/2006 | Evans et al. |
| 2006/0064005 A1 | 3/2006 | Triano et al. |
| 2006/0064106 A1 | 3/2006 | Fernandez |
| 2006/0064164 A1 | 3/2006 | Thelen et al. |
| 2006/0064173 A1 | 3/2006 | Guederian et al. |
| 2006/0069392 A1 | 3/2006 | Renzi Brivio et al. |
| 2006/0079894 A1 | 4/2006 | Colleran et al. |
| 2006/0079905 A1 | 4/2006 | Beyar et al. |
| 2006/0085009 A1 | 4/2006 | Truckai et al. |
| 2006/0089647 A1 | 4/2006 | Culbert et al. |
| 2006/0089648 A1 | 4/2006 | Masini |
| 2006/0100631 A1 | 5/2006 | Sullivan et al. |
| 2006/0100706 A1 | 5/2006 | Shadduck et al. |
| 2006/0106390 A1 | 5/2006 | Jensen et al. |
| 2006/0106394 A1 | 5/2006 | Colleran |
| 2006/0116773 A1 | 6/2006 | Cooney et al. |
| 2006/0122600 A1 | 6/2006 | Cole |
| 2006/0122610 A1 | 6/2006 | Culbert et al. |
| 2006/0142858 A1 | 6/2006 | Colleran et al. |
| 2006/0149281 A1 | 7/2006 | Reiley et al. |
| 2006/0149379 A1 | 7/2006 | Kuslich et al. |
| 2006/0155289 A1 | 7/2006 | Windhager et al. |
| 2006/0173454 A1 | 8/2006 | Spitler et al. |
| 2006/0178737 A1 | 8/2006 | Furcht et al. |
| 2006/0187748 A1 | 8/2006 | Kozyuk |
| 2006/0189994 A1 | 8/2006 | Wolford et al. |
| 2006/0195103 A1* | 8/2006 | Padget et al. ............ 606/72 |
| 2006/0200061 A1 | 9/2006 | Warkentine |
| 2006/0200140 A1 | 9/2006 | Lange |
| 2006/0200143 A1 | 9/2006 | Warburton |
| 2006/0217730 A1 | 9/2006 | Termanini |
| 2006/0229602 A1 | 10/2006 | Olsen |
| 2006/0241629 A1 | 10/2006 | Krebs et al. |
| 2006/0241630 A1 | 10/2006 | Brunnett et al. |
| 2006/0241671 A1 | 10/2006 | Greenhalgh |
| 2006/0241776 A1 | 10/2006 | Brown et al. |
| 2006/0247637 A1 | 11/2006 | Colleran et al. |
| 2006/0264944 A1 | 11/2006 | Cole |
| 2006/0264945 A1* | 11/2006 | Edidin et al. ............ 606/63 |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0271053 A1 | 11/2006 | Schlapfer et al. |
| 2006/0271061 A1 | 11/2006 | Beyar et al. |
| 2006/0271198 A1 | 11/2006 | Mcafee |
| 2006/0276797 A1 | 12/2006 | Botimer |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016211 A1 | 1/2007 | Botimer |
| 2007/0016283 A1 | 1/2007 | Greenhalgh et al. |
| 2007/0016300 A1 | 1/2007 | Kuslich |
| 2007/0027230 A1 | 2/2007 | Beyar et al. |
| 2007/0032567 A1 | 2/2007 | Beyar et al. |
| 2007/0043373 A1 | 2/2007 | Sala et al. |
| 2007/0049936 A1 | 3/2007 | Colleran et al. |
| 2007/0055379 A1 | 3/2007 | Stone et al. |
| 2007/0066480 A1 | 3/2007 | Moser et al. |
| 2007/0073342 A1 | 3/2007 | Stone et al. |
| 2007/0100285 A1 | 5/2007 | Griffin et al. |
| 2007/0112427 A1 | 5/2007 | Christy et al. |
| 2007/0118132 A1 | 5/2007 | Culbert et al. |
| 2007/0123876 A1 | 5/2007 | Czartoski et al. |
| 2007/0123877 A1 | 5/2007 | Goldin et al. |
| 2007/0123886 A1 | 5/2007 | Meyer et al. |
| 2007/0123936 A1 | 5/2007 | Goldin et al. |
| 2007/0123995 A1 | 5/2007 | Thelen et al. |
| 2007/0129746 A1 | 6/2007 | Mische |
| 2007/0142919 A1 | 6/2007 | Cooney et al. |
| 2007/0173745 A1 | 7/2007 | Diederich et al. |
| 2007/0173835 A1 | 7/2007 | Medoff et al. |
| 2007/0173839 A1 | 7/2007 | Running et al. |
| 2007/0173939 A1 | 7/2007 | Kim et al. |
| 2007/0179505 A1 | 8/2007 | Culbert |
| 2007/0198043 A1 | 8/2007 | Cox et al. |

(56) References Cited

U.S. PATENT DOCUMENTS

| | | |
|---|---|---|
| 2007/0213727 A1 | 9/2007 | Bottlang et al. |
| 2007/0219634 A1 | 9/2007 | Greenhalgh et al. |
| 2007/0225568 A1 | 9/2007 | Colleran |
| 2007/0225721 A1 | 9/2007 | Thelen et al. |
| 2007/0225726 A1 | 9/2007 | Dye et al. |
| 2007/0225810 A1 | 9/2007 | Colleran et al. |
| 2007/0233091 A1 | 10/2007 | Naifeh et al. |
| 2007/0233105 A1* | 10/2007 | Nelson et al. .................. 606/64 |
| 2007/0244485 A1 | 10/2007 | Greenhalgh et al. |
| 2007/0255287 A1 | 11/2007 | Rabiner |
| 2007/0270855 A1 | 11/2007 | Partin et al. |
| 2007/0276392 A1 | 11/2007 | Beyar et al. |
| 2007/0276405 A1 | 11/2007 | Huebner et al. |
| 2007/0282443 A1 | 12/2007 | Globerman et al. |
| 2007/0283849 A1 | 12/2007 | Edidin et al. |
| 2007/0288097 A1 | 12/2007 | Hurowitz |
| 2008/0009868 A1* | 1/2008 | Gotfried et al. ................ 606/63 |
| 2008/0009874 A1 | 1/2008 | Meridew et al. |
| 2008/0015601 A1 | 1/2008 | Castro et al. |
| 2008/0019970 A1 | 1/2008 | Gorman |
| 2008/0021474 A1* | 1/2008 | Bonutti et al. .................. 606/64 |
| 2008/0039854 A1 | 2/2008 | Rabiner |
| 2008/0041629 A1 | 2/2008 | Aronstam et al. |
| 2008/0053575 A1 | 3/2008 | Cheung et al. |
| 2008/0058804 A1 | 3/2008 | Lechot et al. |
| 2008/0065072 A1 | 3/2008 | Spitler et al. |
| 2008/0065073 A1 | 3/2008 | Perriello et al. |
| 2008/0065074 A1 | 3/2008 | Yeung et al. |
| 2008/0065140 A1 | 3/2008 | Bonutti |
| 2008/0071356 A1 | 3/2008 | Greenhalgh et al. |
| 2008/0077117 A1 | 3/2008 | Miller et al. |
| 2008/0077172 A1 | 3/2008 | Miller et al. |
| 2008/0077174 A1 | 3/2008 | Mische |
| 2008/0086133 A1 | 4/2008 | Kuslich et al. |
| 2008/0097332 A1 | 4/2008 | Greenhalgh et al. |
| 2008/0103501 A1 | 5/2008 | Ralph et al. |
| 2008/0103519 A1 | 5/2008 | Bonutti |
| 2008/0108996 A1 | 5/2008 | Padget et al. |
| 2008/0114364 A1 | 5/2008 | Goldin et al. |
| 2008/0119886 A1 | 5/2008 | Greenhalgh et al. |
| 2008/0125784 A1 | 5/2008 | Rabiner et al. |
| 2008/0125805 A1 | 5/2008 | Mische |
| 2008/0132896 A1 | 6/2008 | Bowen et al. |
| 2008/0133017 A1 | 6/2008 | Beyar et al. |
| 2008/0140078 A1 | 6/2008 | Nelson et al. |
| 2008/0140130 A1 | 6/2008 | Chan et al. |
| 2008/0149115 A1 | 6/2008 | Hauck et al. |
| 2008/0161805 A1 | 7/2008 | Saravia et al. |
| 2008/0161825 A1 | 7/2008 | Greenhalgh et al. |
| 2008/0167657 A1 | 7/2008 | Greenhalgh |
| 2008/0177261 A1 | 7/2008 | McMinn |
| 2008/0183171 A1 | 7/2008 | Elghazaly et al. |
| 2008/0194868 A1 | 8/2008 | Kozyuk |
| 2008/0195104 A1 | 8/2008 | Sidebotham et al. |
| 2008/0195105 A1 | 8/2008 | Sidebotham et al. |
| 2008/0200915 A1 | 8/2008 | Globerman et al. |
| 2008/0200951 A1 | 8/2008 | Mcafee |
| 2008/0208202 A1 | 8/2008 | Williams |
| 2008/0208261 A1 | 8/2008 | Medoff |
| 2008/0208320 A1 | 8/2008 | Tan-Malecki et al. |
| 2008/0212405 A1 | 9/2008 | Globerman et al. |
| 2008/0228192 A1 | 9/2008 | Beyar et al. |
| 2008/0249436 A1 | 10/2008 | Darr |
| 2008/0255560 A1 | 10/2008 | Myers et al. |
| 2008/0262495 A1 | 10/2008 | Coati et al. |
| 2008/0269742 A1 | 10/2008 | Levy et al. |
| 2008/0269745 A1 | 10/2008 | Justin |
| 2008/0269746 A1 | 10/2008 | Justin |
| 2008/0269747 A1 | 10/2008 | Justin |
| 2008/0269748 A1 | 10/2008 | Justin et al. |
| 2008/0269749 A1 | 10/2008 | Shalaby et al. |
| 2008/0269750 A1 | 10/2008 | Justin |
| 2008/0269776 A1 | 10/2008 | Justin et al. |
| 2008/0275448 A1 | 11/2008 | Sackett et al. |
| 2008/0275449 A1 | 11/2008 | Sackett et al. |
| 2008/0287950 A1 | 11/2008 | Frigg et al. |
| 2008/0287951 A1 | 11/2008 | Stoneburner et al. |
| 2008/0294163 A1 | 11/2008 | Chou et al. |
| 2008/0294166 A1 | 11/2008 | Goldin et al. |
| 2008/0294167 A1 | 11/2008 | Schumacher et al. |
| 2008/0294169 A1 | 11/2008 | Scott et al. |
| 2008/0294205 A1 | 11/2008 | Greenhalgh et al. |
| 2008/0319444 A9 | 12/2008 | Osorio et al. |
| 2009/0005782 A1 | 1/2009 | Chirico et al. |
| 2009/0012522 A1 | 1/2009 | Lob |
| 2009/0018542 A1 | 1/2009 | Saravia et al. |
| 2009/0018656 A1 | 1/2009 | Clifford et al. |
| 2009/0018666 A1 | 1/2009 | Grundei et al. |
| 2009/0024204 A1 | 1/2009 | Greenhalgh et al. |
| 2009/0048620 A1 | 2/2009 | Weiss et al. |
| 2009/0048629 A1 | 2/2009 | Rabiner |
| 2009/0048672 A1* | 2/2009 | Essenmacher ............. 623/11.11 |
| 2009/0054900 A1 | 2/2009 | Rabiner et al. |
| 2009/0076517 A1 | 3/2009 | Reiley et al. |
| 2009/0088752 A1 | 4/2009 | Metzinger et al. |
| 2009/0104586 A1 | 4/2009 | Cardoso et al. |
| 2009/0112196 A1 | 4/2009 | Rabiner et al. |
| 2009/0112330 A1 | 4/2009 | Grundei |
| 2009/0125028 A1 | 5/2009 | Teisen et al. |
| 2009/0131992 A1 | 5/2009 | Greenhalgh et al. |
| 2009/0143781 A1 | 6/2009 | Mische |
| 2009/0143827 A1 | 6/2009 | Levy et al. |
| 2009/0149890 A1 | 6/2009 | Martin |
| 2009/0149956 A1 | 6/2009 | Greenhalgh et al. |
| 2009/0157080 A1 | 6/2009 | Warburton |
| 2009/0163918 A1 | 6/2009 | Levy et al. |
| 2009/0177206 A1 | 7/2009 | Lozier et al. |
| 2009/0177239 A1 | 7/2009 | Castro |
| 2009/0182336 A1* | 7/2009 | Brenzel et al. .................. 606/62 |
| 2009/0216232 A1 | 8/2009 | Buford et al. |
| 2009/0228007 A1 | 9/2009 | Justin et al. |
| 2009/0228008 A1 | 9/2009 | Justin et al. |
| 2009/0281628 A1 | 11/2009 | Oglaza |
| 2009/0292323 A1 | 11/2009 | Chirico et al. |
| 2009/0318981 A1 | 12/2009 | Kang |
| 2010/0023010 A1 | 1/2010 | Nelson et al. |
| 2010/0087821 A1 | 4/2010 | Trip et al. |
| 2010/0094292 A1 | 4/2010 | Parrott |
| 2010/0094347 A1 | 4/2010 | Nelson et al. |
| 2010/0114181 A1 | 5/2010 | Lob |
| 2010/0131019 A1 | 5/2010 | Lob |
| 2010/0145397 A1 | 6/2010 | Overes et al. |
| 2010/0161061 A1 | 6/2010 | Hunt |
| 2010/0222884 A1 | 9/2010 | Greenhalgh |
| 2010/0241120 A1 | 9/2010 | Bledsoe et al. |
| 2010/0241123 A1 | 9/2010 | Middleton et al. |
| 2010/0241176 A1 | 9/2010 | Lob |
| 2010/0286481 A1 | 11/2010 | Sharp et al. |
| 2010/0286692 A1* | 11/2010 | Greenhalgh et al. ............. 606/63 |
| 2011/0077650 A1 | 3/2011 | Braun et al. |
| 2011/0087227 A1 | 4/2011 | Mazur et al. |
| 2011/0137313 A1 | 6/2011 | Jensen et al. |
| 2011/0144645 A1 | 6/2011 | Saravia et al. |
| 2011/0178520 A1 | 7/2011 | Taylor et al. |
| 2011/0190832 A1 | 8/2011 | Taylor et al. |
| 2011/0218585 A1 | 9/2011 | Krinke et al. |
| 2011/0282346 A1 | 11/2011 | Pham et al. |
| 2011/0295255 A1 | 12/2011 | Roberts et al. |
| 2011/0306975 A1* | 12/2011 | Kaikkonen et al. ............. 606/63 |
| 2012/0065638 A1 | 3/2012 | Moore |
| 2012/0232533 A1 | 9/2012 | Veldman et al. |
| 2012/0239038 A1 | 9/2012 | Saravia et al. |
| 2012/0253410 A1 | 10/2012 | Taylor et al. |
| 2013/0006245 A1 | 1/2013 | Stoneburner et al. |
| 2013/0012942 A1 | 1/2013 | Nelson et al. |
| 2013/0116693 A1 | 5/2013 | Nelson et al. |
| 2013/0231665 A1 | 9/2013 | Saravia et al. |
| 2014/0031823 A1 | 1/2014 | Mazur et al. |
| 2014/0074093 A9 | 3/2014 | Nelson et al. |

FOREIGN PATENT DOCUMENTS

| | | |
|---|---|---|
| AU | 2007323566 A1 | 6/2009 |
| AU | 2007323567 A1 | 6/2009 |

(56) References Cited

FOREIGN PATENT DOCUMENTS

| | | |
|---|---|---|
| AU | 2007323570 A1 | 6/2009 |
| AU | 2009257472 A1 | 1/2011 |
| AU | 2009296243 A1 | 4/2011 |
| CA | 2007210 A1 | 11/1990 |
| CA | 2452508 A1 | 1/2003 |
| CA | 2609175 A1 | 12/2005 |
| CA | 2608693 A1 | 11/2006 |
| CA | 2669737 A1 | 5/2008 |
| CA | 2670263 A1 | 5/2008 |
| CA | 2670438 A1 | 5/2008 |
| CA | 2678911 A1 | 9/2008 |
| CA | 2685046 A1 | 11/2008 |
| CA | 2727453 A1 | 12/2009 |
| CA | 2738478 A1 | 4/2010 |
| CN | 1533260 A | 9/2004 |
| CN | 2699849 Y | 5/2005 |
| CN | 1909848 A | 2/2007 |
| CN | 101208053 A | 6/2008 |
| CN | 101636119 A | 1/2010 |
| DE | 3146065 A1 | 5/1983 |
| DE | 3234875 A1 | 3/1984 |
| DE | 198800197 U1 | 8/1988 |
| DE | 3922044 A1 | 2/1991 |
| DE | 202006017194 U1 | 2/2007 |
| DE | 102006016213 A1 | 10/2007 |
| EP | 145166 A2 | 6/1985 |
| EP | 0145166 A2 | 6/1985 |
| EP | 145166 A3 | 8/1986 |
| EP | 253526 A1 | 1/1988 |
| EP | 263292 A1 | 4/1988 |
| EP | 275871 A1 | 7/1988 |
| EP | 355035 A2 | 2/1990 |
| EP | 381462 A2 | 8/1990 |
| EP | 396519 A1 | 11/1990 |
| EP | 401650 A1 | 12/1990 |
| EP | 409769 A1 | 1/1991 |
| EP | 420542 A1 | 4/1991 |
| EP | 440371 A1 | 8/1991 |
| EP | 442137 A1 | 8/1991 |
| EP | 475077 A2 | 3/1992 |
| EP | 487669 A1 | 6/1992 |
| EP | 491211 A1 | 6/1992 |
| EP | 508710 A1 | 10/1992 |
| EP | 525352 A1 | 2/1993 |
| EP | 611560 A1 | 8/1994 |
| EP | 745352 A2 | 12/1996 |
| EP | 546162 B1 | 9/1997 |
| EP | 807419 A2 | 11/1997 |
| EP | 819413 A2 | 1/1998 |
| EP | 931513 A2 | 7/1999 |
| EP | 0941037 B1 | 9/1999 |
| EP | 1099412 A2 | 5/2001 |
| EP | 1132051 A2 | 9/2001 |
| EP | 674495 B1 | 11/2001 |
| EP | 1155661 A1 | 11/2001 |
| EP | 1203569 A1 | 5/2002 |
| EP | 900065 B1 | 6/2002 |
| EP | 1277442 A2 | 1/2003 |
| EP | 1300122 A2 | 4/2003 |
| EP | 1348384 A2 | 10/2003 |
| EP | 1372496 A1 | 1/2004 |
| EP | 1391186 A1 | 2/2004 |
| EP | 1098600 B1 | 3/2004 |
| EP | 1277442 A3 | 3/2004 |
| EP | 1396231 A1 | 3/2004 |
| EP | 1410765 A2 | 4/2004 |
| EP | 1442718 A1 | 8/2004 |
| EP | 1442729 A1 | 8/2004 |
| EP | 1454592 A2 | 9/2004 |
| EP | 1459686 A2 | 9/2004 |
| EP | 1484077 A2 | 12/2004 |
| EP | 1079752 B1 | 1/2005 |
| EP | 1484077 A3 | 1/2005 |
| EP | 1495729 A1 | 1/2005 |
| EP | 1148825 B1 | 3/2005 |
| EP | 1148850 B1 | 4/2005 |
| EP | 1522268 A1 | 4/2005 |
| EP | 1227765 B1 | 5/2005 |
| EP | 1535579 A2 | 6/2005 |
| EP | 1563795 A1 | 8/2005 |
| EP | 1582159 A1 | 10/2005 |
| EP | 1582160 A1 | 10/2005 |
| EP | 1582161 A1 | 10/2005 |
| EP | 1582162 A1 | 10/2005 |
| EP | 1582163 A1 | 10/2005 |
| EP | 1582164 A1 | 10/2005 |
| EP | 1634548 A2 | 3/2006 |
| EP | 1639953 A1 | 3/2006 |
| EP | 1669035 A1 | 6/2006 |
| EP | 1454592 A3 | 8/2006 |
| EP | 1700572 A1 | 9/2006 |
| EP | 1702572 A2 | 9/2006 |
| EP | 1714618 A2 | 10/2006 |
| EP | 1787593 A1 | 5/2007 |
| EP | 1808143 A1 | 7/2007 |
| EP | 1815813 A2 | 8/2007 |
| EP | 1820462 A1 | 8/2007 |
| EP | 1011464 B1 | 1/2008 |
| EP | 1885263 A1 | 2/2008 |
| EP | 1905367 A1 | 4/2008 |
| EP | 1905392 A1 | 4/2008 |
| EP | 1915959 A2 | 4/2008 |
| EP | 1920721 A2 | 5/2008 |
| EP | 1923019 A1 | 5/2008 |
| EP | 1277442 B1 | 7/2008 |
| EP | 1972308 A1 | 9/2008 |
| EP | 1987785 A2 | 11/2008 |
| EP | 2025292 A1 | 2/2009 |
| EP | 1459689 B1 | 4/2009 |
| EP | 1484077 B1 | 6/2009 |
| EP | 1073371 B2 | 7/2009 |
| EP | 2094163 A2 | 9/2009 |
| EP | 2094177 A2 | 9/2009 |
| EP | 1459689 B3 | 11/2009 |
| EP | 2129309 A2 | 12/2009 |
| EP | 2299917 A1 | 3/2011 |
| EP | 2309937 A2 | 4/2011 |
| EP | 2341857 A2 | 7/2011 |
| FR | 2653006 A1 | 4/1991 |
| GB | 2173565 A | 10/1986 |
| GB | 2268068 A | 1/1994 |
| GB | 2274993 | 8/1994 |
| JP | 1310664 A | 12/1989 |
| JP | 2000287983 | 10/2000 |
| JP | 2008500140 A | 1/2008 |
| JP | 2008540037 A | 11/2008 |
| JP | 2010510040 A | 4/2010 |
| JP | 2010510041 A | 4/2010 |
| JP | 2010510042 A | 4/2010 |
| JP | 2010522046 A | 7/2010 |
| JP | 2010524642 A | 7/2010 |
| JP | 2011523889 A | 8/2011 |
| JP | 2012504027 A | 2/2012 |
| RU | 2004104359 A | 2/2005 |
| WO | WO8904150 A1 | 5/1989 |
| WO | WO8907056 A1 | 8/1989 |
| WO | WO9003764 A1 | 4/1990 |
| WO | WO9011726 A1 | 10/1990 |
| WO | WO9102493 A1 | 3/1991 |
| WO | WO9106260 A1 | 5/1991 |
| WO | WO9106265 A1 | 5/1991 |
| WO | WO9111962 A1 | 8/1991 |
| WO | WO9119461 A1 | 12/1991 |
| WO | WO9424938 A1 | 11/1994 |
| WO | WO9427507 A1 | 12/1994 |
| WO | WO9428824 A2 | 12/1994 |
| WO | WO9514433 A1 | 6/1995 |
| WO | WO9514433 A1 | 6/1995 |
| WO | WO9520362 A1 | 8/1995 |
| WO | WO9531159 A1 | 11/1995 |
| WO | WO9602202 A1 | 2/1996 |
| WO | WO9602203 A1 | 2/1996 |
| WO | WO9605783 A1 | 2/1996 |
| WO | WO9606041 A1 | 2/1996 |

(56) References Cited

FOREIGN PATENT DOCUMENTS

| | | |
|---|---|---|
| WO | WO9607161 A1 | 3/1996 |
| WO | WO9616607 A1 | 6/1996 |
| WO | WO9617557 A1 | 6/1996 |
| WO | WO9618354 A2 | 6/1996 |
| WO | WO9618354 A2 | 6/1996 |
| WO | WO9618354 A3 | 8/1996 |
| WO | WO9625118 A1 | 8/1996 |
| WO | WO9640476 A1 | 12/1996 |
| WO | WO9703611 A1 | 2/1997 |
| WO | WO9703611 A1 | 2/1997 |
| WO | WO9718775 A1 | 5/1997 |
| WO | WO9742602 A1 | 11/1997 |
| WO | WO9742912 A1 | 11/1997 |
| WO | WO9747251 A1 | 12/1997 |
| WO | WO9801077 A1 | 1/1998 |
| WO | WO9805261 A2 | 2/1998 |
| WO | WO9807392 A1 | 2/1998 |
| WO | WO9819616 A1 | 5/1998 |
| WO | WO9824380 A1 | 6/1998 |
| WO | WO9826725 A1 | 6/1998 |
| WO | WO9838918 A1 | 9/1998 |
| WO | WO9846169 A1 | 10/1998 |
| WO | WO9856301 A1 | 12/1998 |
| WO | WO9922661 A1 | 5/1999 |
| WO | WO9922662 A1 | 5/1999 |
| WO | WO9937219 A1 | 7/1999 |
| WO | WO9947055 A1 | 9/1999 |
| WO | WO9951149 A1 | 10/1999 |
| WO | WO9953843 A1 | 10/1999 |
| WO | WO9955248 A1 | 11/1999 |
| WO | WO9962416 A1 | 12/1999 |
| WO | WO0006037 A1 | 2/2000 |
| WO | WO0009024 A1 | 2/2000 |
| WO | WO0012036 A1 | 3/2000 |
| WO | WO0012036 A1 | 3/2000 |
| WO | WO0021455 A1 | 4/2000 |
| WO | WO0025681 A1 | 5/2000 |
| WO | WO0028906 A1 | 5/2000 |
| WO | WO0030551 A1 | 6/2000 |
| WO | WO0030569 A1 | 6/2000 |
| WO | WO0038586 A1 | 7/2000 |
| WO | WO0042954 A2 | 7/2000 |
| WO | WO0044319 A1 | 8/2000 |
| WO | WO0044321 A2 | 8/2000 |
| WO | WO0044946 A1 | 8/2000 |
| WO | WO0045712 A1 | 8/2000 |
| WO | WO0045714 A1 | 8/2000 |
| WO | WO0045715 A1 | 8/2000 |
| WO | WO0045722 A1 | 8/2000 |
| WO | WO0047119 A1 | 8/2000 |
| WO | WO0048534 A1 | 8/2000 |
| WO | WO0071038 A1 | 11/2000 |
| WO | WO0076414 A1 | 12/2000 |
| WO | WO0108571 A1 | 2/2001 |
| WO | WO0128443 A1 | 4/2001 |
| WO | WO0134045 A1 | 5/2001 |
| WO | WO0149193 A1 | 7/2001 |
| WO | WO0154598 A1 | 8/2001 |
| WO | WO0160268 A1 | 8/2001 |
| WO | WO0160268 A1 | 8/2001 |
| WO | WO0176493 A1 | 10/2001 |
| WO | WO0176514 A2 | 10/2001 |
| WO | WO0178015 A2 | 10/2001 |
| WO | WO0180751 A1 | 11/2001 |
| WO | WO0185042 A1 | 11/2001 |
| WO | WO0213700 A2 | 2/2002 |
| WO | WO0213716 A1 | 2/2002 |
| WO | WO0217794 A1 | 3/2002 |
| WO | WO0217794 A1 | 3/2002 |
| WO | WO0224088 A2 | 3/2002 |
| WO | WO0234107 A2 | 5/2002 |
| WO | WO0234148 A2 | 5/2002 |
| WO | WO0237935 A2 | 5/2002 |
| WO | WO0245606 A1 | 6/2002 |
| WO | WO0249517 A1 | 6/2002 |
| WO | WO02058575 A1 | 8/2002 |
| WO | WO02067824 A2 | 9/2002 |
| WO | WO02078555 A1 | 10/2002 |
| WO | WO02089683 A1 | 11/2002 |
| WO | WO0296306 A1 | 12/2002 |
| WO | WO03007830 A1 | 1/2003 |
| WO | WO03013336 A2 | 2/2003 |
| WO | WO0217794 A8 | 3/2003 |
| WO | WO03030760 A1 | 4/2003 |
| WO | WO03043488 A2 | 5/2003 |
| WO | WO03045257 A2 | 6/2003 |
| WO | WO03047440 A2 | 6/2003 |
| WO | WO03068090 A1 | 8/2003 |
| WO | WO0217794 A9 | 9/2003 |
| WO | WO2004008949 A2 | 1/2004 |
| WO | WO2004017817 A2 | 3/2004 |
| WO | WO2004030549 A1 | 4/2004 |
| WO | WO2004064603 A2 | 8/2004 |
| WO | WO2004078220 A2 | 9/2004 |
| WO | WO2004078221 A2 | 9/2004 |
| WO | WO2004086934 A2 | 10/2004 |
| WO | WO2004092431 A1 | 10/2004 |
| WO | WO2004093633 A2 | 11/2004 |
| WO | WO2004098453 A2 | 11/2004 |
| WO | WO2004103209 A2 | 12/2004 |
| WO | WO2004110292 A2 | 12/2004 |
| WO | WO2004110300 A2 | 12/2004 |
| WO | WO2004112661 A1 | 12/2004 |
| WO | WO2005000159 A2 | 1/2005 |
| WO | WO2005020830 A1 | 3/2005 |
| WO | WO2005020833 A2 | 3/2005 |
| WO | WO2005023085 A2 | 3/2005 |
| WO | WO2005032326 A2 | 4/2005 |
| WO | WO2005032340 A2 | 4/2005 |
| WO | WO2005039651 A2 | 5/2005 |
| WO | WO2005041799 A1 | 5/2005 |
| WO | WO2005044122 A1 | 5/2005 |
| WO | WO2005051971 A1 | 6/2005 |
| WO | WO2005055874 A2 | 6/2005 |
| WO | WO2005020833 A3 | 7/2005 |
| WO | WO2005070314 A1 | 8/2005 |
| WO | WO2005092223 A2 | 10/2005 |
| WO | WO2005094693 A1 | 10/2005 |
| WO | WO2005094705 A2 | 10/2005 |
| WO | WO2005094706 A1 | 10/2005 |
| WO | WO2005096975 A2 | 10/2005 |
| WO | WO2005102196 A1 | 11/2005 |
| WO | WO2005107415 A2 | 11/2005 |
| WO | WO2005112804 A1 | 12/2005 |
| WO | WO2005112804 A1 | 12/2005 |
| WO | WO2005122931 A1 | 12/2005 |
| WO | WO2005122932 A2 | 12/2005 |
| WO | WO2005123171 A2 | 12/2005 |
| WO | WO2006011152 A2 | 2/2006 |
| WO | WO2006020530 A2 | 2/2006 |
| WO | WO2005112804 A9 | 3/2006 |
| WO | WO2006023793 A2 | 3/2006 |
| WO | WO2006026323 A2 | 3/2006 |
| WO | WO2006026323 A2 | 3/2006 |
| WO | WO2006026323 A9 | 4/2006 |
| WO | WO2006041460 A1 | 4/2006 |
| WO | WO2006041460 A1 | 4/2006 |
| WO | WO2006042188 A2 | 4/2006 |
| WO | WO2006042189 A2 | 4/2006 |
| WO | WO2006042334 A2 | 4/2006 |
| WO | WO2006034396 A3 | 5/2006 |
| WO | WO2006051547 A2 | 5/2006 |
| WO | WO2006055448 A1 | 5/2006 |
| WO | WO2006063083 A1 | 6/2006 |
| WO | WO2006066228 A2 | 6/2006 |
| WO | WO2006068682 A1 | 6/2006 |
| WO | WO2010065855 A1 | 6/2006 |
| WO | 1073371 B1 | 8/2006 |
| WO | WO2006089929 A1 | 8/2006 |
| WO | WO2006090379 A2 | 8/2006 |
| WO | WO2006034436 A3 | 10/2006 |
| WO | WO2006108067 A2 | 10/2006 |
| WO | WO2006113800 A2 | 10/2006 |
| WO | WO2006116760 A2 | 11/2006 |

(56) References Cited

FOREIGN PATENT DOCUMENTS

| | | |
|---|---|---|
| WO | WO2006116761 A2 | 11/2006 |
| WO | WO2006124764 A1 | 11/2006 |
| WO | WO2006124764 A1 | 11/2006 |
| WO | WO2006124937 A2 | 11/2006 |
| WO | WO2006127904 A1 | 11/2006 |
| WO | WO2006127904 A1 | 11/2006 |
| WO | WO2007002933 A2 | 1/2007 |
| WO | WO2007008177 A1 | 1/2007 |
| WO | WO2007009107 A2 | 1/2007 |
| WO | WO2007009123 A2 | 1/2007 |
| WO | WO2007011994 A2 | 1/2007 |
| WO | WO2007012046 A2 | 1/2007 |
| WO | WO2007025236 A2 | 3/2007 |
| WO | WO2007040949 A2 | 4/2007 |
| WO | WO2007041665 A2 | 4/2007 |
| WO | WO2006124937 A3 | 5/2007 |
| WO | WO2007053960 A1 | 5/2007 |
| WO | WO2007058943 A2 | 5/2007 |
| WO | WO2007059243 A1 | 5/2007 |
| WO | WO2007059243 A1 | 5/2007 |
| WO | WO2007059246 A1 | 5/2007 |
| WO | WO2007059259 A1 | 5/2007 |
| WO | WO2007059259 A1 | 5/2007 |
| WO | WO2007065137 A2 | 6/2007 |
| WO | WO2007069251 A2 | 6/2007 |
| WO | WO2007073488 A2 | 6/2007 |
| WO | WO2007076308 A2 | 7/2007 |
| WO | WO2007076374 A2 | 7/2007 |
| WO | WO2007076376 A2 | 7/2007 |
| WO | WO2007076377 A2 | 7/2007 |
| WO | WO2007078692 A2 | 7/2007 |
| WO | WO2007079237 A2 | 7/2007 |
| WO | WO2007082151 A2 | 7/2007 |
| WO | WO2007084239 A2 | 7/2007 |
| WO | WO2007092813 A2 | 8/2007 |
| WO | WO2007092813 A2 | 8/2007 |
| WO | WO2007092841 A2 | 8/2007 |
| WO | WO2007092841 A2 | 8/2007 |
| WO | WO2007036815 A2 | 9/2007 |
| WO | WO2007114982 A1 | 10/2007 |
| WO | WO2007115108 A1 | 10/2007 |
| WO | WO2007117571 A2 | 10/2007 |
| WO | WO2007120539 A2 | 10/2007 |
| WO | WO2007092841 A3 | 11/2007 |
| WO | WO2007124130 A2 | 11/2007 |
| WO | WO2007127255 A2 | 11/2007 |
| WO | WO2007127260 A2 | 11/2007 |
| WO | WO2007131002 A2 | 11/2007 |
| WO | WO2007134134 A2 | 11/2007 |
| WO | WO2007079237 A3 | 12/2007 |
| WO | WO2007145824 A2 | 12/2007 |
| WO | WO2008004229 A2 | 1/2008 |
| WO | WO2008006117 A2 | 1/2008 |
| WO | WO2008016910 A2 | 2/2008 |
| WO | WO2008019397 A2 | 2/2008 |
| WO | WO2008035849 A1 | 3/2008 |
| WO | WO2008037454 A1 | 4/2008 |
| WO | WO2008043254 A1 | 4/2008 |
| WO | WO2008058960 A2 | 5/2008 |
| WO | WO2008059027 A2 | 5/2008 |
| WO | WO2008060277 A2 | 5/2008 |
| WO | WO2008060277 A2 | 5/2008 |
| WO | WO2008063265 A1 | 5/2008 |
| WO | WO2008064346 A2 | 5/2008 |
| WO | WO2008064346 A3 | 5/2008 |
| WO | WO2008064347 A2 | 5/2008 |
| WO | WO2008064347 A2 | 5/2008 |
| WO | WO2008064347 A3 | 5/2008 |
| WO | WO2008064350 A2 | 5/2008 |
| WO | WO2008064350 A3 | 5/2008 |
| WO | WO2008076330 | 6/2008 |
| WO | WO2008076330 A1 | 6/2008 |
| WO | WO2008076357 A1 | 6/2008 |
| WO | WO2008094407 A1 | 8/2008 |
| WO | WO2007011353 A3 | 9/2008 |
| WO | WO2007092813 B3 | 9/2008 |
| WO | WO2008109566 A1 | 9/2008 |
| WO | WO2008112308 A1 | 9/2008 |
| WO | WO2008116170 A2 | 9/2008 |
| WO | WO2008116175 A2 | 9/2008 |
| WO | WO2008116175 A2 | 9/2008 |
| WO | WO2008118945 A1 | 10/2008 |
| WO | WO2008121608 A2 | 10/2008 |
| WO | WO2008132728 A1 | 11/2008 |
| WO | WO2008134287 A2 | 11/2008 |
| WO | WO2008134758 A1 | 11/2008 |
| WO | WO2008139456 A2 | 11/2008 |
| WO | WO2008144709 A2 | 11/2008 |
| WO | WO2008144709 A2 | 11/2008 |
| WO | WO2007078692 A3 | 12/2008 |
| WO | 2014261 A1 | 1/2009 |
| WO | WO2008121608 A3 | 1/2009 |
| WO | WO2008134287 A3 | 1/2009 |
| WO | WO2009006622 A2 | 1/2009 |
| WO | WO2009007331 A2 | 1/2009 |
| WO | WO2009009772 A1 | 1/2009 |
| WO | WO2009010412 A1 | 1/2009 |
| WO | WO2009012347 A1 | 1/2009 |
| WO | WO2009026070 A1 | 2/2009 |
| WO | WO2009027325 A1 | 3/2009 |
| WO | WO2009039430 A1 | 3/2009 |
| WO | WO2006026323 A3 | 4/2009 |
| WO | WO2006026397 A3 | 4/2009 |
| WO | WO2009045751 A1 | 4/2009 |
| WO | WO2009059227 A1 | 5/2009 |
| WO | WO2009072125 A1 | 6/2009 |
| WO | WO2009076086 A1 | 6/2009 |
| WO | WO2008144709 A3 | 7/2009 |
| WO | WO2009088376 A1 | 7/2009 |
| WO | WO2009094478 A1 | 7/2009 |
| WO | WO2008060277 A3 | 9/2009 |
| WO | WO2008112912 A3 | 9/2009 |
| WO | WO2009132333 A2 | 10/2009 |
| WO | WO2009143374 A2 | 11/2009 |
| WO | WO2009143496 A1 | 11/2009 |
| WO | WO2008112875 A3 | 12/2009 |
| WO | WO2009146457 A1 | 12/2009 |
| WO | WO2009152270 A1 | 12/2009 |
| WO | WO2009152272 A1 | 12/2009 |
| WO | WO2009152273 A1 | 12/2009 |
| WO | WO2009132333 A3 | 1/2010 |
| WO | WO2008139456 A3 | 2/2010 |
| WO | WO2010037038 A2 | 4/2010 |
| WO | WO2010037038 A3 | 4/2010 |
| WO | WO2010056895 A1 | 5/2010 |
| WO | WO2010062379 A1 | 6/2010 |
| WO | WO2010091242 A1 | 8/2010 |
| WO | WO20100035156 A1 | 11/2010 |

OTHER PUBLICATIONS

App No. PCT/US 09/30971 International Search Report.
App No. PCT/US 09/30971 Written Opinion of the International Searching Authority.
App No. PCT/US/2011/21074 International Search Report.
App No. PCT/US/2011/21074 Written Opinion of the International Searching Authority.
App No. PCT/US2011/021735 International Search Report.
App No. PCT/US2011/021735 Written Opinion of the International Searching Authority.
App No. PCT/US2011/027597 Written Opinion of the International Searching Authority.
App No. PCT/US2011/027602 International Search Report.
App No. PCT/US2011/027602 Written Opinion of the International Searching Authority.
US 7,063,700, 6/2006, Michelson (withdrawn).
US 7,201,752, 4/2007, Huebner et al. (withdrawn).
Putnam, Matthew D., et al., "Distal Radial Metaphyseal Forces in an Extrinsic Grip Model: Implications for Post fracture Rehabilitation," American Society for Surgery of the Hand, 25A: 469-475, May 2000.
Higgins, Thomas F., et al., "A Biomechanical Analysis of Fixation of Intra-Articular Distal Radial Fractures with Calcium-Phosphate

(56) References Cited

OTHER PUBLICATIONS

Bone Cement," The Journal of Bone and Joint Surgery, 84:1579-1586, Needham, Massachusetts, Sep. 2002.
Stoeckel et al., "Self-Expanding Nitinol Stents—Material and Design Considerations," Nitinol Devices & Components, Fremont, California, 2003.
Rozenthal, Tamara D., et al., "Functional Outcome and Complications After Volar Plating for Dorsally Displaced, Unstable Fractures of the Distal Radius," The Journal of Hand Surgery, 31A: 359-365, Mar. 2006.
Keast-Butler, Oliver, et al., "Biology Versus Mechanics in the Treatment of Distal Radial Fractures," The Journal of Orthopedic Trauma, 22: S91-S95, Philadelphia, Pennsylvania, Sep. 2008.
Mudgal, Chaitanya S., et al., "Plate Fixation of Osteoporotic Fractures of the Distal Radius," The Journal of Orthopedic Trauma, 22: S106-S115, 2008, Philadelphia, Pennsylvania, Sep. 2008.
Bogoch, Earl R., et al., "The Osteoporosis Needs of Patients with Wrist Fractures," The Journal of Orthopedic Trauma, vol. 22, No. 8, Supplement, Philadelphia, Pennsylvania, Sep. 2008.
Arora, Rohit, et al., "A Representative Case of Osteoporotic Distal Radius Fracture," The Journal of Orthopedic Trauma, vol. 22, No. 8, Supplement, Philadelphia, Pennsylvania, Sep. 2008.
Firoozabadi, Reza, et al., "Qualitative and Quantitative Assessment of Bone Fragility and Fracture Healing Using Conventional Radiography and Advanced Imaging Technologies—Focus on Wrist Fracture," The Journal of Orthopedic Trauma, vol. 22, No. 8, Supplement, Philadelphia, Pennsylvania, Sep. 2008.
Goldhan, Jorg, et al., "What Counts: Outcome Assessment After Distal Radius Fractures in Aged Patients," The Journal of Orthopedic Trauma, vol. 22, No. 8, Supplement, Philadelphia, Pennsylvania, Sep. 2008.
Hoang-Kim, Amy, et al., "Wrist Fractures in Osteoporotic Patients," The Journal of Orthopedic Trauma, vol. 22, No. 8, Supplement, Philadelphia, Pennsylvania, Sep. 2008.
Kettler, Mark, et al., "Do We Need to Include Osteoporosis in Today's Classification of Distal Radius Fractures?" The Journal of Orthopedic Trauma, vol. 22, No. 8, Supplement, Philadelphia, Pennsylvania, Sep. 2008.
Downing, Martin R., et al., "Assessment of Inducible Fracture Micromotion in Distal Radial Fractures Using Radiostereometry," The Journal of Orthopedic Trauma, vol. 22, No. 8, Supplement, Philadelphia, Pennsylvania, Sep. 2008.
Suhm, Norbert, et al., "Injectable Bone Cement Augmentation for the Treatment of Distal Radius Fractures: A Review," The Journal of Orthopedic Trauma, vol. 22, No. 8, Supplement, Philadelphia, Pennsylvania, Sep. 2008.
Van Lenthe, G. Harry, et al., "Quantification of Bone Structural Parameters and Mechanical Competence at the Distal Radius," The Journal of Orthopedic Trauma, vol. 22, No. 8, Supplement, Philadelphia, Pennsylvania, Sep. 2008.
Parkinson, Ian H., et al., "Whole Bone Geometry and Bone Quality in Distal Forearm Fracture," The Journal of Orthopedic Trauma, vol. 22, No. 8, Supplement, Philadelphia, Pennsylvania, Sep. 2008.
"Medtronic—Abdominal Stent Graft System, Instructions for Use," Medtronic, Inc., Minneapolis-Minnesota, 2008.
Jupiter, Jesse B., et al., "Operative Management of Distal Radial Fractures with 2.4-Millimeter Locking Plates. A Multicenter Prospective Case Series," The Journal of Bone and Joint Surgery, 91: 55-65, doi:10.2106-JBJS.G.01498, Needham, Massachusetts, Jan. 1, 2009.
App No. PCT/US2012/028145 International Search Report.
App No. PCT/US2012/028145 Written Opinion of the International Searching Authority.
Ilyas, Asif M., "Intramedullary Fixation of Distal Radius Fractures," Elsevier, Inc. on behalf of the American Society for Surgery of the Hand, New York, New York, Feb. 2009.
Figi, Markus, et al., "Volar Fixed-Angle Plate Osteosynthesis of Unstable Distal Radius Fractures: 12 Months Results," Springer, New York, New York, Feb. 19, 2009.
Photograph, OrthopaedicLIST, 2010, Wilmington, North Carolina.
Japanese Patent Office Action in Japanese App No. 2010-542429, Apr. 16, 2013.
United States Patent Office Action in U.S. Appl. No. 12/353,855, Jan. 31, 2012.
Barnes, C. Lowry, et al., "Advanced Core Decompression System," Wright, 2008, Arlington, Tennessee.
"OptiMesh 1500E—Percutaneous Interbody Fusion Surgical Technique," Spineology Inc., Feb. 2010, Saint Paul, Minnesota.
Corti, G., et al., "Acute Vertebral Body Compression Fracture treated with OptiMesh—Indications, Applications and First Clinical Results," Eurospine, 2005, Uster-Zürich Switzerland.
Advanced Core Decompression System—Surgical Technique, Wright, 2010, Arlington, Tennessee.
App No. PCT/US/2009/30971 International Search Report, Mar. 6, 2009.
App No. PCT/US/2009/30971 Written Opinion of the International Searching Authority, Mar. 6, 2009.
App No. PCT/US/2011/21074 International Search Report, May 23, 2011.
App No. PCT/US/2011/21074 Written Opinion of the International Searching Authority, May 23, 2011.
App No. PCT/US/2011/021735 International Search Report, May 25, 2011.
App No. PCT/US/2011/021735 Written Opinion of the International Searching Authority, May 25, 2011.
App No. PCT/US/2011/027597 International Search Report, Jul. 6, 2011.
App No. PCT/US/2011/027597 Written Opinion of the International Searching Authority, Jul. 6, 2011.
App No. PCT/US/2011/027602 International Search Report, Jul. 5, 2011.
App No. PCT/US/2011/027602 Written Opinion of the International Searching Authority, Jul. 5, 2011.
App No. PCT/US/2012/028145 International Search Report, Sep. 13, 2012.
App No. PCT/US/2012/028145 Written Opinion of the International Searching Authority, Sep. 13, 2012.
State Intellectual Property Office of the Peoples Republic of China, Chinese Patent Application No. 201180021809.7, First Office Action (Original), Aug. 1, 2014.
State Intellectual Property Office of the Peoples Republic of China, Chinese Patent Application No. 201180021809.7, First Search Report (Original), Jul. 22, 2014.
State Intellectual Property Office of the Peoples Republic of China, Chinese Patent Application No. 201180021809.7, First Office Action (English Translation, version 1), Aug. 1, 2014.
State Intellectual Property Office of the Peoples Republic of China, Chinese Patent Application No. 201180021809.7, First Office Action (English Translation, version 2), Aug. 1, 2014.
State Intellectual Property Office of the Peoples Republic of China, Chinese Patent Application No. 201180021809.7, First Search Report (English Translation), Jul. 22, 2014.

* cited by examiner

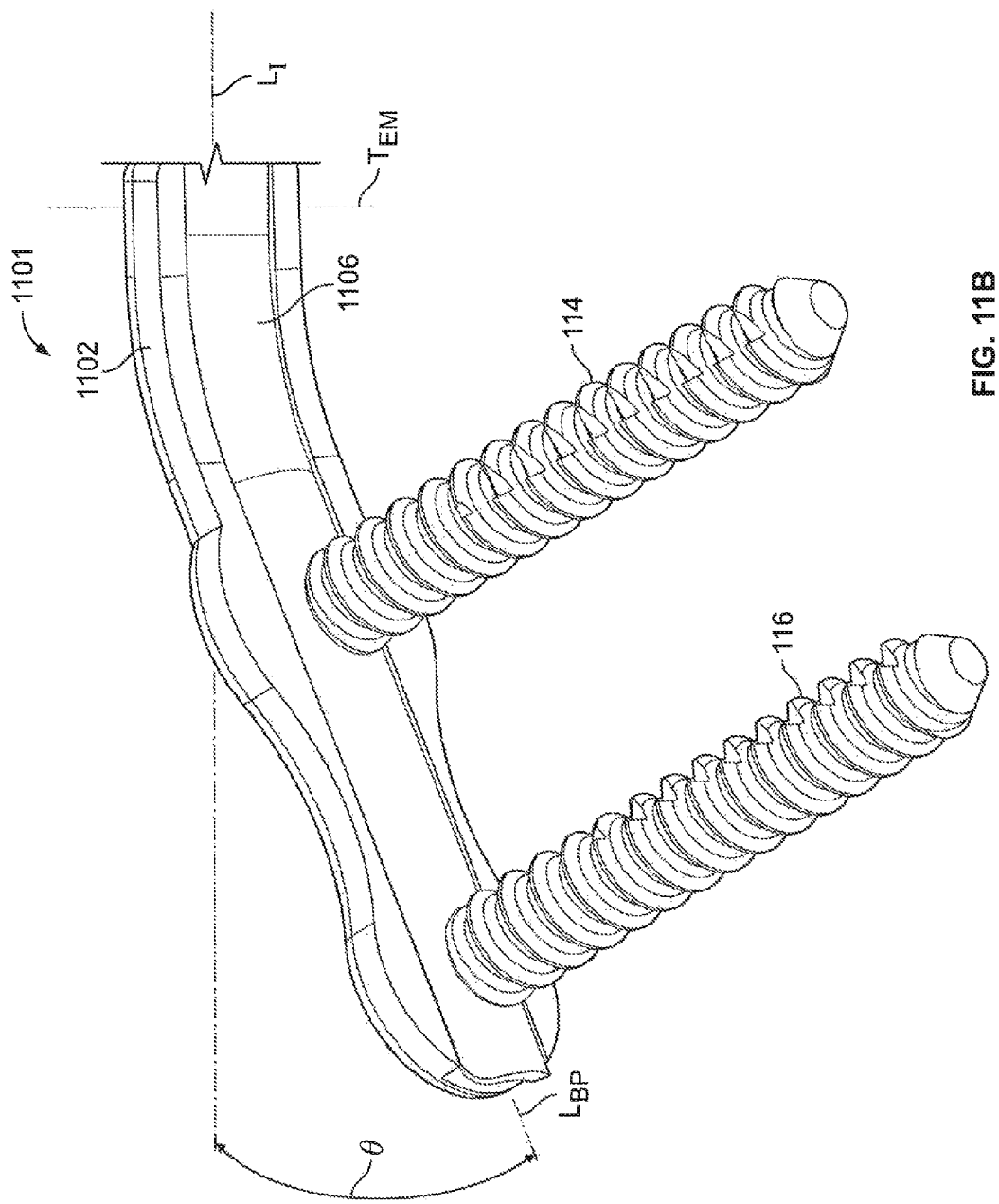

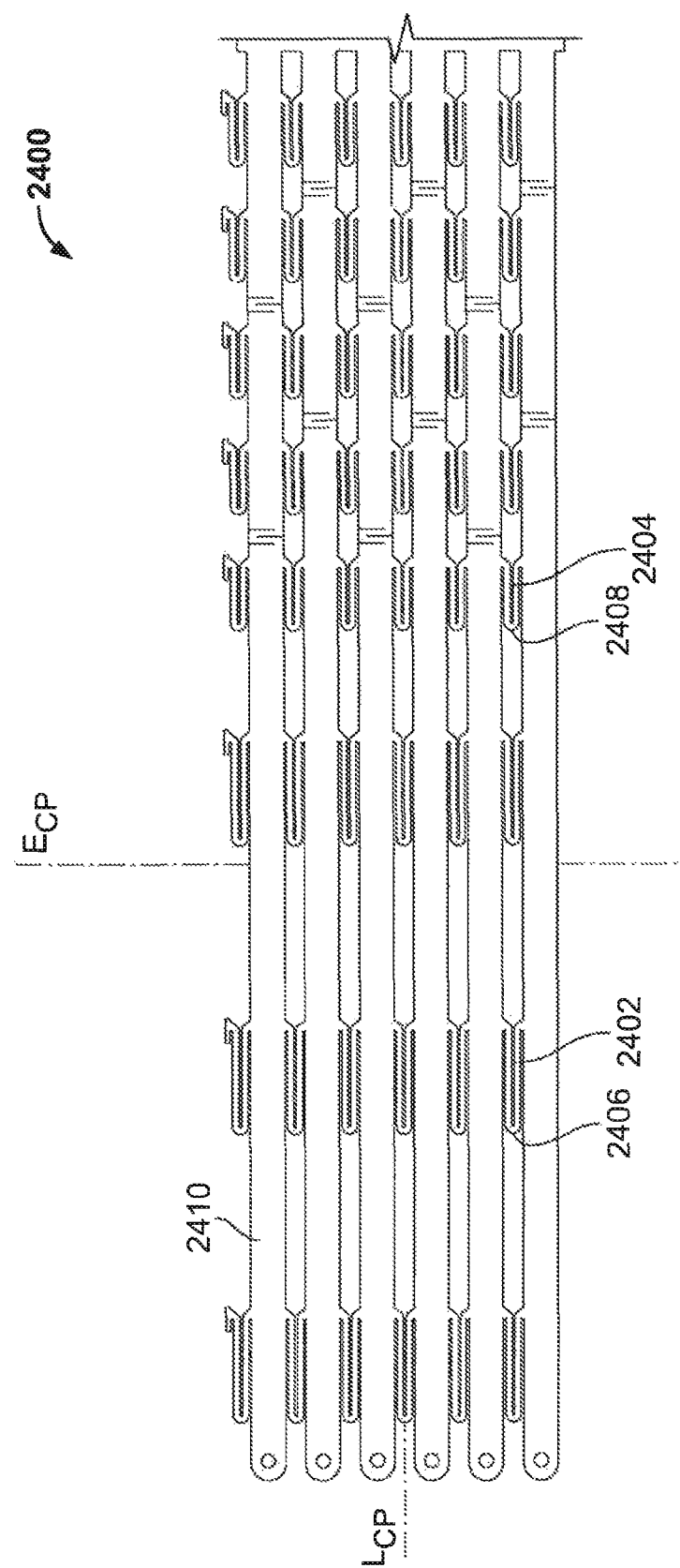

US 8,906,022 B2

APPARATUS AND METHODS FOR SECURING A BONE IMPLANT

CROSS-REFERENCE TO RELATED APPLICATIONS

This application is a nonprovisional of U.S. Provisional Applications Nos. 61/311,494, filed on Mar. 8, 2010 and 61/378,822 filed on Aug. 31, 2010, both of which are hereby incorporated by reference in their entireties.

FIELD OF TECHNOLOGY

Aspects of the disclosure relate to providing apparatus and methods for securing an implant deployed in a bone. In particular, the disclosure relates to apparatus and methods for repairing bone fractures utilizing a device that is inserted into a bone and secured to the bone.

BACKGROUND

The human body includes long, short, flat, irregular and sesamoid bone. A long bone is characterized by a midshaft. The midshaft of a long bone is typically classified as the diaphysis. The end of such a bone is typically classified as the epiphysis. Bone that is transitional between the midshaft and the end is typically classified as the metaphysis.

Multi-segment fractures, of either the midshaft or end-bone, require alignment and stability in a manner that generates adequate fixation in multiple directions.

However, midshaft fractures and end-bone fractures are fundamentally different. The loading conditions, fracture patterns, alignment needed, and compression force to promote healing are different. Midshaft fractures have ample bone material on either side of the fracture in which anchors may be driven. End-bone fractures, especially on the articular surface may have thin cortical bone, soft cancellous bone, and minimal anchoring locations.

Midshaft fractures tend to be loaded primarily in bending and torsion. End-bone fractures tend to be loaded in complex and multi-directional stress patterns. Midshaft repair approaches, therefore, may not be appropriate for repair of end-bone fractures.

There are two primary categories for surgical fixation of a long bone fracture: (1) a device that is within the skin (internal fixation); and (2) a device that extends out of the skin (external fixation). There are two common types of internal fixation approaches for long bone surgery (a) a plate that is screwed to the outside of the bone; or (b) a rod that goes down the center of the bone.

Intramedullary rods, nails or implants, are more effective than plates and screws at minimizing soft-tissue trauma and complications. Moreover, appropriate sizing of an implant helps realignment and healing of the fracture. Proper sizing of an implant may ensure proper matching of the implant device to a patient's anatomy.

An implant deployed in an intramedullary cavity of a bone may be expandable. An expandable implant may provide proper anatomic alignment and allow appropriate sizing of the implant. However, bone fractures require alignment and stability in a manner that generates adequate fixation in multiple directions.

It would be desirable, therefore, to provide apparatus and methods for securing an implant deployed inside a bone.

BRIEF DESCRIPTION OF THE DRAWINGS

FIG. 11B shows a sectional view of the apparatus shown in FIG. 11 in a view different than the view shown in FIG. 11;

FIG. 24A shows information that may be used to manufacture apparatus in accordance with principles of the invention;

DETAILED DESCRIPTION

Figure 1:
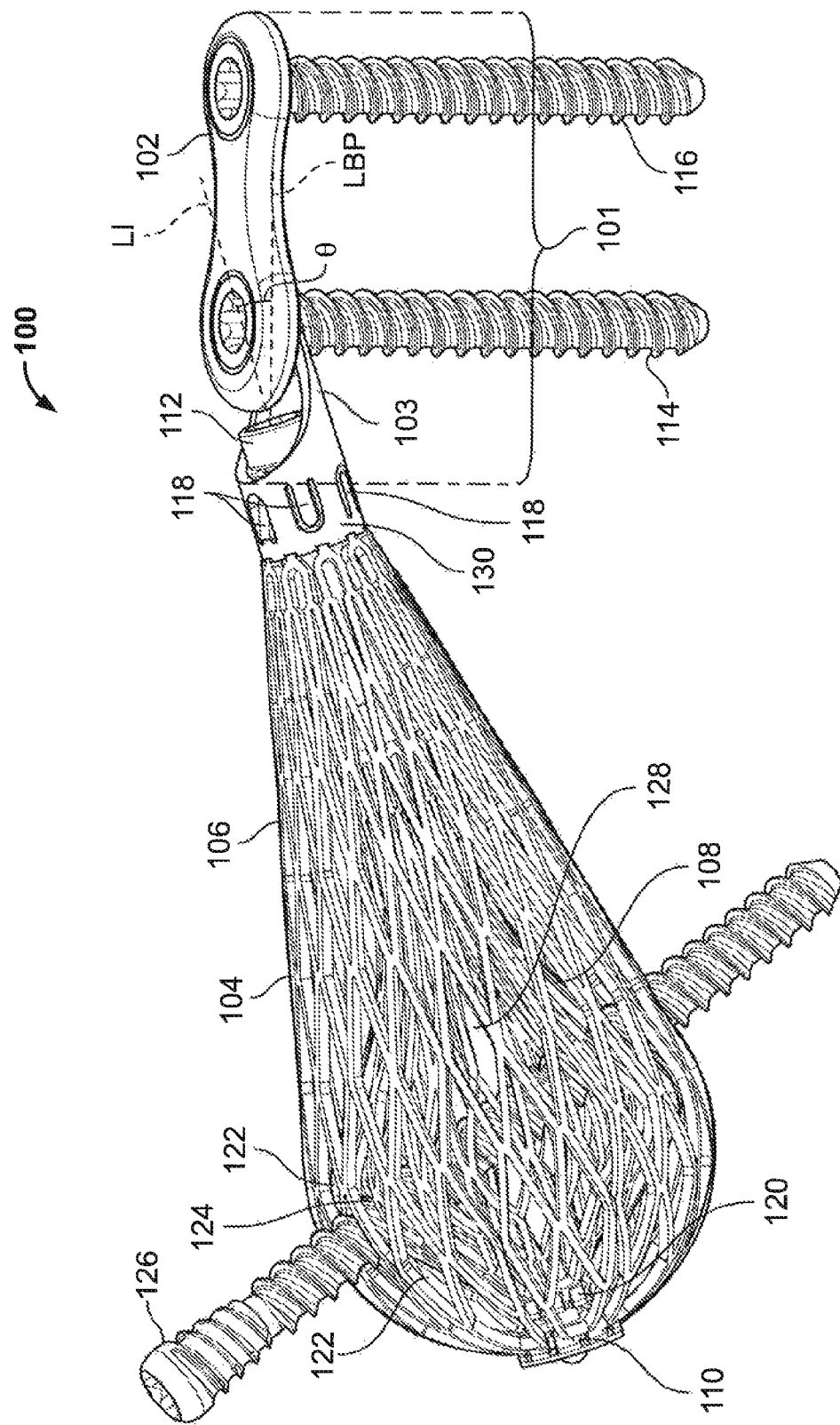
FIG. 1 shows perspective view of an illustrative apparatus in accordance with principles of the invention.

Apparatus and methods for securing an implant for a bone are provided. An implant may be secured to a bone to repair a fracture in the bone. The implant may be an expandable implant. The implant may be a non-expandable implant. The implant may be any suitable implant. For example, the implant may be an implant such as an implant that is shown and described in U.S. Patent Application Publication No. 2009/0182336 A1, which is hereby incorporated by reference in its entirety.

The bone may be accessed and prepared using any suitable technique such as that shown and described in U.S. patent application Ser. No. 13/009,657, which is hereby incorporated by reference in its entirety.

Copending U.S. patent application Ser. No. 13/043,330, entitled "APPARATUS AND METHODS FOR BONE REPAIR," filed on Mar. 8, 2011 is hereby incorporated by reference herein in its entirety. Copending U.S. Provisional Application No. 61/450,112 filed on Mar. 7, 2011, is hereby incorporated by reference herein in its entirety.

The apparatus and methods may involve fixing an expandable implant deployed inside a fractured bone. The apparatus and methods may involve the expansion of devices in the interior region of the bone. The expansion may involve any suitable expansion mechanism or technique, such as one or more of the mechanisms and techniques that are shown and described in U.S. Patent Application Publication No. 2009/0182336 A1.

The implant may have a first base and a second base. The implant may have a bone implant component that extends between the first base and the second base. The first base and the second base may define a longitudinal axis. The bone implant component may deflect relative to the longitudinal axis in correspondence with relative displacement of the first base and the second base along the axis.

The apparatus may include: a first body that is substantially coaxial with the axis and longitudinally fixed to the first base; a second body that is substantially coaxial with the axis and longitudinally fixed to the second base; and an elongated engaging member that is configured to longitudinally fix a distance between the first body and the second body.

The distance may have a maximum value that corresponds to a fully collapsed state of the implant. The distance may have a minimum value that corresponds to a fully expanded state of the implant. The elongated engaging member may be configured to longitudinally fix the distance at any value in the range from about the maximum value to about the minimum value.

The fully collapsed state may correspond to a state in which the implant is configured to pass through an access hole in the bone. The fully expanded state may correspond to a state in which the implant is expanded outside the bone at standard temperature and pressure. Standard temperature and pressure may be any standard temperature and any standard pressure, such as about 0 degrees Centigrade and about 1 atmosphere of pressure.

The distance may control the expansion of the implant by controlling the length of the implant. The distance may correspond to a therapeutic length of the bone implant. The distance may correspond to a therapeutic radius of the bone implant.

The elongated member may be of unified construction, and of all the structures that may be configured to operate in conjunction with the implant, the elongated engaging member alone may be configured to fix the distance.

The distance may correspond to an expansion state of the bone implant. In an expanded state, the implant may provide structural support for a bone. The implant may be locked in a state of expansion. The implant may be fixed in a state of expansion. The implant may be locked or fixed in a state of expansion such that residual outward radial pressure on an inside wall of the bone may be substantially reduced or eliminated.

In a contracted state, the implant may provide structural support for the bone. The implant may be locked in a state of contraction. The implant may be fixed in a state of contraction. The implant may be locked or fixed in a state of contraction such that residual outward radial pressure on an inside wall of the bone may be substantially reduced or eliminated.

The elongated engaging member may be configured to apply tension between the first body and the second body. The elongated member may be of unified construction and of all the structures that are configured to operate in conjunction with the implant, the elongated engaging member alone may be configured to apply the tension.

In some embodiments, when the elongated member fixes the distance, the elongated member may engage the first body internal to the first body and the second body internal to the second body.

The first body may include a first tapped cannula. The second body may include a second tapped cannula. The elongated member may include a thread that is configured to engage the first tapped cannula and the second tapped cannula.

The thread may be sufficiently fine to avoid substantially changing the distance when the thread, after engaging the first tapped cannula, engages the second tapped cannula.

The second body may have an outer diameter. The first body may include a cylindrical portion that has an inner diameter that is greater than the outer diameter of the second body. The cylindrical portion may be configured to receive a portion of the second body.

The apparatus may include a scaffolding extends between the first base and the second base. The scaffolding may include the bone implant component. The scaffolding may be configured to support a bone.

In some embodiments, when the first base moves toward the second base, the scaffolding may expand away from the longitudinal axis.

The implant may include an anchoring substrate. The anchoring substrate may be disposed between the longitudinal axis and the scaffolding.

In some embodiments, an anchoring substrate may extend between the first and second bases. The anchoring substrate may include the bone implant component and may be configured to support a bone.

In some embodiments, when the first base moves toward the second base, the anchoring substrate may expand away from the longitudinal axis.

The implant may include a scaffolding that is, relative to the longitudinal axis, at a greater radial distance than is the anchor substrate.

A tab may extend from one or both of the first base and the scaffolding. A pocket may be present in one or both of the first base and the scaffolding. The tab may be biased such that it engages the pocket. The scaffolding may be substantially longitudinally and rotationally fixed to the first base by the engagement of the tab and the pocket.

In some embodiments, when the distance is fixed, the anchor substrate may be slidable along the longitudinal axis and angularly displaceable about the longitudinal axis.

The methods may include a method for controlling the expanded diameter of a bone implant inside a bone. The method may include controlling the length of the implant by fixing a distance between a first base and a second base using an elongated member that extends between the first base and the second base. The first and second bases may be substantially collinear. The method may include closing the elongated member inside the bone by closing an access hole through which the implant was delivered into the bone.

In some embodiments, the implant may have a fully collapsed state and a fully expanded state. The fully collapsed state may correspond to a state in which the implant is configured to pass through an access hole in the bone. The fully expanded state corresponding to a state in which the implant is expanded outside the bone at standard temperature and pressure. The method may include, when the implant has a fully collapsed state and a fully expanded state, fixing the distance at a value that is: not greater than a maximum value that corresponds to the fully collapsed state of the implant; and not less than a minimum value that corresponds to fully expanded state of the implant.

A method for treating a bone fracture is provided. The method may include positioning a first bone fragment at a reduced displacement relative to a second bone fragment such that the fracture is provisionally reduced. The method may include deploying an implant in an interior region of the bone, the implant having an expanded dimension that is greater than a corresponding dimension of the interior region. The method may include inserting into the implant a tension-storing element that prevents the implant from urging the first bone fragment away from the reduced displacement.

The positioning of a first bone fragment at a reduced displacement relative to a second bone fragment such that the fracture is provisionally reduced may include inserting a K-wire through the first bone fragment and the second bone fragment.

Inserting into the implant a tension-storing element that prevents the implant from urging the first bone fragment away from the reduced displacement may include fixing an axial distance between a first hub and a second hub. The first hub and the second hub may be configured to expand the implant when drawn together and collapse the implant when moved apart.

The method may include, after the deploying and before the inserting, adjusting the axial distance. Fixing the axial distance between a first hub and a second hub may include advancing the tension-storing element along the axial distance to engage a first body that is fixed to the first hub and a second body that is fixed to the second hub. The advancing the tension-storing element may include rotating the tension-storing element.

Apparatus for an expandable a bone implant is provided. The expandable implant may include a hub, a central axis member and a support member. The support member may include a first end and a second end. The first end and the second end may be spaced apart from each other along the central axis member. The support member may have a mid-section that is configured to deflect radially away from the central axis member when the implant expands.

The hub may include a support member terminal. The support member terminal may be configured to: fix the second end longitudinally relative to the central axis member during expansion of the implant; and fix the second end radially relative to the central axis member during the expansion.

In some embodiments, the support member terminal may include a clearance notch for the support member so that the second end may have an angular range of motion during the expansion.

The second end may include a tab. The support member terminal may include an enclosure. The enclosure may be configured to enclose the tab. The notch may be configured to traverse the enclosure.

The enclosure may include a first enclosure member. The enclosure may include a second enclosure member. The second enclosure member may be configured to be separated from the first enclosure member and admit the tab into the enclosure.

The first enclosure member may include a detent surface that limits the angular range of motion. The detent surface may include an end of the notch.

The second enclosure member may include a detent surface that limits the angular range of motion.

The support member terminal may be configured to rotate about the central axis member.

The support member terminal may be rotationally fixed relative to the central axis member.

Apparatus and methods for stabilizing a bone implant are provided. The bone may have an access hole for delivery of the implant. The access hole may have a hole wall.

The implant may include a stabilizer. The stabilizer may include an elongated member. The elongated member may be configured to extend along the hole, and between the implant, when the implant is deployed in the bone, and an anchor receiving feature. The anchor receiving feature may be configured to receive an anchor driven into the hole wall. The stabilizer may include one or more anchor receiving features.

The elongated member may include an extension that extends beyond the anchor receiving feature and is configured to articulate with a buttress plate.

The extension may include a first surface that is circumferential about the anchor receiving member. The buttress plate may include a second surface that is complementary to the first surface. Traction from an anchor received by the anchor receiving feature may be configured to brace the second surface against the first surface.

The elongated member may be configured to resist rotation of the implant in the hole. The elongated member may be configured to resist axial movement of the implant along the hole. The elongated member may be configured to resist rotation of the implant in the hole and axial movement of the implant along the hole.

The implant may include a locking mechanism for maintaining a shape of the implant. The locking mechanism may be configured to be locked by a screw inserted into the access hole. The screw may be adjustable after the anchor receiving feature has received the anchor.

The stabilizer may include a buttress plate anchored to the bone. The buttress plate may be positioned substantially parallel to a longitudinal axis of the bone. The buttress plate may be configured to resist rotational movement of the elongated member about a central axis of the hole.

The buttress plate may include a second anchor receiving feature configured to receive the anchor.

The buttress plate may be configured to resist axial movement of the elongated member along the hole.

The buttress plate may be configured to resist rotation of the elongated member in the hole and axial movement of the elongated member along the hole.

The buttress plate may include a second anchor receiving feature configured to receive the anchor.

The buttress plate may include a third anchor receiving feature configured to receive an anchor driven into an outer surface of a cortical wall of the bone.

The stabilizer may include a first edge adjacent to the first anchor receiving feature and a second edge adjacent to the first anchor receiving feature. The buttress plate may include a second anchor receiving feature that is configured to receive the anchor. The first edge and the second edge may define a pivot axis. The anchor may be configured to secure the buttress plate in contact with the bone and in a position substantially parallel to an outer surface of the bone.

In embodiments of the stabilizer that include a pivot axis, the buttress plate may be configured to resist rotation of the elongated member in the hole, axial movement of the elongated member along the hole and/or rotation and axial movement of the elongated member in the hole.

In embodiments of the stabilizer that include a pivot axis, the buttress plate may transmit no substantial bending moment about the pivot axis to the elongated member.

In embodiments of the stabilizer that include a pivot axis, the buttress plate may include a third anchor receiving feature configured to receive an anchor driven into an outer surface of a cortical wall of the bone.

The stabilizer may include a buttress plate anchored to the bone and positioned substantially parallel to a longitudinal axis of the bone. The buttress plate may include a first indent and a second indent. The elongated member may include a ridge.

The first indent and the second indent may be configured to engage the ridge and resist rotation of the elongated member in the hole. The first indent and the second indent may be configured to engage the ridge and resist axial movement of the elongated member along the hole. The first indent and the second indent may be configured to engage the ridge and resist rotation of elongated member about an axis perpendicular to a longitudinal axis of the implant.

In some embodiments, the elongated member may be configured to be positioned within the access hole after the implant has been deployed inside the bone.

The implant may be configured to be deployed through an access hole in a cortical wall of the bone. In some embodiments, the stabilizer may include an elongated member that is configured to extend between the implant, when the implant is deployed in the bone, and an anchor receiving feature that is configured to receive an anchor that is driven into an outer surface of the cortical wall. The elongated member may be configured to be deformed to position the anchor receiving feature along the outer surface of the cortical wall.

The stabilizer may include a buttress plate configured to be positioned over the elongated member. The buttress plate positioned over the elongated member may resist rotation of the elongated member about a central axis of the hole. The buttress plate positioned over the elongated member may resist rotation of the elongated member about an axis transverse to the elongated member.

In some embodiments that include an elongated member configured to be deformed, the elongated member may be configured to be attached to the implant after the implant is deployed in the bone.

In some embodiments, the stabilizer may include a site for an anchor receiving feature that is configured to receive an anchor driven into an outer surface of the cortical wall. An elongated member may be configured to extend between the implant, when the implant is deployed in the bone, and the site. A buttress plate may be positioned over the elongated member and configured to resist rotation of the elongated member about a central axis of the access hole, and axial movement of the elongated member transverse to the elongated member.

In some embodiments of a stabilizer including a site for an anchor receiving feature, the stabilizer may be attached to the implant after the implant is deployed in the bone.

The stabilizer may include an elongated member that is configured to extend along the hole and between the implant, when the implant is deployed in the bone, and a buttress collar. The buttress collar may be supported at an opening of the access hole. The elongated member may terminate at the buttress collar. The buttress collar may be substantially parallel to an outside surface of the cortical wall.

Some embodiments of the stabilizer having a buttress collar may include an anchor receiving feature configured to receive an anchor driven into the outside surface of the cortical wall.

In some embodiments of the stabilizer, an angle between a central axis of the access hole and a central axis of the implant may be adjustable. The stabilizer may include a locking mechanism configured to lock the adjustable angle. The elongated member may include an articulating surface. The adjustable angle may be between 0 degrees and 5 degrees, between degrees and 10 degrees, between 0 degrees and 15 degrees, between 0 degrees and 20 degrees, between 0 degrees and 25 degrees, between 0 degrees and 30 degrees, between 0 degrees and 35 degrees, between 0 degrees and 45 degrees, between 0 degrees and 90 degrees, or within any other suitable angular range.

System and methods for securing a bone implant in a bone, are provided. The system may include an expandable web having a front and a back. The web may be configured to be inserted in an interior of the bone. The web may include an expandable cell having an expanded diameter.

The system may include an anchor that may be configured to secure a fragment of the bone to the expandable web when the expandable web is inside the bone. The anchor may have an elongated shaft for penetrating the cell from the front and an engagement feature that extends transversely away from the shaft and may be configured to engage the back of the cell to apply tension between the cell and the bone fragment. The shaft may have a shaft diameter that is sufficiently great, relative to the expanded diameter, to prevent disengagement of the engagement feature from the back of the cell when the tension is applied.

The expanded diameter may be a diameter of the cell when the expandable web is in an expanded state before the engagement feature engages the back of the cell.

The expanded diameter may be a diameter of the cell when the expandable web is in an expanded state, the engagement feature is engaging the back of the cell, and the cell is elastically deformed by the tension.

The expanded diameter may be a diameter of the cell when the expandable web is in an expanded state, the engagement feature is engaging the back of the cell, and the cell is plastically deformed by the tension.

The anchor may be a screw. The engagement feature may be a spiral thread. When the anchor is a screw and the engagement feature a spiral thread, one or more of the screw root diameter, the screw thread diameter and the thread pitch is selected based on a failure strain of the cell.

When the anchor is a screw and the engagement feature is a spiral thread, one or more of the screw root diameter, the screw thread diameter and the thread pitch may be selected based on an elastic deformation limit of the cell.

When the anchor is a screw and the engagement feature is a spiral thread, a screw metric may be selected based on a failure strength of the cell.

The screw metric may be a screw major diameter. The screw metric may be a screw mean diameter. The screw metric may be a screw minor diameter. The screw metric may be a thread pitch. The screw metric may be a screw thread angle.

Apparatus and methods for securing components of a bone implant are provided. The apparatus may include a bracket that may be configured to receive a bone anchor. The apparatus may include an extension member that may be configured to support the bracket relative to a bone implant that is deployed inside the bone. The apparatus may include a fastening assembly that is configured to fasten: the bracket to the extension; and the extension to the implant.

The fastening assembly may include a first state in which the bracket is movable relative to the implant, and a second state in which the bracket is locked relative to the implant.

In the first state, the bracket may be movable from a first distance from the implant to a second distance from the implant.

In the first state, the bracket may be movable from a first angle relative to the implant to a second angle relative to the implant.

In the first state, the bracket may be movable from: a first distance from the implant to a second distance from the implant; and a first angle relative to the implant to a second angle relative to the implant.

The fastening assembly may include a fastener. The fastener may be configured to press the extension toward the implant and induce friction between the extension and the bracket.

The apparatus may include an expansion bushing. The fastener may be configured to drive the expansion bushing toward the implant to press the extension toward the implant and expand the extension to interfere with movement of the bracket.

The bracket may have a tubular section. The extension may have a tubular section that is within the bracket tubular section. The expansion bushing may include a portion that is within the extension tubular section. The fastener may include a screw. The screw may have a portion that is within the expansion bushing.

Apparatus and methods for a bone implant are provided. The bone implant may include a central axis member. The bone implant may include a first expandable web that may be supported coaxially about the central axis member. The bone implant may include a second expandable web that may be supported coaxially about the central axis member and within the first expandable web.

The central axis member may define a longitudinal axis. The first expandable web may have a first mesh cell density. The first mesh cell density may vary along the axis, so that the first expandable web, when expanded, has a first radius that is based on the first mesh cell density; and the second expandable web has a second mesh cell density. The second mesh cell density may vary along the axis, so that the second expandable web, when expanded, has a second radius that is based on the second mesh cell density.

In some embodiments, along substantially the entire length of the second web, a ratio of the first radius to the second radius may be substantially constant.

In some embodiments, along a length of the second web, a ratio of the first radius to the second radius may be substantially constant.

The second radius may have a second radius maximum between a distal end of the second web and a proximal end of the second web. The second radius may decrease substantially linearly from the maximum toward the distal end. The second radius may decrease substantially linearly from the maximum toward the proximal end.

In some embodiments, between the distal end of the second web and the proximal end of the second web a difference between the second radius and the first radius may define a radial offset. The radial offset may have an offset minimum that corresponds to the second radius maximum.

The offset minimum may be sufficiently small that, when the first expandable web bears a radial load, the first expandable web deforms to transmit the load to the second expandable web at the second radius maximum.

The first expandable web may include a first plurality of open cells. The second expandable web may include a second plurality of open cells. The first and second pluralities may be configured to engage an anchor and deliver tension to the anchor to retain a bone fragment that is engaged with the anchor.

The second expandable web may be rotatably supported about the longitudinal axis such that the second expandable web can rotate in response to interference from the anchor during engagement of the second expandable web by the anchor.

Apparatus and methods for a bone implant having different zones of flexibility are provided. The implant may include a structural component. The structural component may have an expanded state, a collapsed state, a longitudinal axis and a transverse axis to the longitudinal axis. The transverse axis may be perpendicular to the longitudinal axis. The structural component may include, along the longitudinal axis: a first zone; a second zone; and a third zone.

The first zone may have a first resistance to bending about the transverse axis. The second zone and the third zone may have a second resistance to bending about the transverse axis. In the collapsed state, the first resistance to bending may be greater than the second resistance to bending.

The second resistance to bending in the expanded state may be greater than the second resistance to bending in the collapsed state.

The first zone may include a first cell and the third zone may include a second cell. The first cell may be circumferentially spaced, about the longitudinal axis, a first distance, from the second cell and longitudinally spaced, along the longitudinal axis, a second distance from the second cell. The second zone may include a link from the first cell to the second cell.

An increase in the first distance may correspond to an increase in flexibility of the second zone about the transverse axis. An increase in the second distance corresponds to an increase in flexibility of the second zone about the transverse axis.

The first zone may include a third cell. The third cell may be circumferentially spaced, about the longitudinal axis, a third distance, from the second cell and longitudinally spaced, along the longitudinal axis, a fourth distance from the second cell.

The third zone may include a fourth cell. The fourth cell may be circumferentially spaced, about the longitudinal axis, the first distance from the third cell and longitudinally spaced, along the longitudinal axis the second distance from the third cell.

The second zone may include, when the link is a first link, a second link from the third cell to the fourth cell. In the expanded state, the first link may stack upon the second link. The link may tortuously link the first cell and the second cell.

The first zone may include a first cell and the third zone may include a second cell. The first cell may be circumferentially aligned, about the longitudinal axis, with the second cell and longitudinally spaced, along the longitudinal axis, a distance from the second cell. The second zone may include a link from the first cell to the second cell. The link may tortuously links the first cell to the second cell.

The link may include a "V" shaped link, the link may have an apex, a first leg and a second leg. Under compression along the longitudinal axis, the first leg and the second leg may collapse about the apex.

The implant may include a structural component. The implant may have an expanded state, a collapsed state and a longitudinal axis. The structural component may include a first structural member extending along the longitudinal axis. The structural component may include a second structural member extending along the longitudinal axis and spaced circumferentially about the longitudinal axis from the first member.

The structural component may include a cross support that spans from the first member to the second member. The cross support may include a member having a joint. The member may be configured to be folded about the joint in the collapsed state and unfolded about the joint in the expanded state.

In some embodiments, when the cross support is folded, an angle of the member may be substantially 0 degrees and when the cross support is unfolded, the angle of the member may be substantially 180 degrees.

The unfolded cross support may limit an expansion of the implant from the longitudinal axis.

The support component may define a plane. The implant may have a longitudinal axis that lies in the plane, a first transverse axis that lies in the plane and is perpendicular to the longitudinal axis and a second transverse axis that is perpendicular to the longitudinal axis and perpendicular to the plane.

The support component may have a first resistance to bending about the longitudinal axis or about the first transverse axis. The support component may have a second resistance to bending about the second transverse axis. The first bending resistance may be greater than the second bending resistance.

The support component may include a first member and a second member. The first member may have a third resistance to bending about the longitudinal axis or about the first transverse axis and a fourth resistance to bending about the second transverse axis. The second member may have a fifth resistance to bending about the longitudinal axis or about the first transverse axis and a sixth resistance to bending about the second transverse axis.

The support component may include a first anchor receiving feature and a second anchor receiving feature. The first anchor receiving feature and the second anchor receiving feature may be configured to receive an anchor that lies in the plane.

Apparatus and methods for a multi-fold single layer implant for a bone are provided.

The implant may include a central axis member that defines a longitudinal axis. The implant may include an expandable web that may be supported coaxially about the central axis member.

The expandable web may include a first mesh cell density that may vary longitudinally along a first segment of the expandable web. The expandable web may include a second mesh cell density that may vary longitudinally along a second segment of the expandable web. The expandable web may include a third mesh cell density that varies longitudinally along a third segment of the expandable web. The expandable web may include a fourth mesh cell density that varies longitudinally along a fourth segment of the expandable web. The expandable web may include a fifth mesh cell density that varies longitudinally along a fifth segment of the expandable web.

When the expandable web is in an expanded state, the first segment may have a first profile, the second segment may have a second profile, the third segment may have a third profile, the fourth segment may have a fourth profile, and the fifth segment may have a fifth profile.

In an unexpanded state, the first, second, third, fourth and fifth segments may be consecutively longitudinally ordered. In the expanded state, the first and fifth segments may be concave facing each other. The second and fourth segments may bridge, respectfully, from the first segment to the third segment and from the third segment to the fifth segment.

In the expanded state, the third segment may be substantially cylindrical.

In the expanded state, the third segment may be ellipsoidal. For example, when viewed transversely relative to the central axis, the third segment may have an outline that is ellipsoidal.

In the expanded state, the first segment may have a first segment maximum radius, the third segment may have a third segment maximum radius, the fifth segment may have a fifth segment maximum radius, and both the first segment maximum radius and the fifth segment maximum radius may be greater than the third segment maximum radius.

A ratio of one of the first segment maximum radius and the fifth segment maximum radius to the third segment maximum radius may be at least 1.1.

Apparatus and methods for a hat shaped multi-fold single layer implant for a bone are provided.

The implant may include a central axis member that defines a longitudinal axis. The implant may include an expandable web that may be supported coaxially about the central axis member.

The expandable web may include a first mesh cell density that varies longitudinally along a first segment of the expandable web. The expandable web may include a second mesh cell density that varies longitudinally along a second segment of the expandable web. The expandable web may include a third mesh cell density that varies longitudinally along a third segment of the expandable web.

When the expandable web is in an expanded state, the first segment may have a first profile, the second segment may have a second profile and the third segment may have a third profile.

In an unexpanded state, the second segment may be longitudinally between the first segment and the third segment. In the expanded state, the first segment may be ellipsoidal, the third segment may be concave facing the first segment and the second segment may bridge from an outer radius of the third segment to an adjacent tip of the first segment.

In the expanded state, the second segment may have a portion that is concave facing the first segment.

In the expanded state, the second segment may have a portion that is convex facing the first segment.

In the expanded state, the second segment may have a portion that is convex facing the first segment.

In the expanded state the first segment may have a first segment maximum radius, the third segment may have a second segment maximum radius and the third segment maximum radius may be greater than the first segment maximum radius.

A ratio of the third segment maximum radius to the first segment maximum radius may be at least 1.1.

In the expanded state the first segment may have a first longitudinal diameter. In the expanded state, the second and third segments together may define a second longitudinal diameter. In the expanded state, the first longitudinal diameter may be greater than the second longitudinal diameter.

A ratio of the first longitudinal diameter to the second longitudinal diameter may be at least 2.5.

In the expanded state, the first segment may have a first segment maximum radius. In the expanded state, the third segment may have a second segment maximum radius. In the expanded state, the first segment maximum radius may be greater than the third segment maximum radius. A ratio of the first segment maximum radius to the third segment maximum radius may be at least 1.1.

In the expanded state the first segment may have a first longitudinal diameter. In the expanded state, the second and third segments together may define a second longitudinal diameter. The second longitudinal diameter may be greater than the first longitudinal diameter. A ratio of the second longitudinal diameter to the first longitudinal diameter may be at least 2.5.

Apparatus and methods for a non-round implant for a bone are provided.

The implant may include a central axis member that may define a longitudinal axis. The implant may include an expandable web that may be supported coaxially about the central axis member.

The expandable web may include a first mesh cell density that may vary longitudinally along a first segment of the expandable web. The expandable web may include a second mesh cell density that may vary longitudinally along a second segment of the expandable web. The expandable web may include a third mesh cell density may vary longitudinally along a third segment of the expandable web.

When the expandable web is in an expanded state, the first segment may have a first profile, the second segment may have a second profile and the third segment may have a third profile.

In an unexpanded state, the second segment may be longitudinally between the first segment and the third segment. In the expanded state, the first profile may be a substantially conical shape that opens toward the second segment. In the expanded state, the third segment may be substantially planar and substantially normal to the central axis member. In the expanded state, the second segment may bridge from an outer radius of the first segment to an outer radius of the third segment.

In the expanded state, the second profile may be substantially conical and may have a first radius at a joint with the first profile and may have a second radius at a joint with the third profile. The second radius may be greater than the first radius. A ratio of the second radius to the first radius may be at least 1.1.

Apparatus and methods for a bone engaging member for a an implant for a bone are provided.

The implant, when deployed inside the bone, may define, at a distal end of the implant, an enclosed region. The bone engaging member may be configured to extend out of the region and into the bone.

The implant may include a support structure that converges toward a distal end of the implant. The bone engaging member may be configured to diverge from the support structure and extend into the bone.

The bone engaging member may not be fixed directly to the support structure. The bone engaging member may be fixed directly to the support structure.

The bone engaging member may be configured to extend for a first length of the bone engaging member alongside a supporting member of the implant along and for a second length of the bone engaging member into the bone.

The first length may extend substantially perpendicular to a surface of the support structure.

The bone engaging member may be configured to extend substantially perpendicular to the surface of the support structure after an expansion of the implant.

The bone engaging member may be configured to extend into a cancellous portion of the bone.

The bone engaging member may be configured to resist translational motion of the implant relative to the bone.

The bone engaging member may be configured to resist rotational motion of the implant relative to the bone.

The bone engaging member may be one of several bone engaging members that diverge from the support structure and extend into the bone.

The bone engaging member may include a distal tip. The distal tip may be configured to coordinate with an internal geometry of the bone.

The bone engaging member may be configured to be fixed to the implant at a proximal end of the implant.

The bone engaging member may be configured, when the implant is deployed through an access hole in the bone, to be inserted into the access hole after the implant is deployed in the bone.

The bone engaging member may be configured, when the implant is deployed through an access hole in the bone, to be inserted into the access hole after the implant.

One or more surfaces of the apparatus may be coated with agents that promote bone ingrowth. The agents may include calcium phosphate, heat treated hydroxylapatite, Basic fibroblast growth factor (bFGF)-coated hydroxyapatite, hydroxyapatite/tricalcium phosphate (HA/TCP), and other suitable agents, including one or more of those listed in Table 1.

One or more surfaces of the apparatus may be coated with agents that inhibit or prohibit bone ingrowth. Such surfaces may include impermeable and other materials such as one or more of those listed in Table 1.

One or more surfaces of the apparatus may be coated with agents that may elute therapeutic substances such as drugs.

The apparatus and portions thereof may include any suitable materials. Table 1 lists illustrative materials that may be included in the apparatus and portions thereof.

TABLE 1

| Materials | | |
|---|---|---|
| Category | Type | Material |
| Metals | Nickel titanium alloys | Nitinol |
| | Stainless steel alloys | 304 |
| | | 316L |
| | | BioDur ® 108 Alloy |
| | | Pyromet Alloy ® CTX-909 |
| | | Pyromet ® Alloy CTX-3 |
| | | Pyromet ® Alloy 31 |
| | | Pyromet ® Alloy CTX-1 |
| | | 21Cr—6Ni—9Mn Stainless |
| | | 21Cr—6Ni—9Mn Stainless |
| | | Pyromet Alloy 350 |
| | | 18Cr—2Ni—12Mn Stainless |
| | | Custom 630 (17Cr—4Ni) Stainless |
| | | Custom 465 ® Stainless |
| | | Custom 455 ® Stainless Custom 450 ® Stainless |
| | | Carpenter 13-8 Stainless |
| | | Type 440 C Stainless |
| | Cobalt chromium alloys | MP35N |
| | | Elgiloy |
| | | L605 |
| | | Biodur ® Carpenter CCM alloy |
| | Titanium and titanium alloys | Ti—6Al—4V/ELI |
| | | Ti—6Al—7Nb |
| | | Ti—15Mo |
| | Tantalum | |
| | Tungsten and tungsten alloys | |
| | Pure Platinum | |
| | Platinum-Iridium alloys | |
| | Platinum-Nickel alloys | |
| | Niobium | |
| | Iridium | |
| | Conichrome | |
| | Gold and Gold alloys | |
| Absorbable metals | | Pure Iron |
| | | magnesium alloys |
| Polymers | | Polyetheretherketone (PEEK) |
| | | polycarbonate |
| | | polyolefin's |
| | | polyethylene's |
| | | polyether block amides (PEBAX) |
| | | nylon 6 |
| | | 6-6 |
| | | 12 |
| | | Polypropylene |
| | | polyesters |
| | | polyurethanes |
| | | polytetrafluoroethylene (PTFE) |
| | | Poly(phenylene sulfide) (PPS) |
| | | poly(butylene terephthalate) PBT |
| | | polysulfone |
| | | polyamide |
| | | polyimide |
| | | poly(p-phenylene oxide) PPO |
| | | acrylonitrile butadiene styrene (ABS) |
| | | Polystyrene |
| | | Poly(methyl methacrylate) (PMMA) |
| | | Polyoxymethylene (POM) |
| | | Ethylene vinyl acetate |
| | | Styrene acrylonitrile resin |
| | | Polybutylene |

TABLE 1-continued

| Materials | | |
|---|---|---|
| Category | Type | Material |
| Membrane materials | | Silicone |
| | | Polyether block amides (PEBAX) |
| | | Polyurethanes |
| | | Silicone polyurethane copolymers |
| | | Nylon |
| | | Polyethylene terephthalate (PET) |
| | | Goretex ePTFE |
| | | Kevlar |
| | | Spectra |
| | | Dyneena |
| | | Polyvinyl chrloride (PVC) |
| Absorbable polymers | | Poly(glycolic acid) (PGA) |
| | | Polylactide (PLA), |
| | | Poly(ε-caprolactone), |
| | | Poly(dioxanone) |
| | | Poly(lactide-co-glycolide) |
| Radiopaque materials | | Barium sulfate |
| | | Bismuth subcarbonate |
| Biomaterials | Collagen | Bovine, porcine, ovine, amnion membrane |
| Bone growth factors | | Demineralized bone matrix |
| | | Bone morphogenic proteins (BMP) |
| | | Calcium phosphate |
| | | Heat-treated hydroxylapapatite |
| | | Basic fibroblast growth factor (bFGF)-coated hydroxyapaptite |
| | | Hydroxyapaptite/tricalcium phosphate (HA/TCP |
| Antimicrobial Coatings | | |

The apparatus may be provided as a kit that may include one or more of a structural support, an anchoring substrate, a central axis member, an anchor, a delivery instrument and associated items.

Apparatus and methods in accordance with the invention will now be described in connection with the FIGS. The FIGS. show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments may omit steps shown and described in connection with the illustrative methods. Some embodiments may include steps that are not shown and described in connection with the illustrative methods.

Illustrative embodiments will now be described with reference to the accompanying drawings, which form a part hereof.

The apparatus and methods of the invention will be described in connection with embodiments and features of an illustrative bone implants and associated hardware and instrumentation. The implants and associated hardware and instruments will be described now with reference to the FIGS. It is to be understood that other embodiments may be utilized and structural, functional and procedural modifications may be made without departing from the scope and spirit of the present invention.

FIG. 1 shows illustrative implant 100. Implant 100 may be implanted in a bone (not shown). Implant 100 is elongated along its longitudinal axis LI (in which I indicates implant). Implant 100 may include an outer expandable web 106. Implant 100 may include an inner expandable web 108. Expandable web 106 may be expanded to a radial distance from LI. Expandable web 108 may be expanded to a radial distance from LI.

Implant 100 may include stabilizer 101. Stabilizer 101 may include buttress plate 102. Buttress plate 102 may be elongated along a longitudinal axis LBP (in which BP indicates buttress plate). Longitudinal axis LBP may form angle θ with longitudinal axis LI. In some embodiments, angle θ may be adjustable.

Stabilizer 101 may be secured to a bone with anchor 114. Anchor 114 may secure buttress plate 102 to the bone. Buttress plate 102 may be secured to the bone with anchor 116.

Implant 100 may include an expansion locking screw 112 for locking expandable web 106 and/or expandable web 108 at a distance from LI. Stabilizer 101 may be secured to implant 100 using any suitable approach, such as with tabs 118.

Expandable web 106 may extend from proximal base 130 to distal hub 110. ("Distal," relative to "proximal," generally means the leading end of an apparatus that is inserted, or is to be inserted, in the body.) Expandable web 108 may extend from a proximal base (not shown) to distal hub 120.

Expandable web 106 may include an arrangement of cells 122. Expandable web 108 may include an arrangement of cells 124. An arrangement of cells 122 and/or cells 124 may be any suitable arrangement and may include an arrangement that provides different zones of flexibility.

Cell 122 may be configured to expand. Cell 124 may be configured to expand. Cell 122 may be expanded by expansion of expandable web 106. Cell 124 may be expanded by expandable web 108.

Cell 122 may be configured to receive any suitable anchor, such as anchor 126. Cell 124 may be configured to receive any suitable anchor such as anchor 126. Anchor 126 may be configured to penetrate expandable web 106 and/or expandable web 108. Anchor 126 may penetrate expandable web 106 and/or expandable web 108 at two or more locations (not shown).

Implant 100 may include component 128. Component 128 may extend longitudinally along axis LI. Component 128 may extend between distal hub 110 and proximal hub 130.

Figure 2:
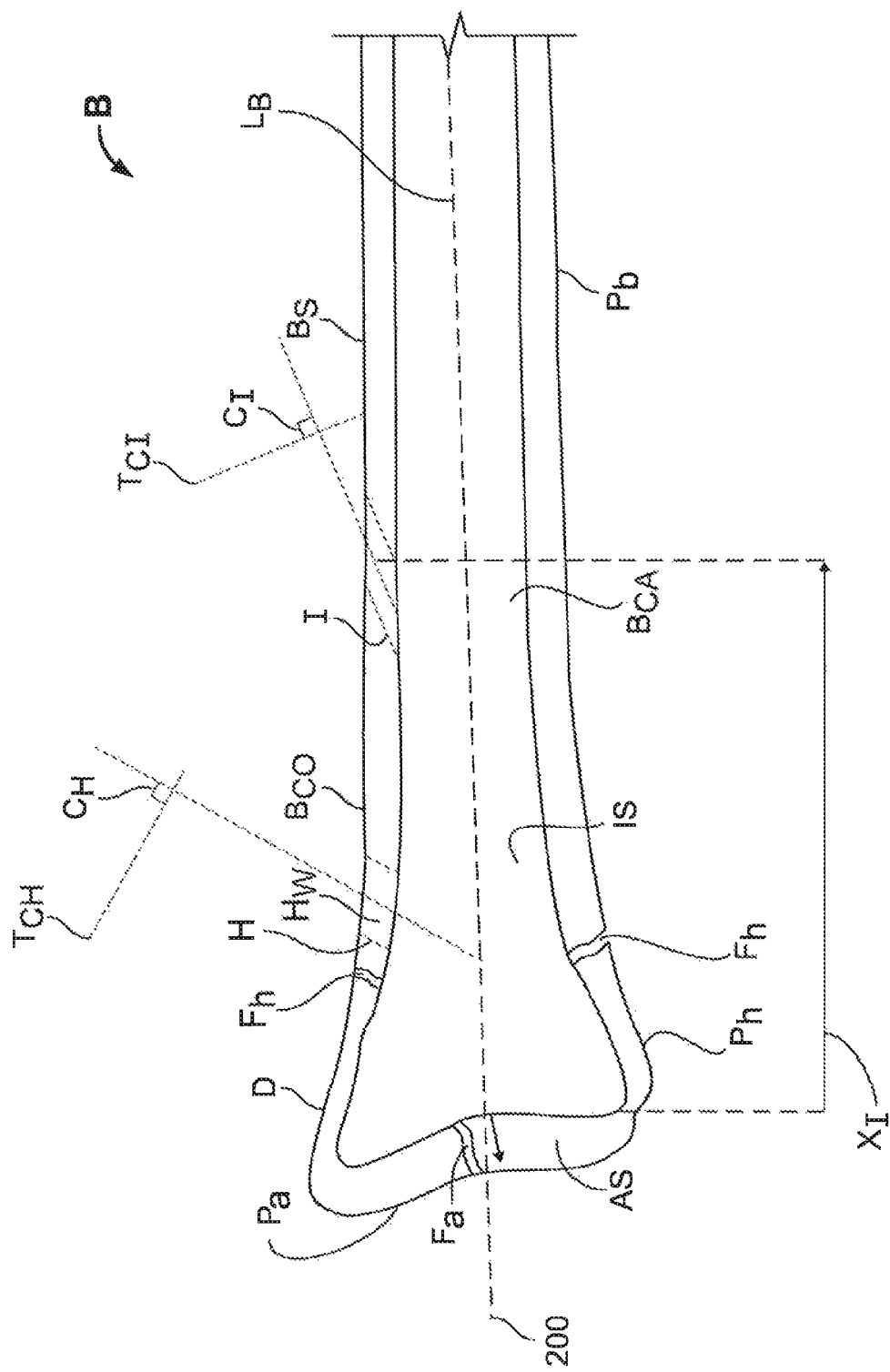
FIG. 2 shows illustrative anatomy in connection with which the invention may be practiced.

FIG. 2 illustrates anatomical features of a fractured bone B. An implant such as implant 100 may be deployed inside bone B to repair bone B.

Bone B is illustrated as a radius that is fractured at fractures Fh and Fa. Bone B includes bone portions Pb, Ph and Pa in distal end D. Bone segment Pb is the largest portion of bone B. Bone segment Ph is a head portion of bone B. Bone segments Ph and Pa include articular surface AS. Bone portions Pb, Ph and Pa are separated or partially separated along fractures Fa and Fh. Fracture Fa transects articular surface AS. Fracture Fh transects head of bone B.

Bone B, shown in a cross section that includes approximate longitudinal axis LB, includes cortical bone BCO and cancellous bone BCA. Cortical bone BCO may have a bone surface BS. Deployment of an implant into distal end D of bone B may require an access hole. Deployment of the implant may require displacement of cancellous bone BCA. Inside the bone B, the implant may engage cancellous bone BCA. Engagement with cancellous bone BCA may secure the implant to bone B.

Bone B may be provided with access hole H in cortical bone BCO. Hole H may have a hole wall HW. Hole wall HW may be a site for securing a stabilizer such as stabilizer 302 (shown in FIG. 3) to bone B. Hole H may have central axis CH. Transverse axis TCH may be perpendicular to central axis CH.

Bone B may be provided with access hole I in cortical bone BCO. An apparatus inserted in access hole I, may be required to travel a distance xI through intermedullary space IS to reach a head portion of bone B. An apparatus inserted through hole I may require bending to travel through intermedullary space IS to reach a head portion of bone B.

Some of the implants shown and described herein may be deployed through hole H. Some of the implants shown and described herein may be deployed through hole I. An implant that is configured to be deployed through hole H may include features for securing the implant to bone tissue at or near hole H. An implant that is configured to be deployed through hole I may include features for enabling the implant to deform during the bending and expand for operational use. It will be understood that an implant may include securement features that are appropriate for the access hole through which the implant is to be deployed even though the implant is illustrated herein with a particular type of securement feature such as a stabilizer.

Figure 3:
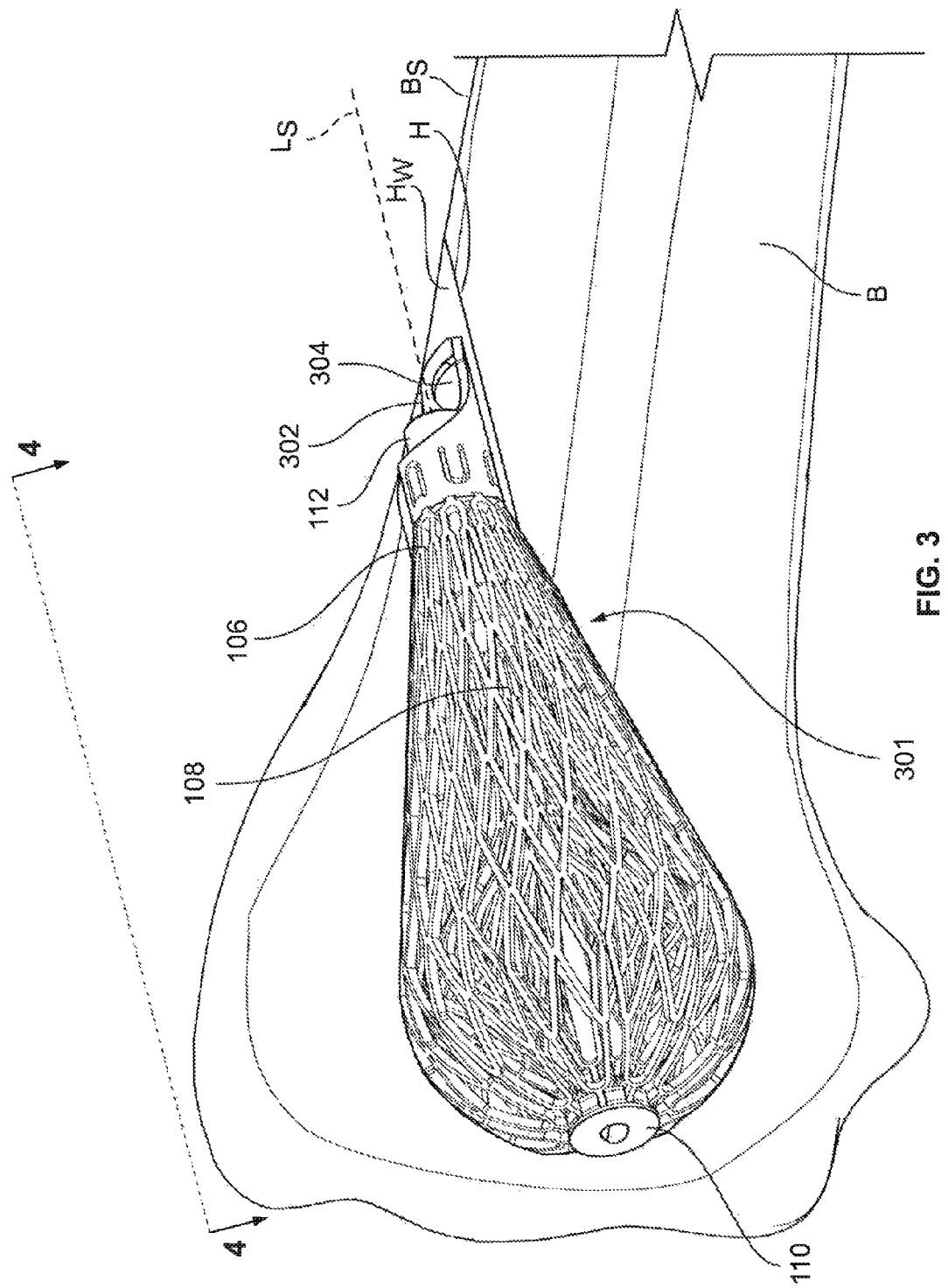
FIG. 3 shows another illustrative apparatus along with illustrative anatomy in accordance with principles of the invention.

FIG. 3 shows implant 301 deployed inside bone B. Bone B may have one or more features in common with bone B (shown in FIG. 1). Implant 301 may have one or more features in common with implant 100 (shown in FIG. 1). Longitudinal axis LI of implant 100 may correspond to central axis CH of hole H.

Stabilizer 302 may have one or more features in common with tail 103 (shown in FIG. 1). Stabilizer 302 may secure implant 301 to bone B. Stabilizer 302 may include anchor receiving feature 304. Anchor receiving feature 304 may be configured to receive an anchor (not shown) driven into hole wall HW.

Figure 4:
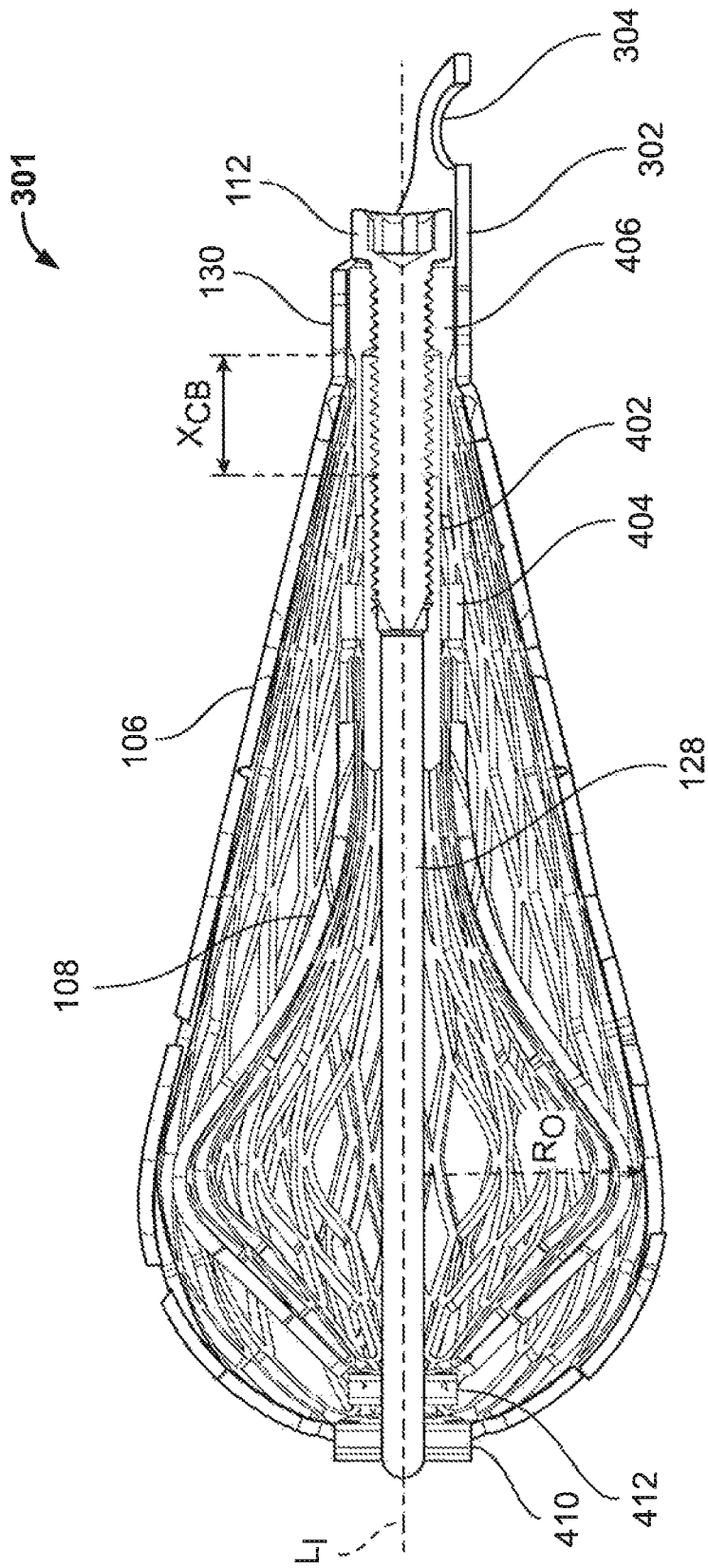
FIG. 4 shows a cross sectional view taken along lines 4-4 of the apparatus shown in FIG. 3.

FIG. 4 shows a view of a portion of implant 301 taken along lines 4-4 (shown in FIG. 3). Expandable web 106 may extend from proximal base 130 to distal base 410. Distal base 410 may include one or more of the features of distal hub 110. Distal base 410 may be longitudinally fixed to component 128.

Proximal base 130 may be longitudinally fixed to tapped cannulated body 406 using any suitable approach, such as tabs 118 (shown in FIG. 1). Tabs 118 may be biased to engage a pocket (not shown) in cannulated body 406.

Implant 301 may include proximal base 404. Expandable web 108 may extend from proximal base 404 to distal base 412. Distal base 412 may include one or more of the features of distal hub 120.

Implant 301 may include tapped cannulated body 402. Tapped cannulated body 402 may be longitudinally fixed to distal base 410.

Implant 301 may include locking screw 112. Locking screw 112 may be threaded. Locking screw 112 may threadedly engage tapped cannulated body 406 and/or tapped cannulated body 402. Locking screw 112 may fix distance xCB between tapped cannulated body 406 and tapped cannulated body 402.

Distance xCB fixed by locking screw 112 may correspond to an expansion radius RO of expandable web 106 from longitudinal axis LI. Distance xCB fixed by locking screw 112 may correspond to a therapeutic radius RO of expandable web 106. A therapeutic ration RO may reduce tension of implant on bone B.

Expandable web 108 may be slidable along axis LI and/or angularly displaceable about axis LI after distance xCB has been fixed.

Figure 5:
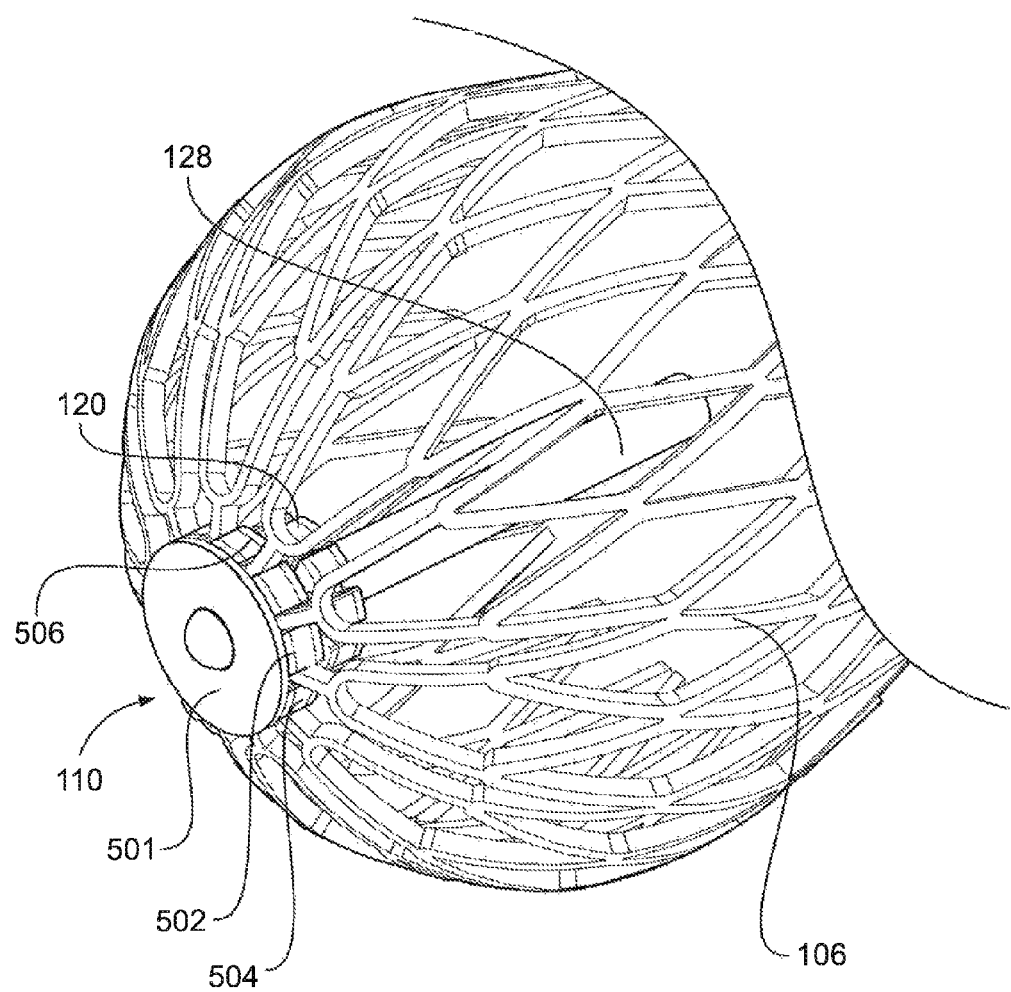
FIG. 5 shows a partial sectional view of the apparatus shown in FIG. 3.

FIG. 5 shows distal hub 110. Expandable web 106 may be fixed to distal hub 110. Distal hub 110 may have one or more of the feature of first distal base 410. Distal hub 110 may be configured for expandable web 106 to be angularly displaced about axis LI. Distal hub 110 may be longitudinally fixed to component 128. Distal hub 110 may be rotationally fixed to component 128.

Distal hub 110 may include end cap 501. End cap 501 may include a detent configured to limit angular displacement of expandable web 106 about axis LI. Distal hub 110 may include cap 502. Distal hub 110 may include enclosure member 504.

Figure 6:
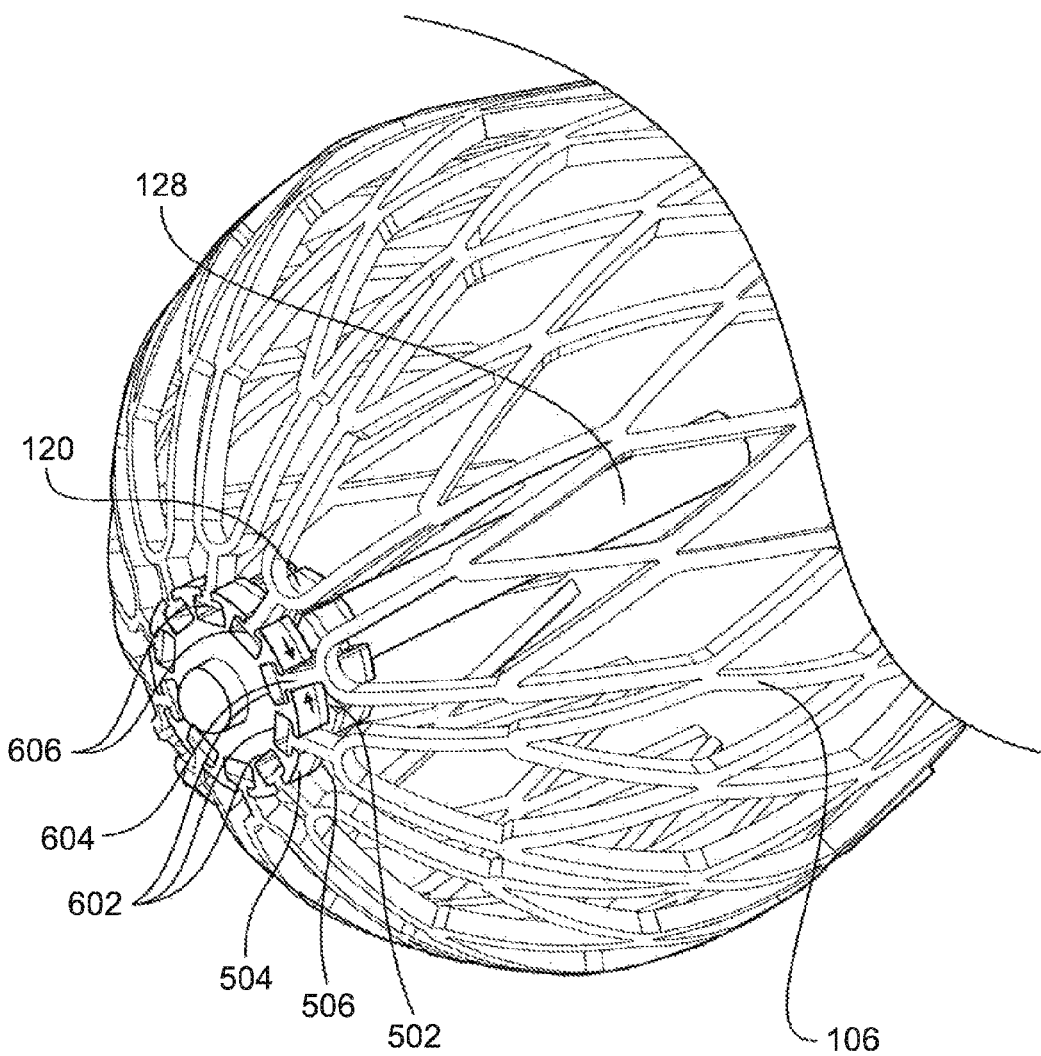
FIG. 6 shows a portion of the apparatus shown in FIG. 5.

FIG. 6 shows another embodiment of distal hub 110. Enclosure member 504 may include enclosures 602 configured to enclose tabs 606. Notch 604 may allow expandable web 106 an angular range of motion about axis LI. Angular motion of expandable web 106 about axis LI may correspond to an expansion or collapsing of expandable web 106.

Cap 502 may retain tab 602 in enclosure 504. Cap 502 may be notched to allow angular motion of expandable web 106 about axis LI. Cap 502 may include a notch (shown in FIG. 7A) for expandable web 106 to be collapsed about axis LI.

Figure 7A:
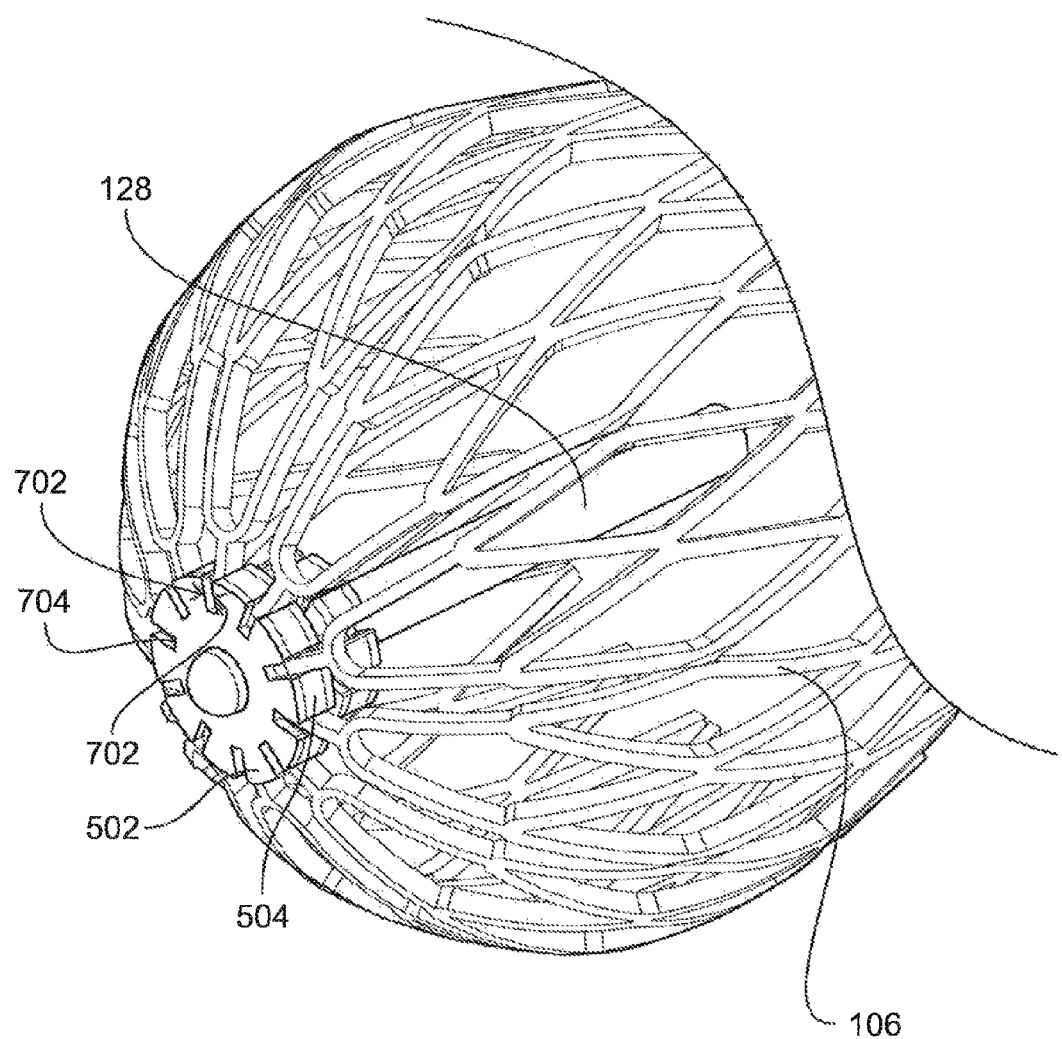
FIG. 7A shows a sectional view of an apparatus in accordance with the principles of the invention.

FIG. 7A shows another embodiment of distal hub 110. Cap 502 may include notch 702 for angular movement of expandable web 106 about axis LI. Angular movement of expansion web 106 about axis LI may be limited by an end 704 of notch 702. Cap 502 may retain tabs 606 in enclosure 504. Enclosure 504 and cap 502 may be configured for expandable web 106 to collapse about axis LI.

Figure 7B:
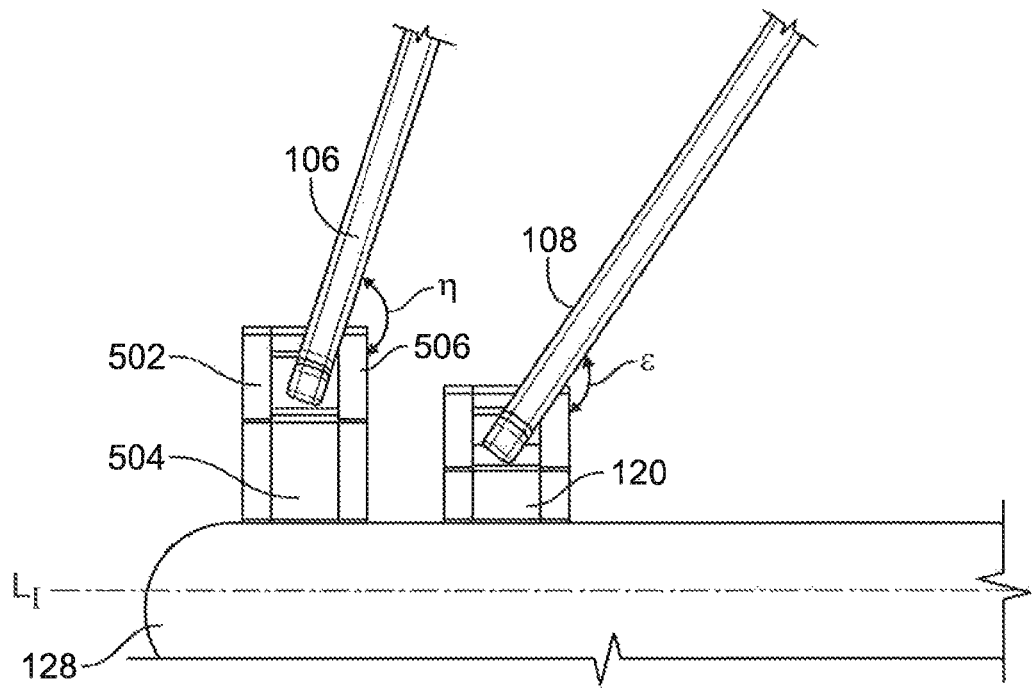
FIG. 7B shows a cross section of the apparatus shown in FIG. 5.

FIG. 7B shows a cross section of distal hub 110 and distal hub 120. Distal hub 110 may be configured for expandable web 108 to expand to angle η. Distal hub 120 may be configured for expandable web 108 to expand to angle ϵ. Angle ϵ may be greater than angle η. Distal hub 110 and distal hub 120 may be fix translation of an expandable web along axis LI. Distal hub 110 and distal hub 120 may allow rotation about axis LI. Distal hub 110 and distal hub 120 may allow expansion about axis LI. Distal hub 110 and distal hub 120 may be configured to provide different expansion radii (not shown) from axis LI.

Figure 7C:
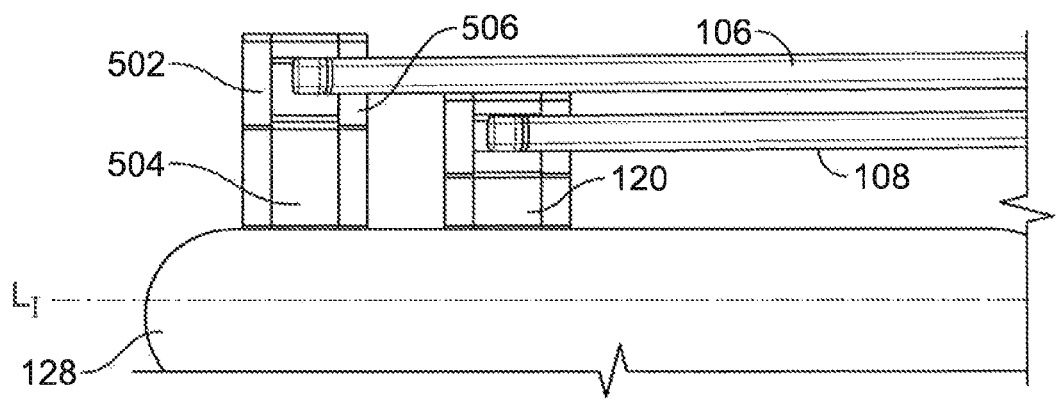
FIG. 7C shows a cross section of the apparatus shown in FIG. 5 in a state that is different from the state shown in FIG. 7B.

FIG. 7C shows a cross section of distal hub 110 and distal hub 120. Distal hub 110 and distal hub 120 may be configured for expandable web 106 and expandable web 108 to collapse upon each other. Distal hub 110 and distal hub 120 may be configured for expandable web 106 to be substantially parallel to expandable web 108 in a collapsed position.

Figure 8:
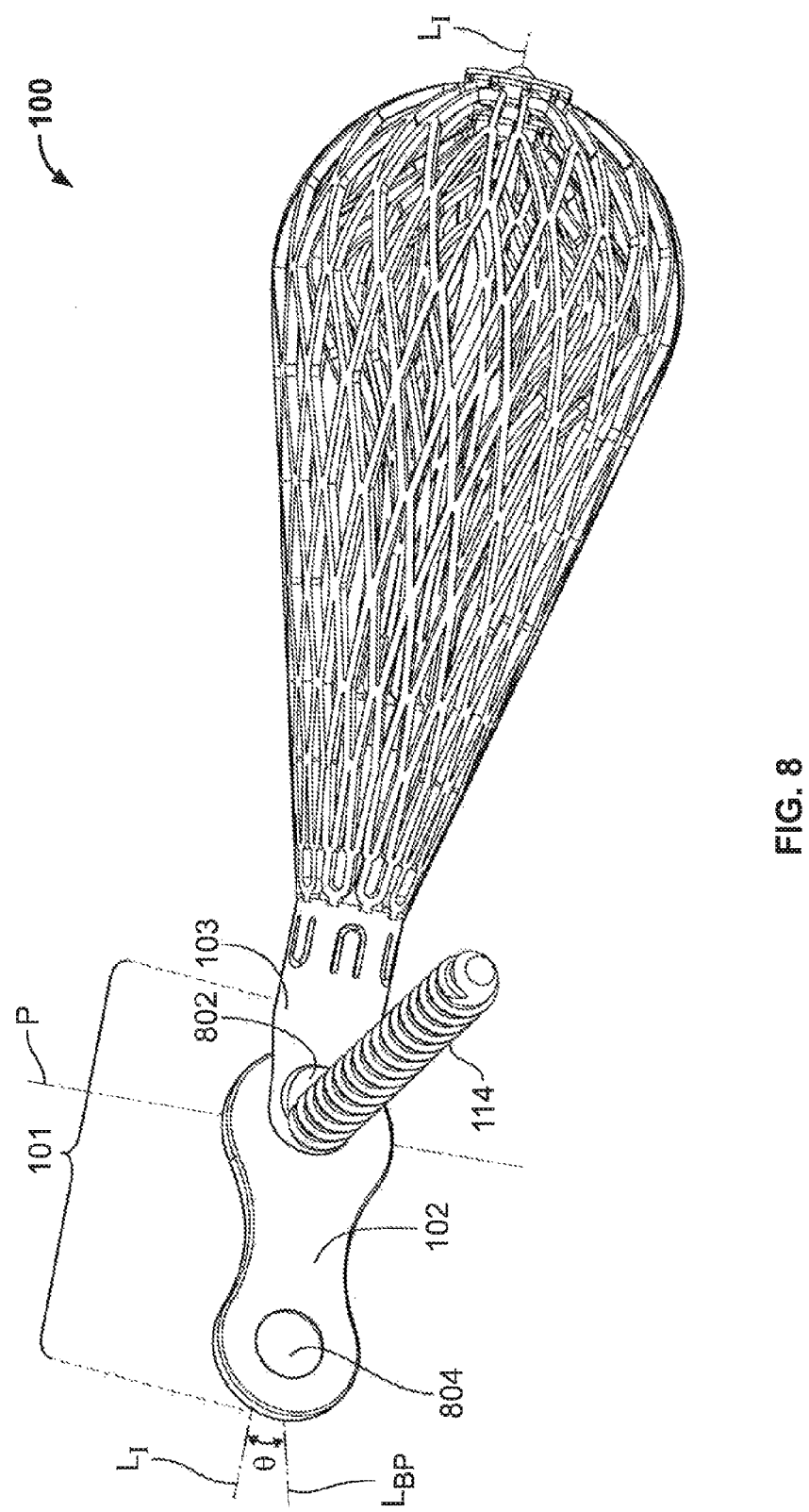
FIG. 8 shows a perspective view of the apparatus shown in FIG. 1 in a view different than the view shown in FIG. 1.

FIG. 8 shows illustrative stabilizer 101 for implant 100. Stabilizer 101 may include elongated member 103. Elongated member 103 may include anchor receiving feature 802. Anchor receiving feature 802 may be configured to receive anchor 114. Anchor 114 may be driven into hole wall HW (shown in FIG. 2). Anchor 114 may resist axial motion of elongated member 103 along longitudinal axis LI.

Stabilizer 101 may include a pivot axis P. Buttress plate 102 may resist rotation of elongated member 103 in hole H (shown in FIG. 2). Buttress plate 102 may resist rotation of elongated member 103 about an axis perpendicular to P. Longitudinal axis LI of implant 100 may be perpendicular to P. Central axis CH (shown in FIG. 2) of hole H may be perpendicular to P.

Buttress plate 102 may include anchor receiving feature 804. Anchor receiving feature 804 may be configured to receive an anchor driven into cortical bone BCO (shown in FIG. 2). Longitudinal axis LBP of buttress plate 102 may be parallel to bone surface BS. Bone surface BS and/or longitudinal axis LBP may be perpendicular to P. Anchor receiving feature 804 may receive anchor 116 (shown in FIG. 1).

Figure 9:
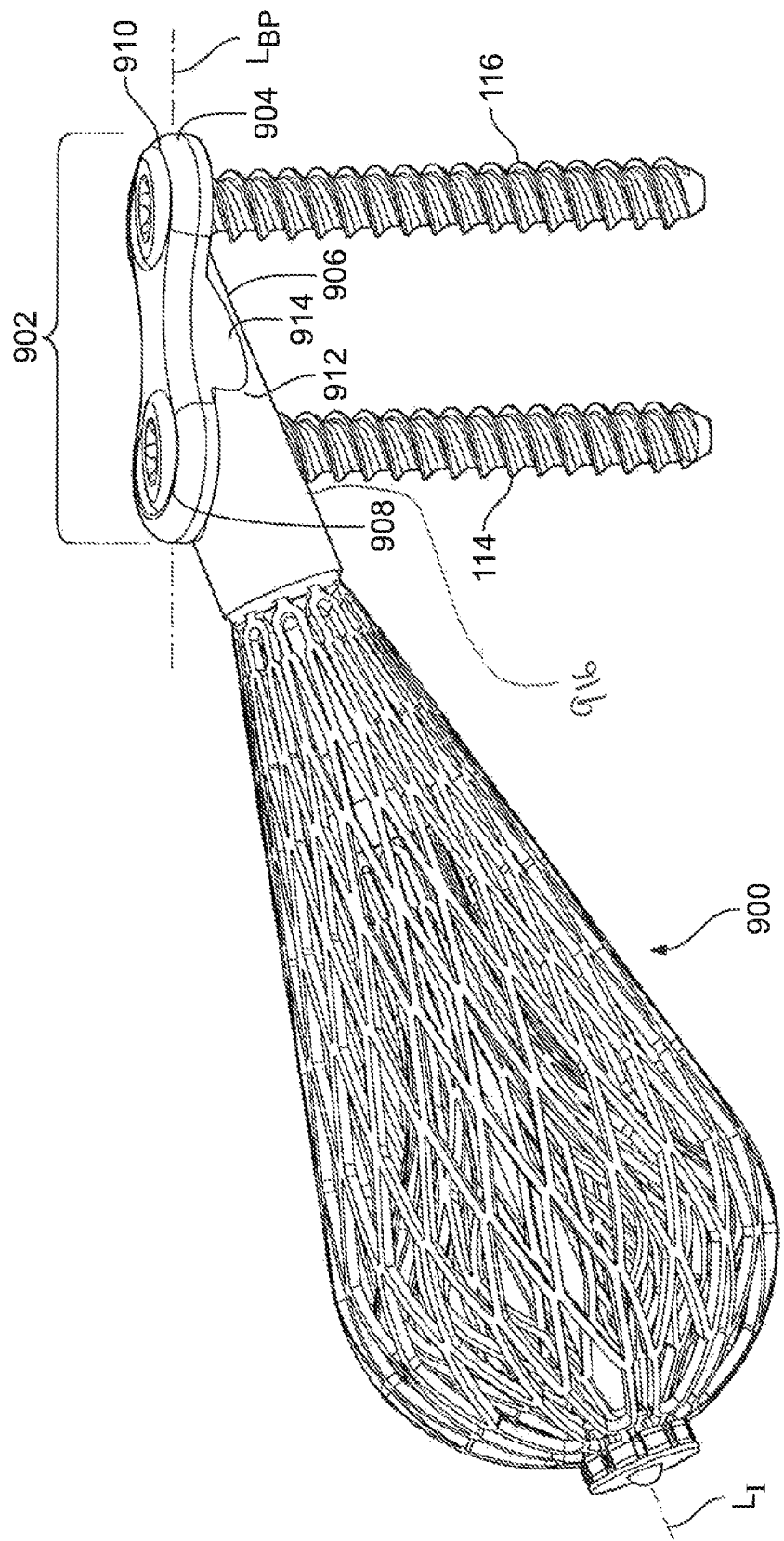
FIG. 9 shows a perspective view of an illustrative apparatus in accordance with principles of the invention.

FIG. 9 shows illustrative stabilizer 902. Stabilizer 902 may include elongated member 916. Stabilizer 902 may include elongated member 906. Stabilizer 902 may include buttress plate 904. Elongated member 906 may include extension 912. Buttress plate 904 may include extension 914.

Extension 912 may be configured to articulate with extension 914. Traction from anchor 114 received by anchor receiving feature 908 may be configured to brace the extension 912 against extension 914.

Stabilizer 902 may include anchor receiving feature 908. Anchor receiving feature 908 may be configured to receive and anchor driven into hole wall HW (shown in FIG. 2). Stabilizer 902 may include anchor receiving feature 910. Anchor receiving feature 910 may be configured to receive an anchor driven into an outer surface BS (shown in FIG. 2) of cortical bone BCO (shown in FIG. 2).

Anchor 114 may be driven through anchor receiving feature 908 into hole wall HW. Elongated member 906 may include an anchor receiving feature (not shown) configured to receive anchor 114. Anchor 116 may be driven through anchor receiving feature 910 into outer surface BS of cortical bone BCO. Longitudinal axis LBP of buttress plate 804 may be positioned such that longitudinal axis LBP is substantially parallel to bone surface BS. Longitudinal axis LBP of buttress plate 804 may be positioned such that longitudinal axis LBP is transverse to bone surface BS.

Stabilizer 902 may be configured to resist axial movement of implant 900 along longitudinal axis LI. Stabilizer 902 may be configured to resist angular rotation of implant 900 about longitudinal axis LI. Stabilizer 902 may be configured to resist rotation of implant 900 in hole H.

Figure 10:
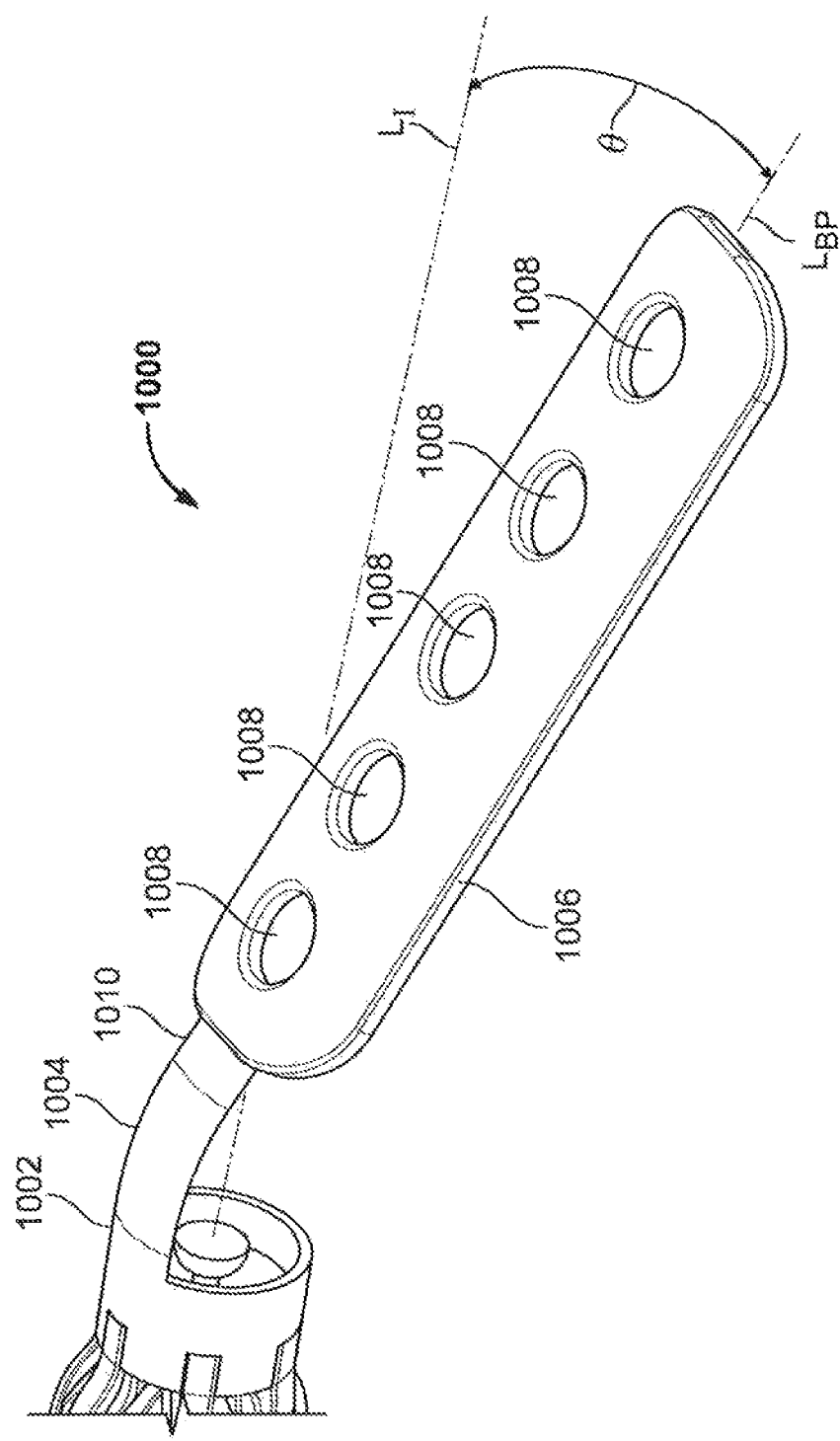
FIG. 10 shows a perspective view of an illustrative apparatus in accordance with principles of the invention.

FIG. 10 shows illustrative stabilizer 1000. Stabilizer 1000 may include elongated member 1004. Stabilizer 1000 may include buttress plate 1006. Buttress plate 1006 may include anchor receiving features 1008. Anchor receiving features 1008 may be configured to receive an anchor driven into a surface BS of cortical bone BCO.

Elongated member 1004 may be deformable. Elongated member 1004 may be deformed such that end 1002 is substantially parallel to longitudinal axis LI and end 1010 is substantially parallel to longitudinal axis LBP of buttress plate 1006. Deformation of elongated member 1004 may correspond to angle θ.

Figure 11A:
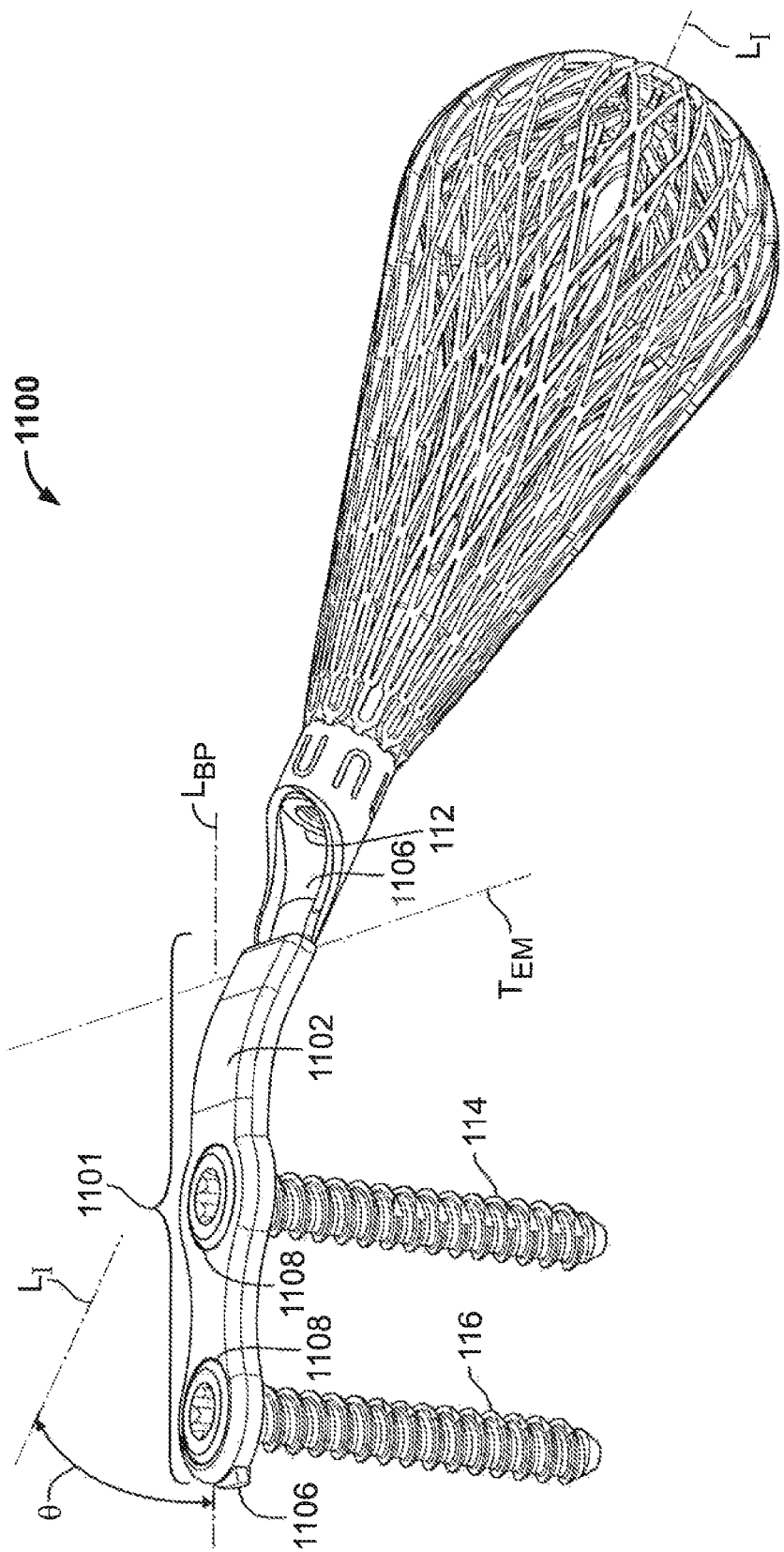
FIG. 11A shows a perspective view of an illustrative apparatus in accordance with principles of the invention.

FIG. 11A shows illustrative implant 1100. Implant 1100 may include stabilizer 1101. Stabilizer 1101 may include elongated member 1106. Elongated member 1106 may include one or more of the features of elongated member 1004. Stabilizer 1101 may include buttress plate 1102.

Buttress plate 1102 may be configured to be positioned over elongated member 1106. Buttress plate 1102 may be configured to resist rotation of elongated member 1106 about longitudinal axis LI. Implant 1100 may be inserted into hole H (shown in FIG. 2). Buttress plate 1102 may be configured to resist rotation of elongated member 1106 in hole H. Axis TEM is transverse to axis LBP. Buttress plate 1102 may be configured to resist transverse movement of elongated member 1106.

Buttress plate 1102 may include anchor receiving feature 1108. Anchor receiving feature 1108 may be configured to receive an anchor driven into an outer surface BS of cortical bone BCO (shown in FIG. 2). Elongated member 1106 may include a corresponding site for receiving an anchor driven through anchor receiving feature 1108.

Stabilizer 1101 may be configured for locking screw 112 to be adjusted after stabilizer 1101 has been secured to bone B (shown in FIG. 2).

FIG. 11B shows an illustrative view of stabilizer 1101 configured to restrict movement of elongated member 1106.

Figure 12:
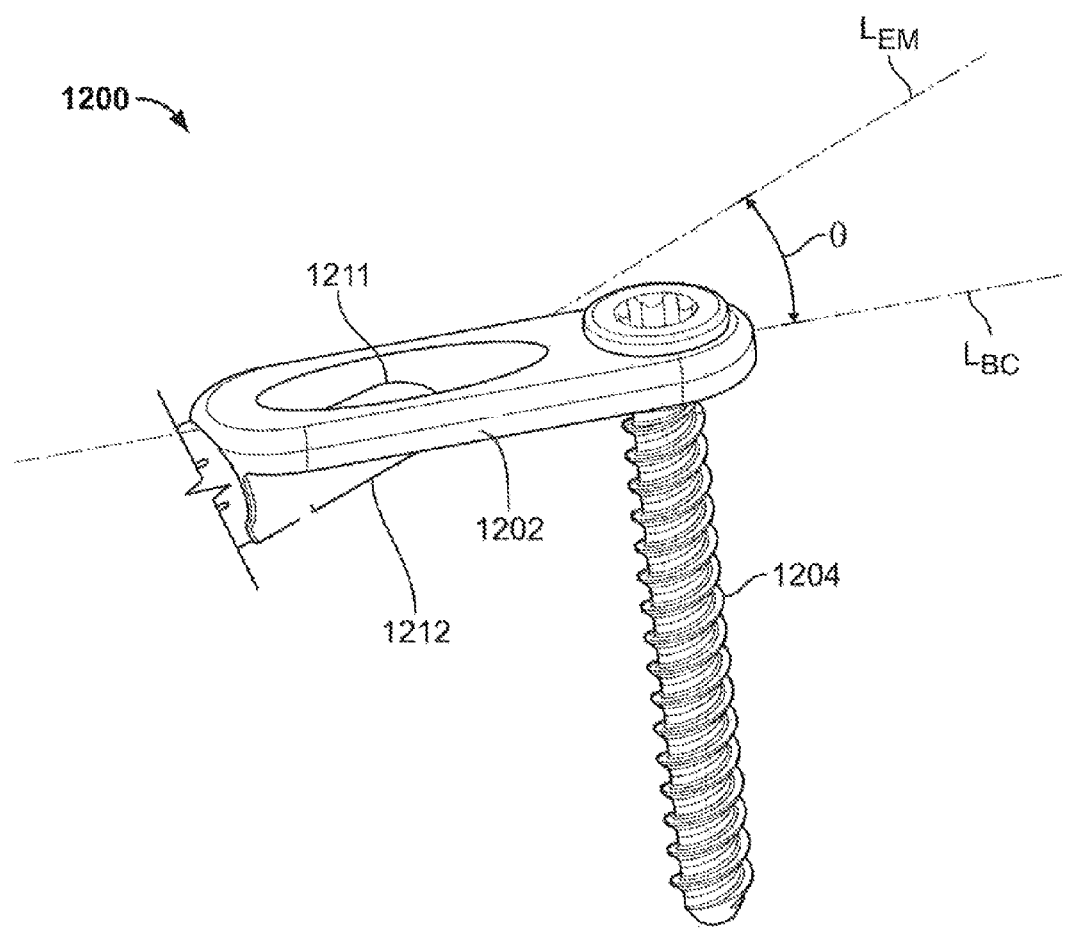
FIG. 12 shows a perspective view of an illustrative apparatus in accordance with principles of the invention.

FIG. 12 shows illustrative stabilizer 1200. Stabilizer 1200 may include elongated member 1212. Elongated member 1212 may extend from an implant (not shown) to buttress collar 1202. Elongated member 1212 may extend along hole wall HW (shown in FIG. 2). Elongated member 1212 may include longitudinal axis LEM. Longitudinal axis LEM may be substantially parallel to central axis CH of hole H and/or a longitudinal axis of an implant (not shown). Buttress collar 1202 may be supported at an opening of access hole H (shown in FIG. 2). Buttress collar 1202 may include a longitudinal axis LBC substantially parallel to bone surface BS (shown in FIG. 2).

Stabilizer 1200 may include an anchor receiving feature (not shown) configured to receive an anchor, such as anchor 1204, driven into bone surface BS. Stabilizer 1200 may include aperture 1211 for adjusting a locking screw (not shown). The locking screw may include one or more of the features of locking screw 112 (shown in FIG. 1).

Figure 13:
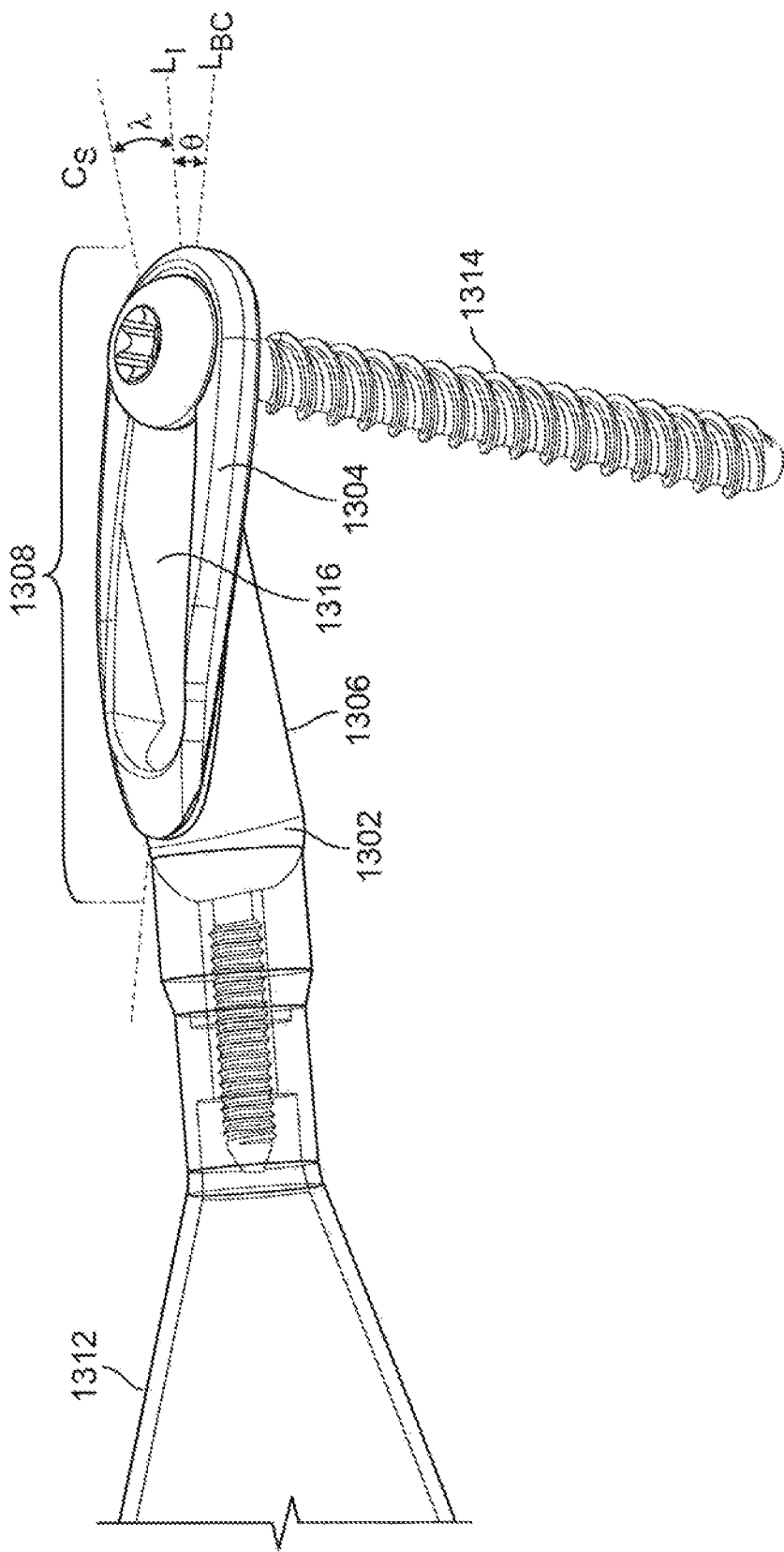
FIG. 13 shows a perspective view of an illustrative apparatus in accordance with principles of the invention.

FIG. 13 shows illustrative stabilizer 1308 for implant 1312. Stabilizer 1308 may include elongated member 1306. Stabilizer 1308 may include buttress collar 1304. Buttress collar 1304 may have longitudinal axis LBC. Longitudinal axis LBC may be substantially parallel to bone surface BS (shown in FIG. 2).

Implant 1312 may have longitudinal axis LI. Angle θ between axis LI and LBC may be adjustable. Elongated member 1306 may include articulating surface 1302. Articulating surface 1302 may be configured for stabilizer 1308 to engage implant 1312 at angle λ between central axis CS of stabilizer 1308 and longitudinal axis LI of implant 1312. Central axis CS may correspond to central axis CH of hole H (shown FIG. 2).

Angle λ may be fixed by a locking screw (not shown) inserted into aperture 1316. The locking screw may be configured to fix angle λ and an expansion (not shown) of implant 1312 from longitudinal axis LI. The locking screw may include one or more of the features of locking screw 112 (shown in FIG. 1)

Stabilizer 1308 may include an anchor receiving feature (not shown). The anchor receiving feature may be configured to receive anchor 1314. The anchor receiving feature may be configured to direct anchor 1314 into an outer surface BS of cortical bone BCO (shown in FIG. 2).

Figure 14:
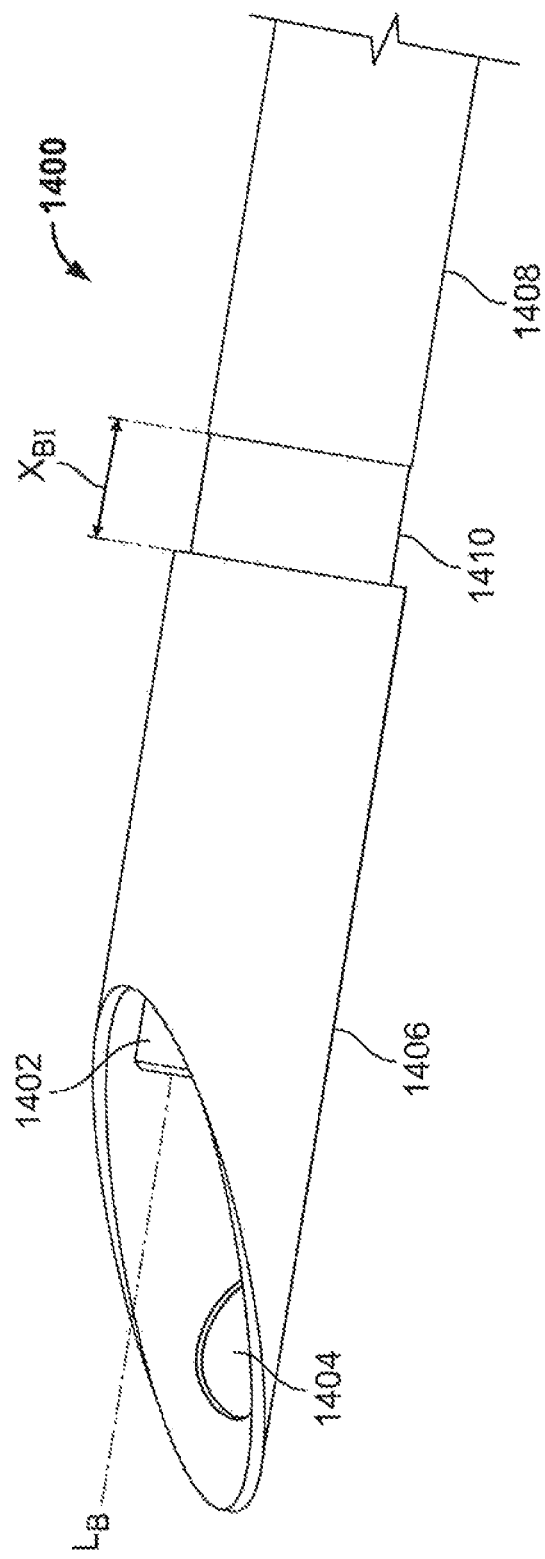
FIG. 14 shows a perspective view of an illustrative apparatus in accordance with principles of the invention.

FIG. 14 shows illustrative apparatus 1400 for implant 1408. Apparatus 1400 may include bracket 1406. Bracket 1406 may include anchor receiving feature 1404. Apparatus 1400 may include extension member 1410. Extension member 1410 may be configured to support bracket 1406 relative to implant 1408.

Apparatus 1400 may include locking screw 1402. Lock screw 1402 may be configured to fix bracket 1406 relative to implant 1408. Bracket 1406 may be fixed at a distance xBI from implant 1408. Bracket 1406 may be fixed at an angle relative to implant 1408.

Figure 15:
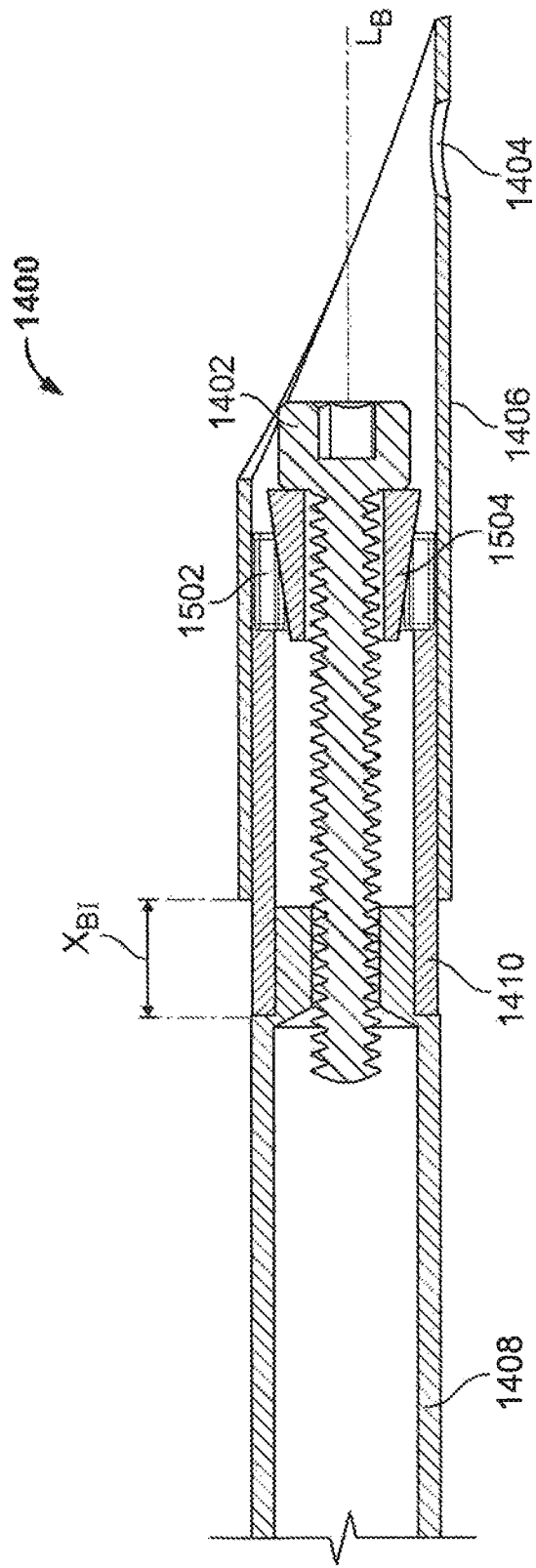
FIG. 15 shows a cross section of the apparatus shown in FIG. 14.

FIG. 15 shows a cross section of apparatus 1400. Apparatus 1400 may include expansion bushing 1504. Expansion bushing 1504 may be untapped. Extension member 1410 may include tabs 1502.

Locking screw 1402 may be configured to pass through expansion bushing 1504 and engage a tapped portion of implant 1408. Screw 1402 may be configured to drive expansion bushing 1504 toward implant 1408. Expansion bushing 1504 may be configured to press extension member 1410 toward implant 1408. Expansion bushing 1504 may be configured to expand tabs 1502.

Expansion of tabs 1502 may induce friction between extension member 1410 and bracket 1404. Friction between extension member 1401 and bracket 1404 may interfere with movement of bracket 1404 relative to implant 1408. Friction between extension member 1410 and bracket 1404 may fix rotation of bracket 1404 about axis LI relative to implant 1408. Friction between extension member 1410 and bracket 1404 may fix distance xBI between bracket 1406 and implant 1408.

Figure 16:
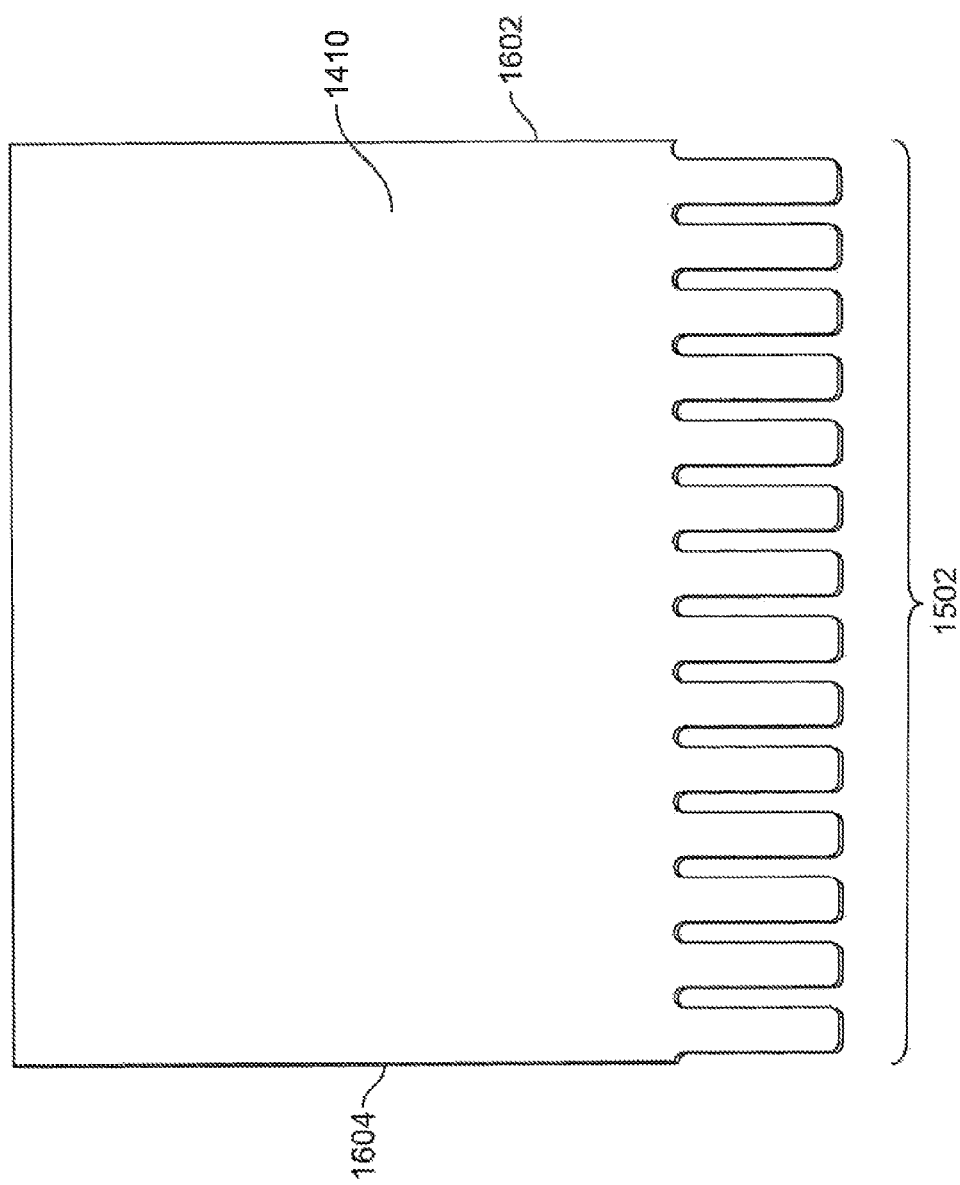
FIG. 16 shows information that may be used to manufacture apparatus shown in FIG. 15.

FIG. 16 shows illustrative extension member 1410. Extension member 1401 may include tabs 1502. Extension member 1410 may be rolled into a cylindrical shape. In a cylindrical configuration, edge 1604 may be contiguous with edge 1602.

Figure 17:
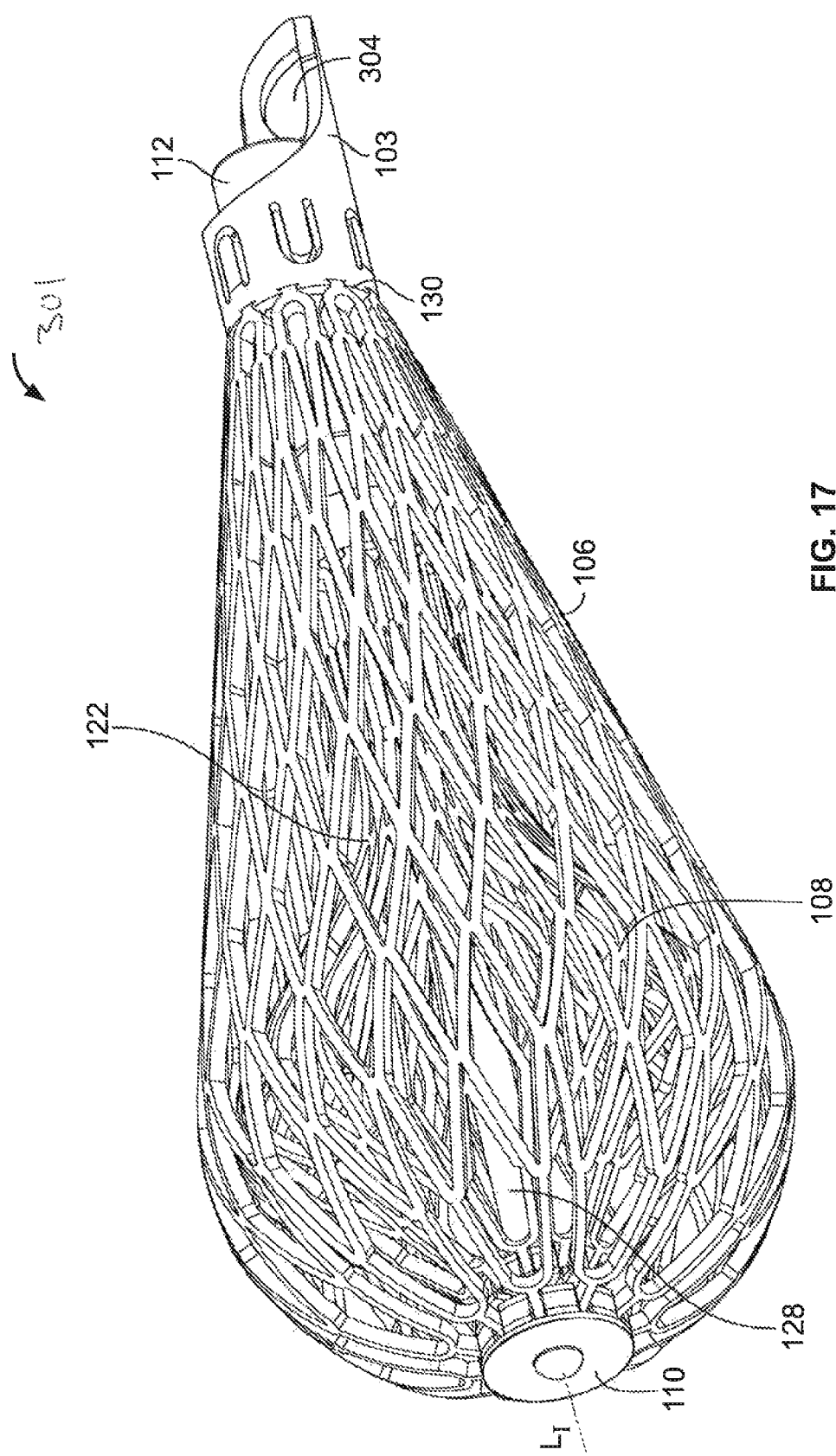
FIG. 17 shows another perspective view of the apparatus shown in FIG. 3.

FIG. 17 shows illustrative implant 301. Implant 301 may include expandable web 106 and expandable web 108. Expandable web 106 may be supported coaxially about implant component 128. Expandable web 108 may be supported coaxially about implant component 128. Expandable web 108 may be within expandable web 106.

Figure 40:
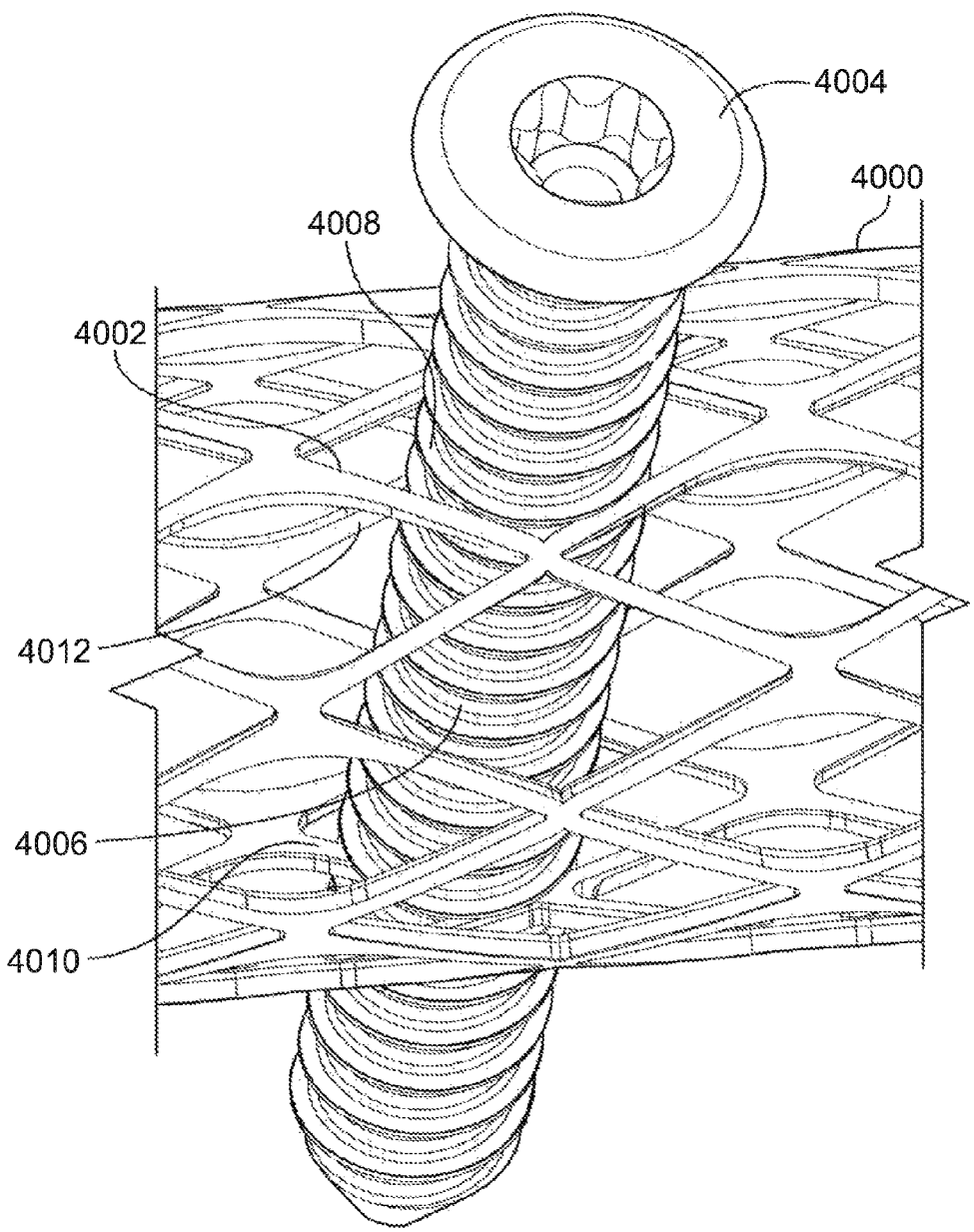
FIG. 40 shows a perspective view of an illustrative apparatus in accordance with principles of the invention.

Expandable web 106 may include a plurality of cells 122. Cells 122 may be configured to engage an anchor as shown in FIG. 40. The plurality of cells 122 may include any suitable density of cells 122. Expandable web 106 may include a density of cells 122 that varies along longitudinal axis LI of implant 301.

Figure 18:
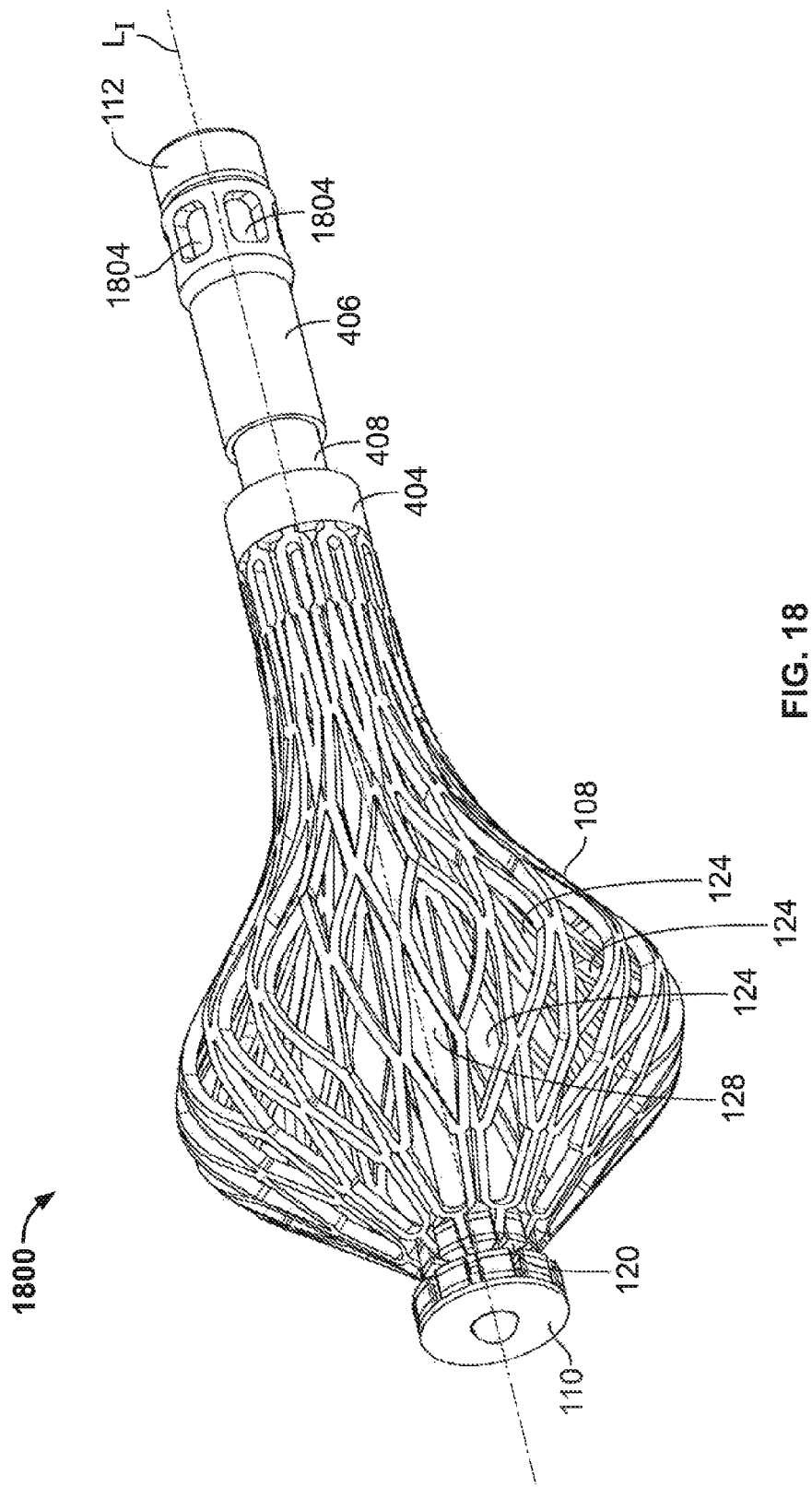
FIG. 18 shows a sectional view of the apparatus shown in FIG. 17.

FIG. 18 shows illustrative inner structure 1800 of implant 301. Inner structure 1800 may include expandable web 108. Expandable web 108 may include a plurality of cells 124. Cells 124 may be configured to engage an anchor as shown in FIG. 40. The plurality of cells 124 may include any suitable density of cells 124. Expandable web 108 may include a density of cells 124 that varies along longitudinal axis LI of implant 301. Expandable web 108 may be rotatably supported about axis LI.

Figure 19:
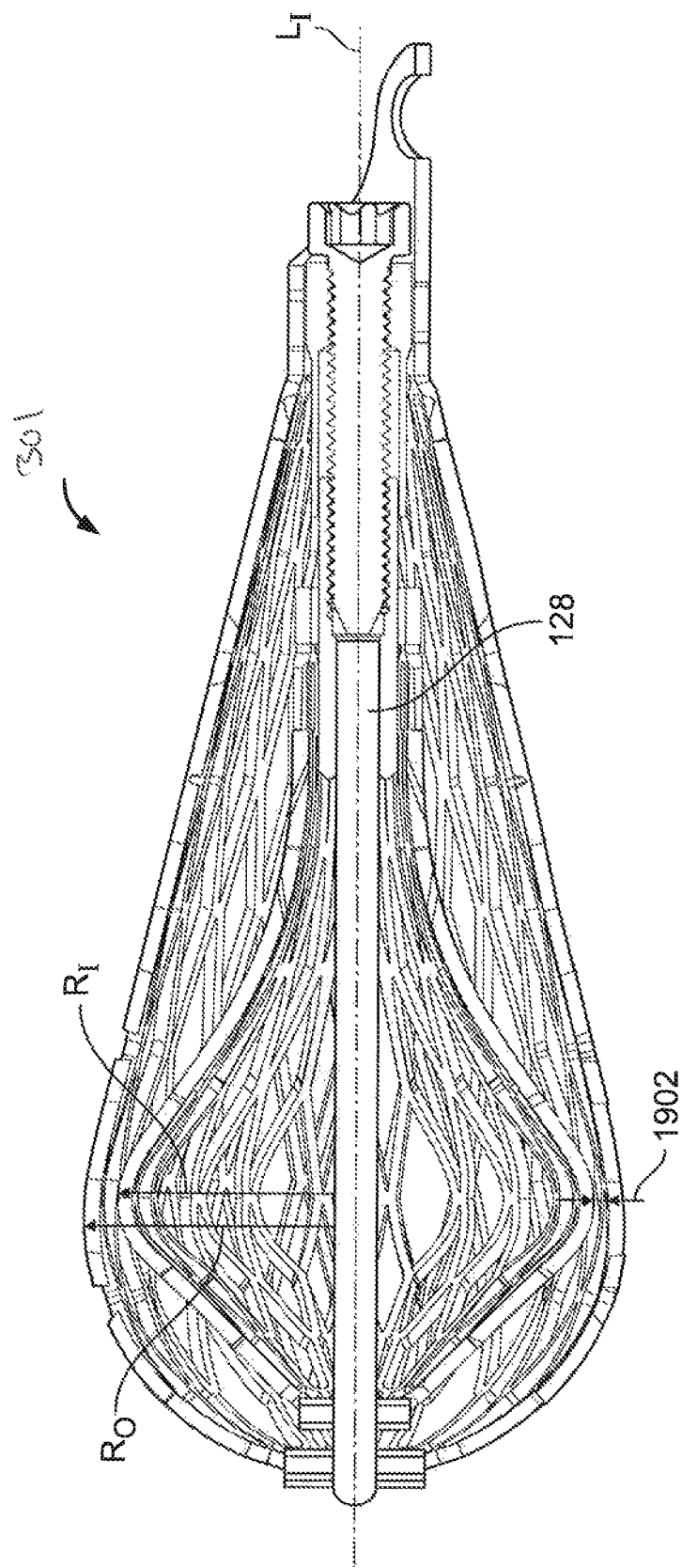
FIG. 19 shows a cross section of the apparatus shown in FIG. 17.

FIG. 19 shows a cross section of illustrative implant 301. Expandable web 106 may include any suitable density of cells 122. Expandable web 106 may include a density of cells 122 that varies along longitudinal axis LI such that expandable web has a radius RO.

Expandable web 108 may include any suitable density of cells 124. Expandable web 108 may include a density of cells 124 that varies along longitudinal axis LI such that expandable web has a radius RI. Radius RI may include a maximum value RI. A difference between RO and a maximum value RI may correspond to radial offset 1902. Radial offset 1902 may be configured to be sufficiently small such that when expandable web 106 bears a radial load (not shown), expandable web 106 may deform along radial offset 1902 to transmit the radial load to expandable web 108 at maximum value RI.

Figure 20:
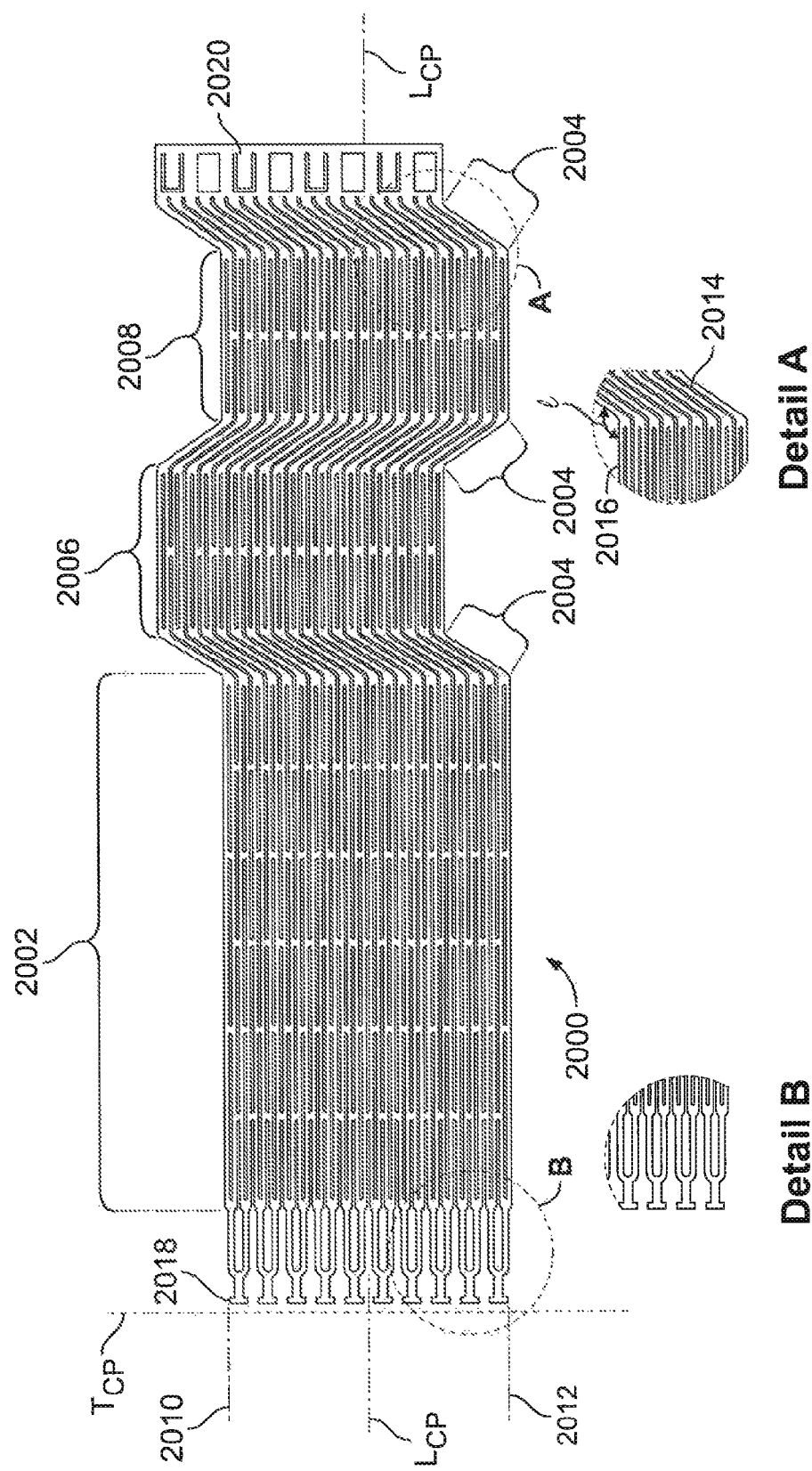
FIG. 20 shows a perspective view of an illustrative apparatus in accordance with principles of the invention.

FIG. 20 shows an illustrative cut pattern 2000 for an expandable web. Cut pattern 2000 includes distal end 2018. Cut pattern 2000 includes proximal end 2020. Cut pattern 2000 includes edge 2010. Cut pattern 2000 includes edge 2012.

Edge 2010 may be configured to abut edge 2012 to form a cylindrical shape about longitudinal axis LCP. "Rolling" cut pattern 2000 about axis LCP may correspond to an expandable web in a collapsed configuration. To achieve a "rolled" configuration cut pattern 2000 may be cut in a cylindrical tube.

Cut pattern 2000 may include zone 2002. Cut pattern 2000 may include zone 2004. Cut pattern 2000 may include zone 2006. Zone 2004 may include flexing members 2014. Zone 2002 may include collapsed cell pattern 2016. Zone 2006 may include a collapsed cell pattern with a higher cell density than zone 2002.

In a "rolled" configuration about axis LCP, flexing members 2014 of zone 2004 may be configured to have a less of a resistance to bending about transverse axis TCP perpendicular to axis LCP than collapsed cells 2016 of zone 2002

Increasing or decreasing a density of a collapsed cell pattern such as cell pattern 2016 may correspond to an increase or decrease of resistance to bending about axis TCP. Increasing or decreasing angle l between flexing members such as flexing members 2014 and a collapsed cell pattern such as collapsed cell pattern 2016 may corresponds to an increase or decrease in bending resistance.

Bending features of cut pattern 2000 may facilitate deployment of an implant based on cut pattern 2000 through a hole in a bone such as hole I.

Figure 21:
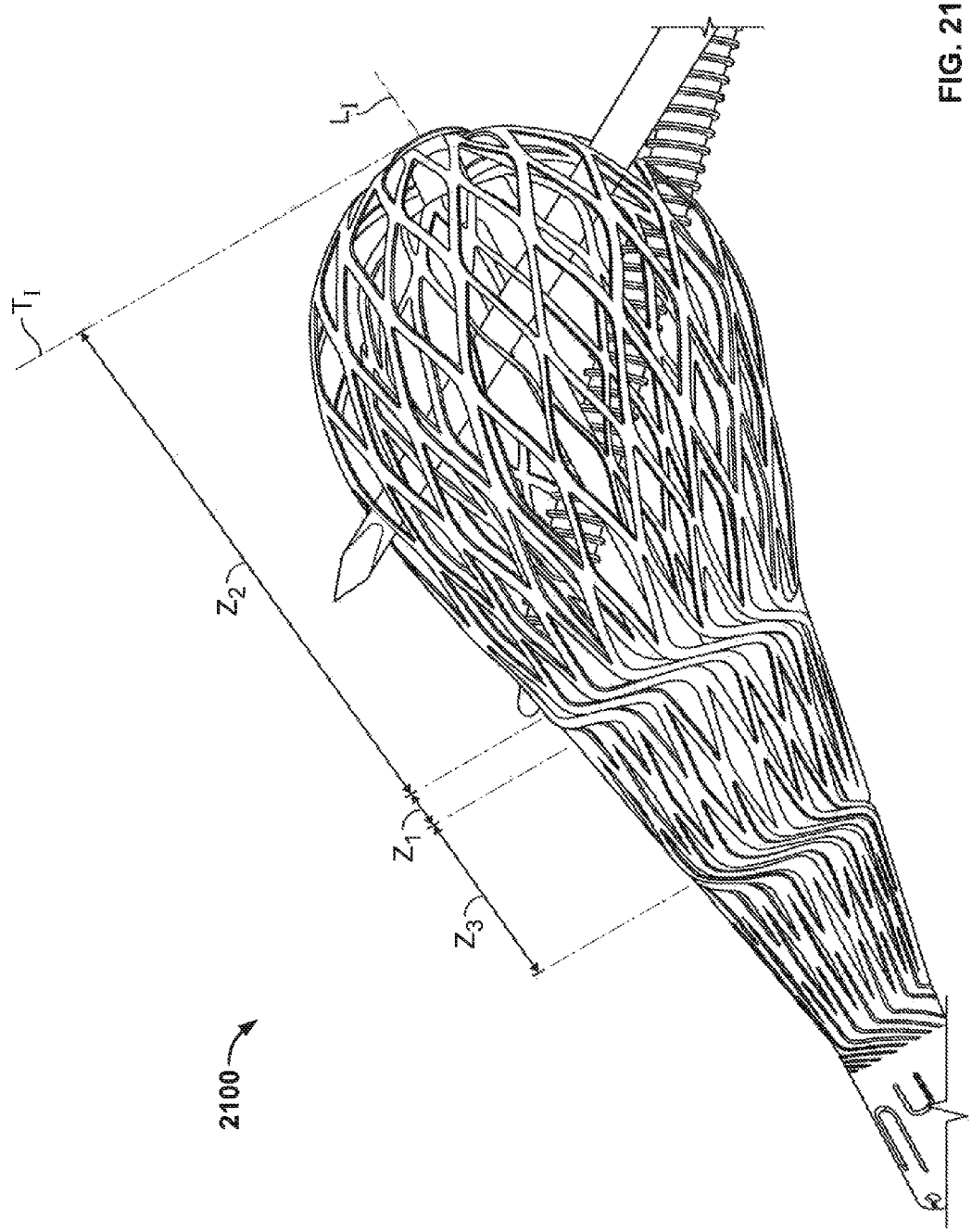
FIG. 21 shows information that may be used to manufacture apparatus in accordance with principles of the invention.

FIG. 21 shows illustrative expandable implant 2100. Implant 2100 may include one or more of the features of cut pattern 2000. Z2 may correspond to an expanded state of zone 2002 of cut pattern 2000. Z1 may correspond to an expanded state of zone 2004 of state of cut pattern 2000. Z3 may correspond to an expanded state of zone 2006 of cut pattern 2000.

In an expanded state, flex members of Z1 may provide axial stiffness to implant 2100. Under axial compression along LI, flex members of Z1 may stack upon each other and resist further compression along axis LI. In a compressed state, flex member of Z1 may facilitate deployment of an implant through a hole such as hole I.

Figure 22:
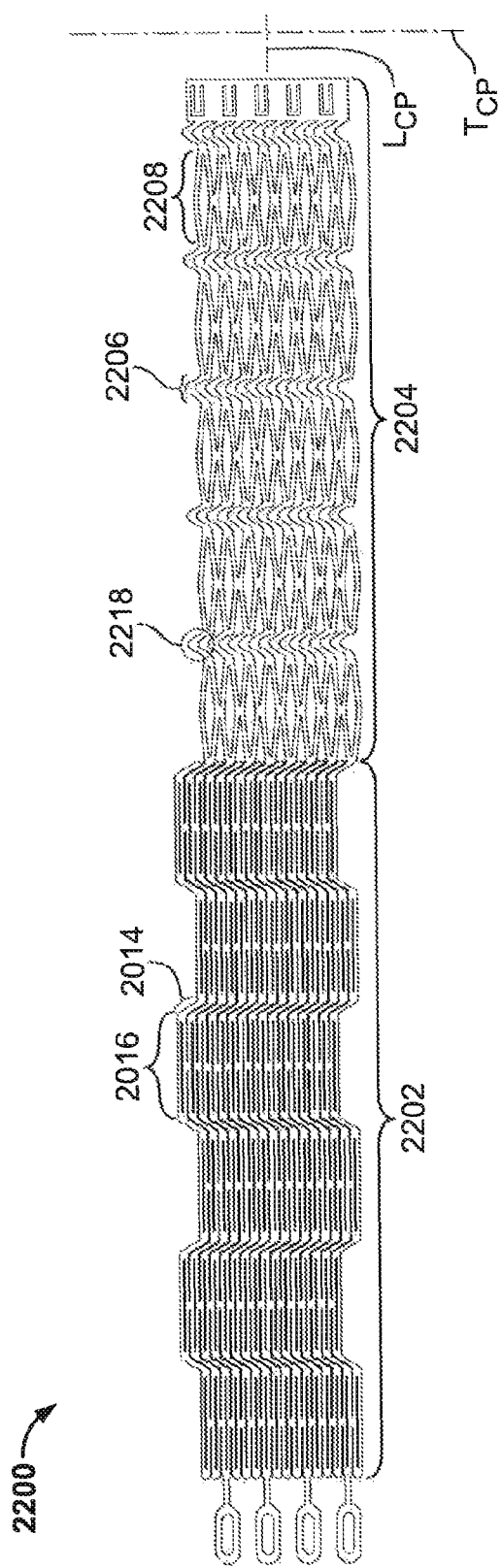
FIG. 22 shows information that may be used to manufacture apparatus in accordance with principles of the invention.

FIG. 22 shows illustrative cut pattern 2200. Cut pattern 2200 may be "rolled" about longitudinal axis LCP to form an expandable web, such as expandable web 106 and/or 108 in a collapsed state. To achieve a "rolled" configuration cut pattern 2200 may be cut in a cylindrical tube.

Cut pattern 2200 may include zone 2202. Cut pattern 2200 may include zone 2204. Zone 2202 may include a different cell density than zone 2204. Cell density of a zone may be configured to improve engagement with an anchor.

Zone 2204 may include flexing members 2206. Zone 2204 may include cell pattern 2208.

In a "rolled" configuration about axis LCP, flex member 2206 may have less of a resistance to bending about transverse axis TCP perpendicular to longitudinal axis LCP than cell pattern 2208. An increase or decrease in a length of legs of flex member 2218 may correspond to an increase or decrease in resistance to bending about axis TCP. An increase or a decrease in the angle between legs of flex member 2218 may correspond to an increase or decrease in resistance to bending about axis TCP.

In an expanded state, flex members 2206 may provide axial stiffness to an implant. Under axial compression along LCP, the legs of flex member 2218 may collapse about the apex, and resist further compression along axis LCP. Flex members 2206 may facilitate deployment of an implant through a hole such as hole I.

Figure 23A:
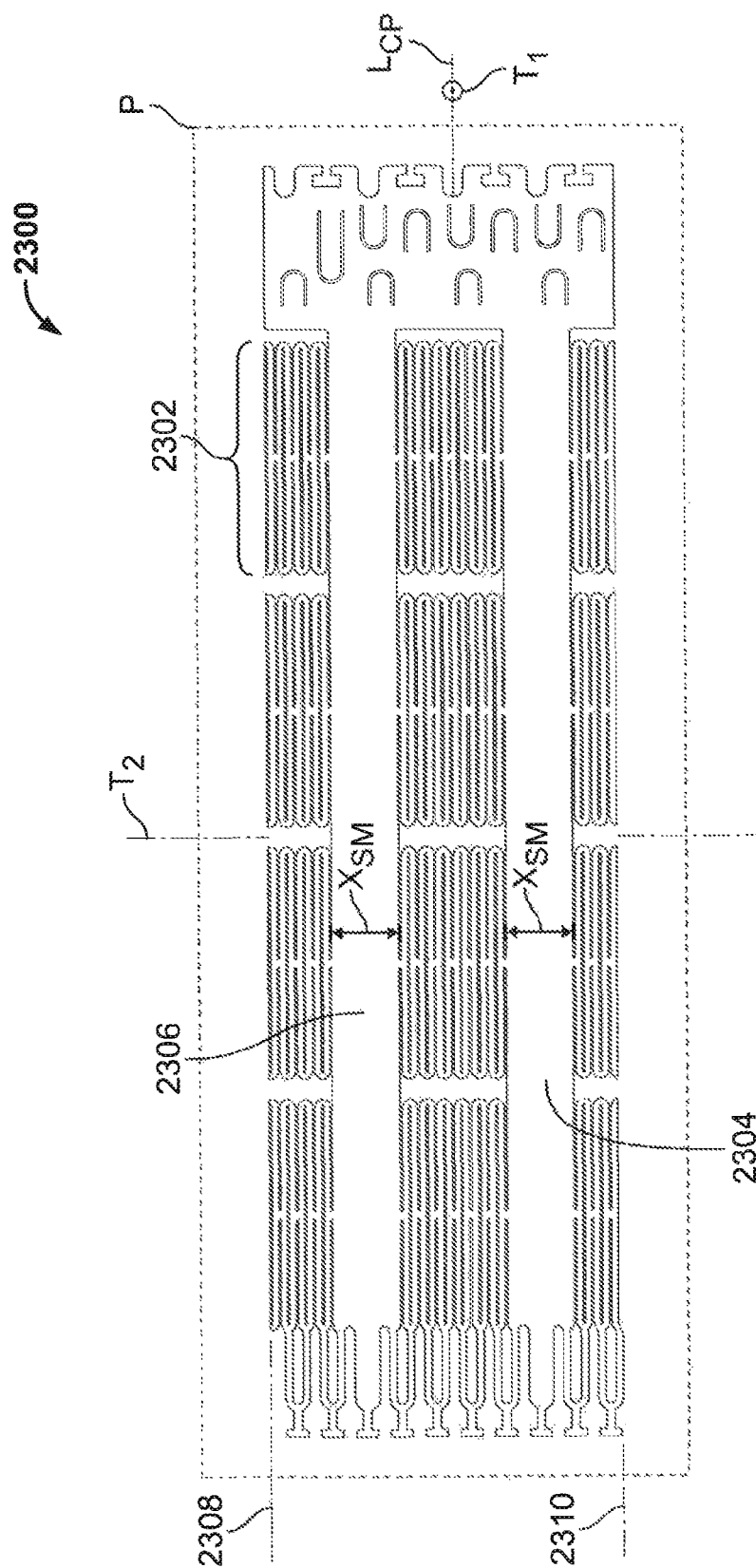
FIG. 23A shows information that may be used to manufacture apparatus in accordance with principles of the invention.

FIG. 23A shows illustrative cut pattern 2300. Cut pattern 2300 may include collapsed cell pattern 2302. Cut pattern 2300 may include support component 2306. Cut pattern 2300 may include support component 2304.

Cut pattern 2300, may lay flat in plane P. Cut pattern 2300 may be configured to be "rolled" about longitudinal axis LCP such that edge 2308 and edge 2310 are adjacent. To achieve a "rolled" configuration cut pattern 2300 may be cut in a cylindrical tube. Longitudinal axis LCP may correspond to a longitudinal axis of an implant, such as longitudinal axis LI of implant 100.

In a "rolled" configuration, cut pattern 2300 may be configured to expand and/or collapse about axis LCP. Width xSM of support component 2304 and width xSM of support component 2306 may be configured to lie perpendicular to plane P. Width xSM of support component 2304 and width xSM of support component 2306 may be configured to lie parallel to plane P.

Support component 2304 and support component 2306 may have a resistance to bending about transverse axis T1. Support component 2304 and support component 2306 may have a resistance to bending about transverse axis T2.

Transverse axis T2 may lie in plane P and may be perpendicular to axis LCP. Transverse axis T1 may be perpendicular to plane P and perpendicular to axis LCP. A bending resistance of support component 2304 about axis T2 may be different than a bending resistance of support component 2306 about axis T1.

When width xSM is configured to lie in and/or parallel to plane P, support component 2303 and support component 2306 may have a greater resistance to bending about axis T1 than a resistance to bending about axis T2. When width xSM is configured to be perpendicular to plane P, a bending resistance of support component 2304 and support component 2306 about axis T2 may be configured to be greater than the bending resistance about axis T1.

Width xSM may be configured to lie in and/or parallel to plane P when an implant, based on cut pattern 2300, is inserted in bone B through hole H (shown in FIG. 2). Width xSM may be configured to be perpendicular to plane P when an implant, based on cut pattern 2300, is expanded inside intermedullary space IS (shown in FIG. 2).

Support member 2304 may be configured to be rotatable with respect to plane independently of support member 2306. Support member 2306 may be configured to be rotatable with respect to plane independently of support member 2304. In one configuration, support member 2304 may lie in and/or parallel to plane P, and support member 2306 may be perpendicular to plane P.

Figure 23B:
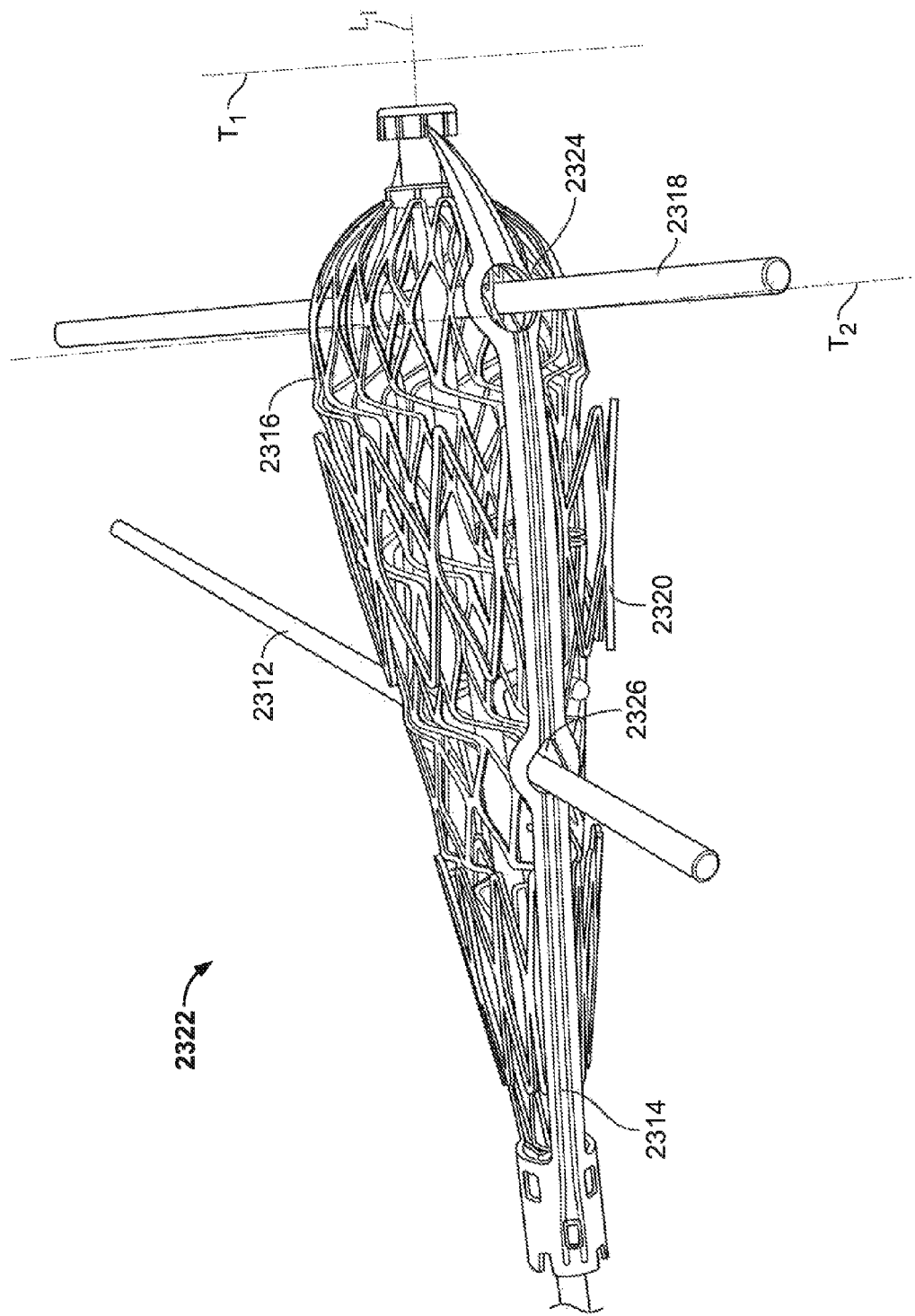
FIG. 23B shows a perspective view of an illustrative apparatus in accordance with principles of the invention.

FIG. 23B shows illustrative expandable implant 2322. Illustrative implant 2322 may include using cut pattern 2300 or any suitable cut pattern. Implant 2322 may include longitudinal axis LI. Implant 2322 may include inner expandable web 2316. Implant 2322 may include outer expandable web 2320. Implant 2322 may include support member 2314. Support member 2314 may define a plane, the plane including LI and transverse axis T2 perpendicular to LI.

Axis T2 is perpendicular to LI and perpendicular to the plane defined by T1 and LO. Support member 2314 may be more flexible about axis T1 than about axis T2.

Support member 2314 may include anchor receiving feature 2324. Anchor receiving feature may be configured to receive anchor 2318. Support member 2314 may include anchor receiving feature 2326. Anchor receiving feature 2326 may be configured to receive anchor 2314. Anchors 2314 and 2316 may be driven in a direction substantially parallel to the plane defined by LI and T2.

Implant 2322 may be orientated such that in a collapsed configuration a bending resistance about axis T1 is greater than a bending resistance about axis T2. Implant 2322 may be oriented such that in an expanded configuration, a resistance to bending about T2 is greater than a resistance to bending about axis T1.

For example, a multilayered implant such as implant 2322 may be orientated in one configuration in a collapsed configuration. The layers of implant 2322 may be rotated relative to each other when the layers are expanded or implanted in the bone. Relative rotation of the layers of implant 2322 may provide flexible in a plane while collapsed but rigid in the plane in the implanted and/or expanded state. Relative rotation of layers of an implant may facilitate insertion of the implant into a bone and/or implantation of the implant in a bone through a radiused path. Relative rotation of layers of an implant may facilitate insertion of the implant into a bone and/or implantation of the implant in a bone through a hole such as hole I.

FIG. 24A shows illustrative cut pattern 2400. Cut pattern 2400 may include structural member 2410. Cut pattern 2400 may include cross support 2402. Cut pattern 2400 may include cross support 2404. Cross support 2404 may include joint 2408. Cross support 2402 may include joint 2406.

Cut pattern 2400 may be configured to be expandable along axis ECP. Cut pattern 2400 may be collapsed along axis ECP. Cut pattern 2400 may be "rolled" about axis LCP. In a "rolled configuration" cut pattern 2400 may be expanded and/or collapsed about axis LCP. To achieve a "rolled" configuration cut pattern 2400 may be cut in a cylindrical tube.

Cross support 2402 may be configured to unfold about joint 2406 when cut pattern 2400 is expanded. Cross support 2404 may be configured to unfold about joint 2408 when cut pattern 2400 is expanded. Cross support 2402 may be configured to fold about joint 2406 when cut pattern 2400 is collapsed. Cross support 2404 may be configured to fold about joint 2408 when cut pattern 2400 is collapsed.

Figure 24B:
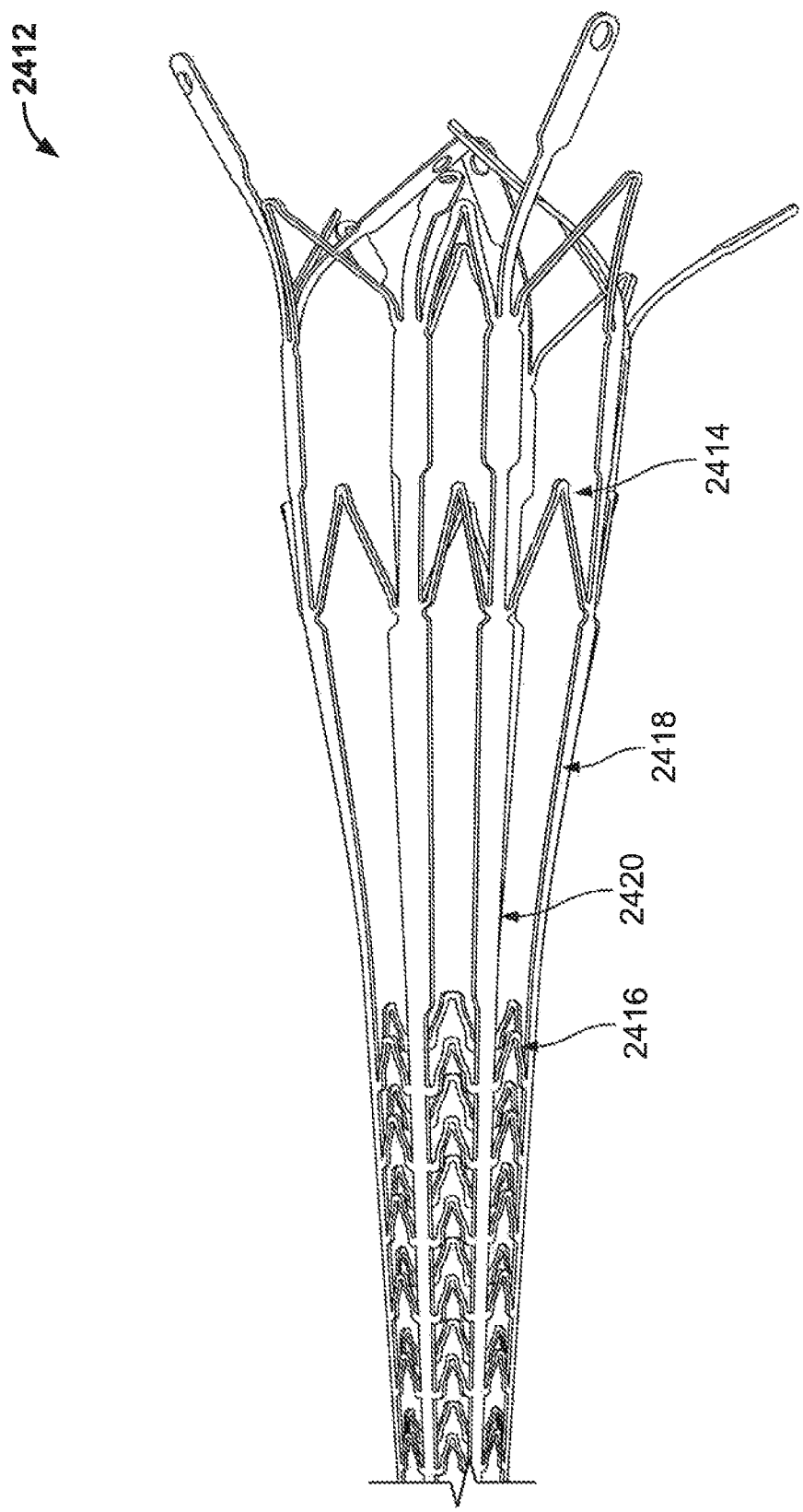
FIG. 24B shows a perspective view of an illustrative apparatus in accordance with principles of the invention.

FIG. 24B shows illustrative implant 2412. Implant 2412 may include structural member 2418. Implant 2412 may include structural member 2420. Implant 2412 may include cross support 2414. Implant 2412 may include cross support 2416. FIG. 24B shown cross supports 2414 and 2416 in between a folded and unfolded state.

Cross supports 2414 and 2416 may be folded to facilitate insertion of implant 2412 into a bone and/or implantation of the implant in a bone through a hole such as hole I. Cross supports 2414 and 2416 may be unfolded to increase axial stiffness of implant 2412.

Figure 25:
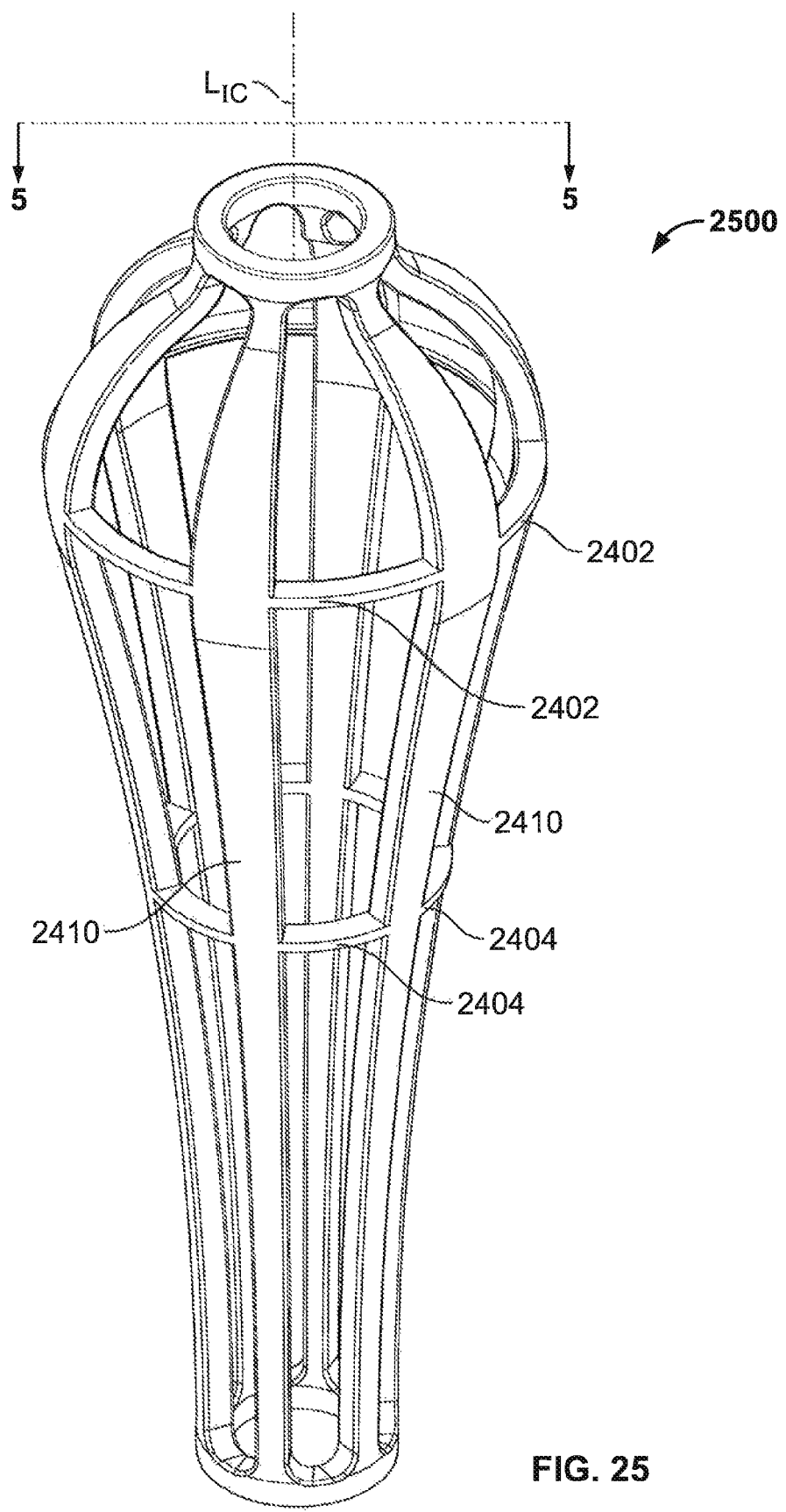
FIG. 25 shows a perspective view of an illustrative apparatus in accordance with principles of the invention.

FIG. 25 shows illustrative expandable implant component 2500. Implant component 2500 may include cross support 2402. Implant component 2500 may include cross support 2404. Implant component 2500 structural member 2410. FIG. 25 shows cross support 2402 in a configuration unfolded about joint 2406. FIG. 25 shows cross support 2404 in a configuration unfolded about joint 2408. In an unfolded configuration, cross support 2402 and/or 2404 may be configured to provide radial support for implant component 2500 about longitudinal axis LIC.

Cross supports 2402 and/or 2404 may be configured to limit a radial expansion of component 2500. Limiting an expansion of component 2500 may limit the buckling of structural support 2410 thereby increasing axial stiffness of the component 2500. In a collapsed state, folded cross supports 2402 and/or 2404 may facilitate insertion of the implant into a bone through a hole such as hole I.

Figure 26:
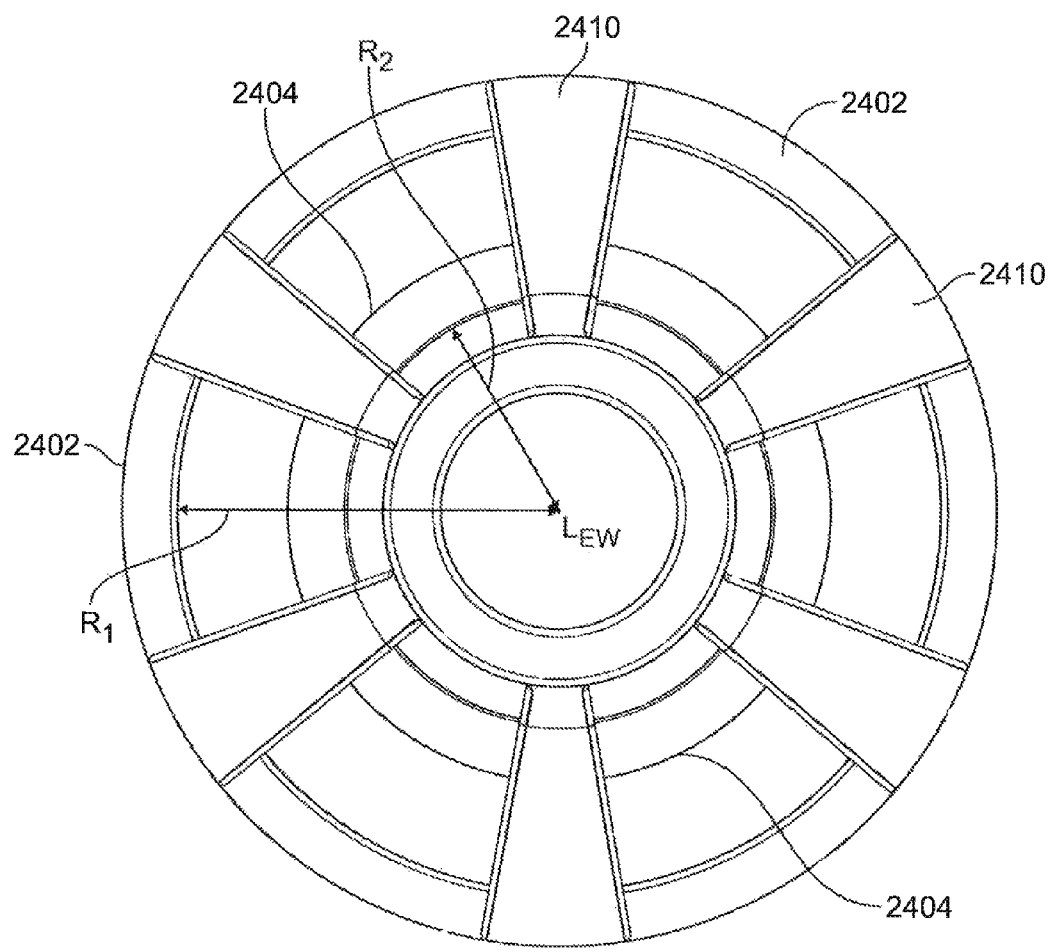
FIG. 26 shows a front view of the apparatus shown in FIG. 25.

FIG. 26 shows a view of implant component 2500 along lines 5-5. FIG. 25 shows implant component 2500 in an expanded state about axis LIC. Cross support 2402 may be configured to limit a radial expansion R1 of implant component 2500 from axis LEW. Structural component 2404 may be configured to limit a radial expansion R2 of implant component 2500 from axis LIC. Limiting an expansion of component 2500 may limit a "buckling" of structural support 2410 thereby increasing axial stiffness of the component 2500.

Figure 27:
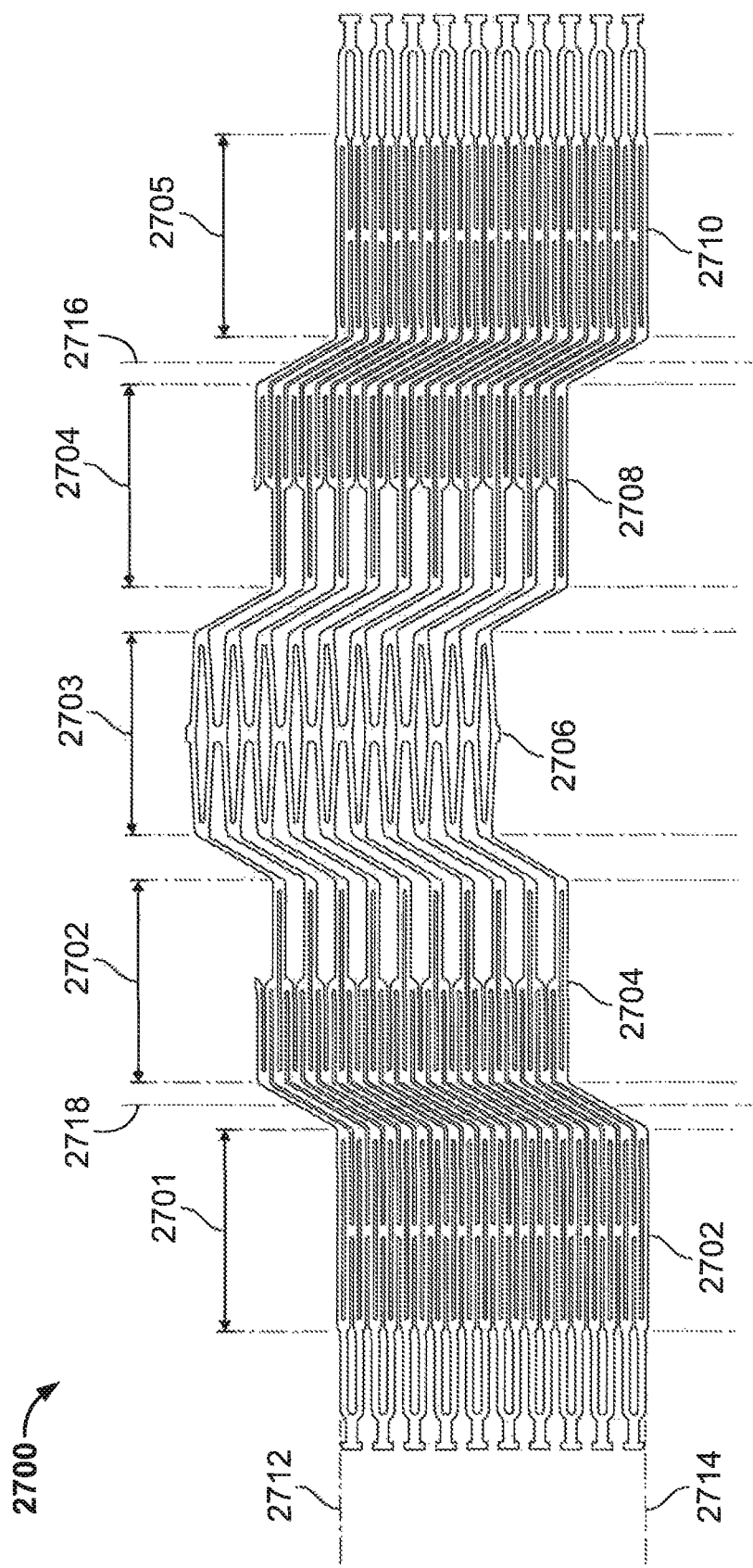
FIG. 27 shows information that may be used to manufacture apparatus in accordance with principles of the invention.

FIG. 27 shows illustrative cut pattern 2700. Cut pattern may be "rolled" about a longitudinal axis (not shown) such that edge 2712 is configured to be adjacent to edge 2714. In a "rolled" configuration, cut pattern 1700 may be expandable from the longitudinal axis.

Cut pattern 2700 may include cell density 2702 that varies longitudinally when segment 2701 is expanded about a longitudinal axis of an implant. Cut pattern 2700 may include cell density 2704 that varies longitudinally when segment 2704 is expanded about a longitudinal axis. Cut pattern 2700 may include cell density 2706 that varies longitudinally when segment 2703 is expanded about a longitudinal axis of an implant. Cut pattern 2700 may include cell density 2708 that varies longitudinally when segment 2704 is expanded about a longitudinal axis of an implant. Cut pattern 2700 may include cell density 2710 that varies longitudinally when segment 2705 is expanded about a longitudinal axis of an implant.

To achieve a "rolled" configuration cut pattern 2700 may be cut in a cylindrical tube.

Figure 29:
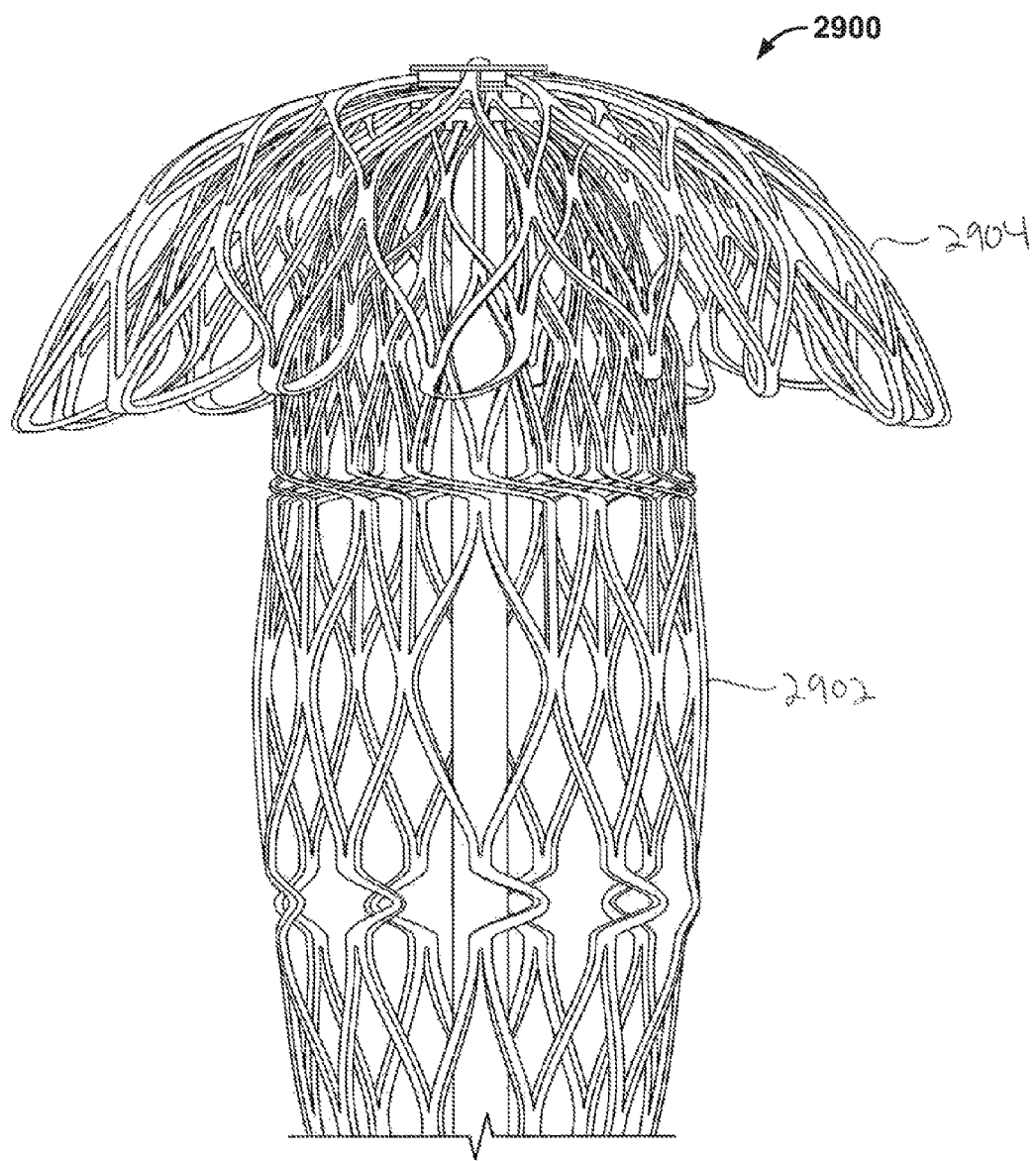
FIG. 29 shows a perspective view of an illustrative apparatus in accordance with principles of the invention.

FIG. 29 shows illustrative expandable implant 2900. Implant 2900 may be configured to expand into an "umbrella" shape. Illustrative implant 2900 may include proximal end 2902 and distal end 2904. Distal end 2904 may have an expansion radius that is larger than an expansion radius of proximal end 2902. Expandable implant 2900 may be based on a single expandable web.

A larger expansion radius may support fractured segments of bone B. A larger expansion radius may support non-fractured segments of bone B. Implant 2900 may fill, partially or completely intramedullary space IS inside bone B. Implant 2900 may be used if bone B does not contain sufficient cancellous bone BCA at the distal end of intramedullary space IS.

Implant 2900 may provide multiple points of contact for implant anchors, such as anchor 126, (shown in FIG. 1) on a single expandable web.

Figure 30:
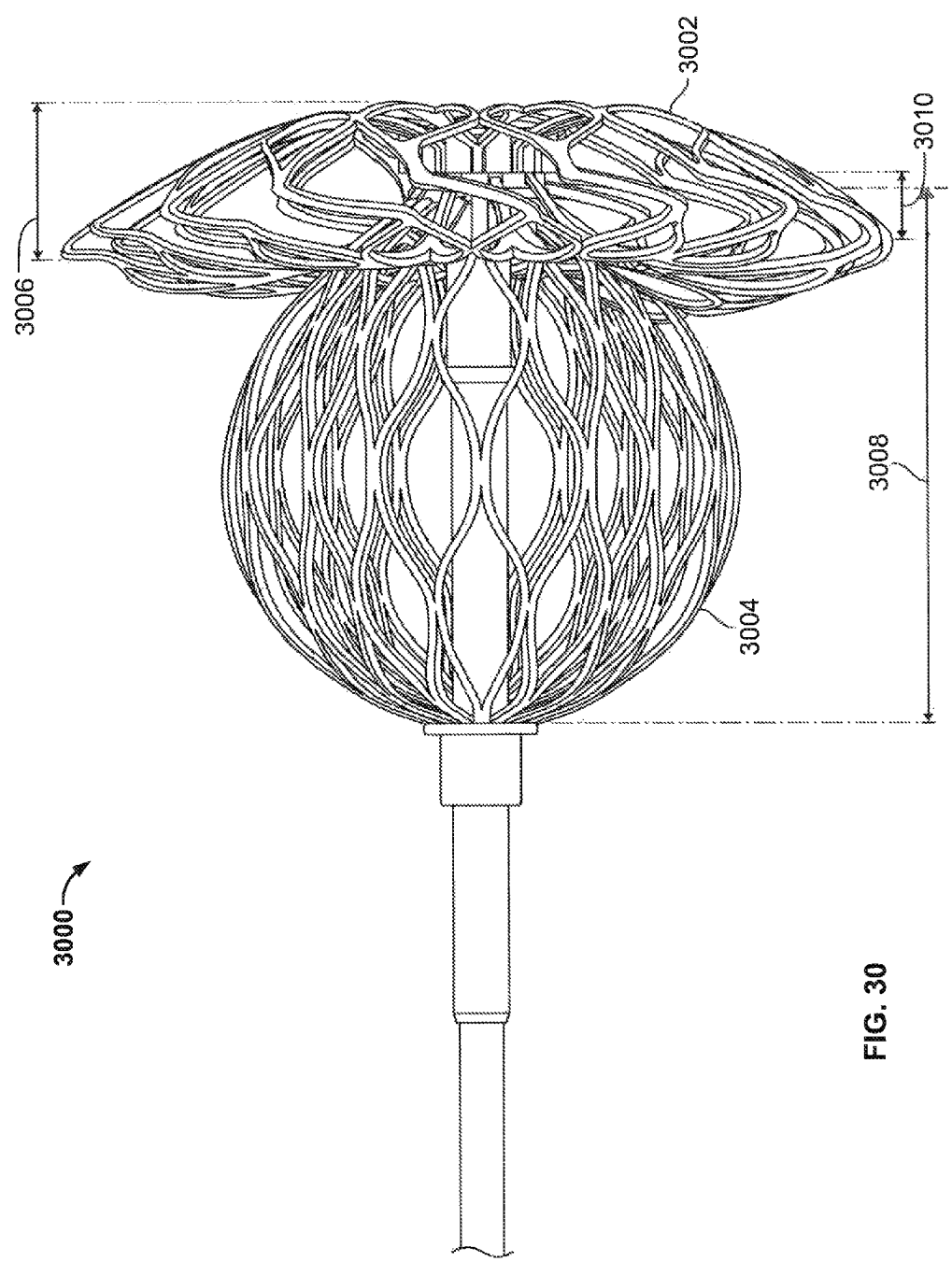
FIG. 30 shows a perspective view of an illustrative apparatus in accordance with principles of the invention.

FIG. 30 shows illustrative expandable implant 3000. Implant 3000 may be configured to expand into a "top hat" shape. Illustrative implant 3000 may include proximal member 3002 and distal member 3004. Distal member 3004 may have an expansion radius that is larger than an expansion radius of proximal member 3002. Implant 30 may include one or more of the features of implant 29.

Implant 3000 may include one expandable web having different cell densities when expanded from a longitudinal axis LI. Implant 3000 may include a first segment 3008 that is configured to expand into a profile that is ellipsoidal.

Implant 3000 may include a third segment 3006 that is configured to expand into a profile that is concave facing the first segment. Implant 3000 may include a second segment 3010 that is configured to expand into a profile that bridges from an outer radius of the third segment to an adjacent tip of the first segment.

Implant 3000 may include two or more expandable webs configured to form the "top hat" shape. The two or more expandable webs may be fixed to implant 3000 using distal hubs 110 and/or 120 (shown in FIG. 1).

Figure 31A:
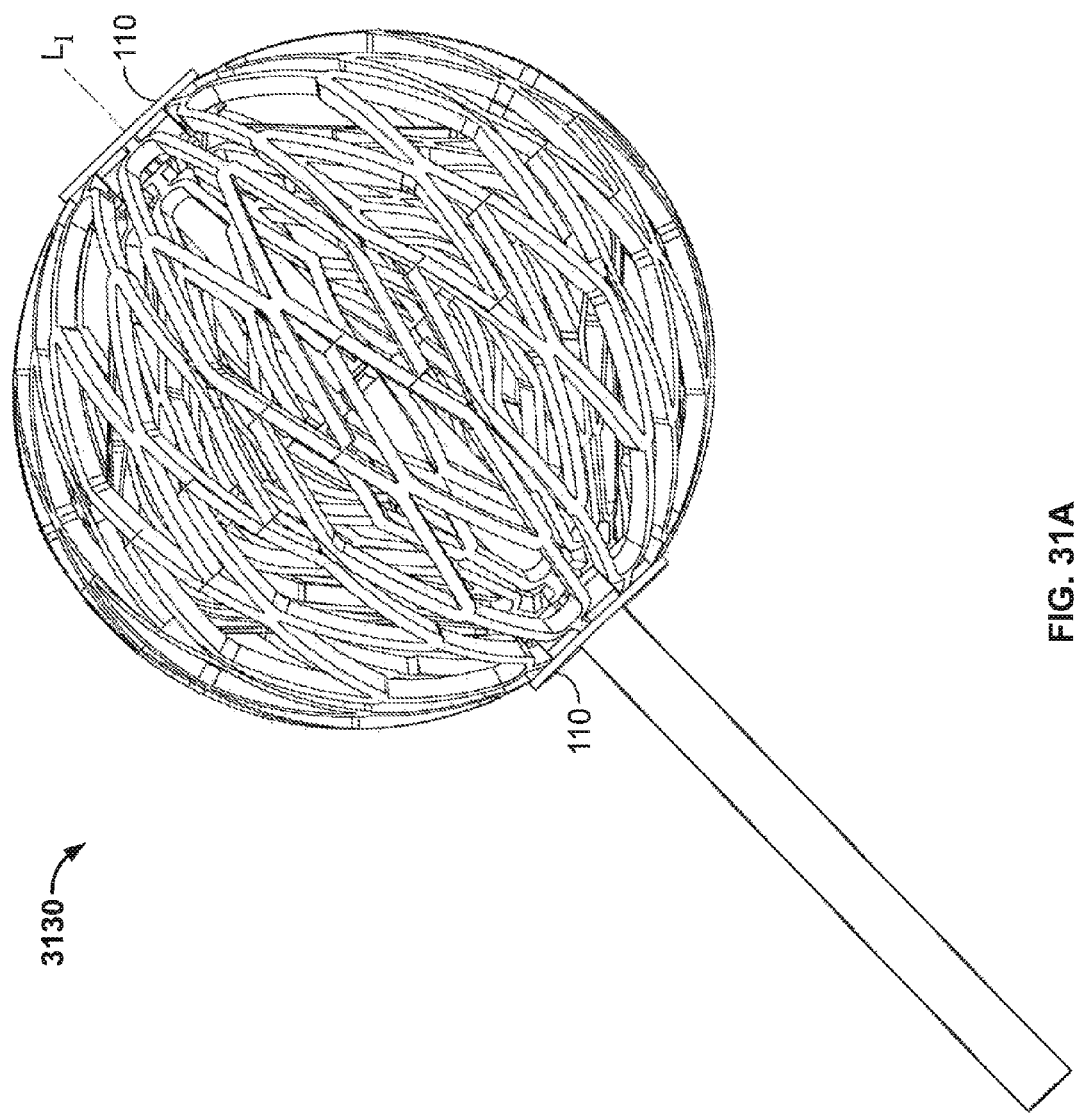
FIG. 31A shows a perspective view of an illustrative apparatus in accordance with principles of the invention.

FIG. 31A shows illustrative implant 3130. Implant 3130 may include longitudinal axis LI, distal hub 110 and proximal hub 110. Implant 3130 may be configured to expand into a spherical profile or "lollipop" shape. An anchor, such as anchor 126 (shown in FIG. 1) may easily engage implant 3130 without being deflected away.

Figure 31B:
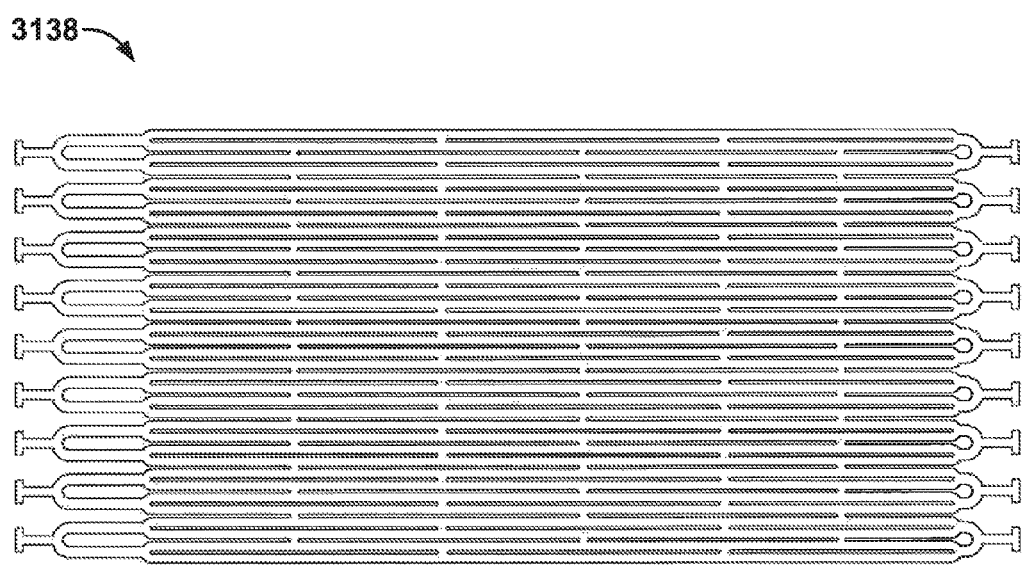
FIG. 31B shows information that may be used to manufacture apparatus in accordance with principles of the invention.

FIG. 31B shows illustrative cut pattern 3138. Cut pattern 3130 may be configured to expand into a "lollipop" shape (shown in FIG. 31A).

Figure 31C:
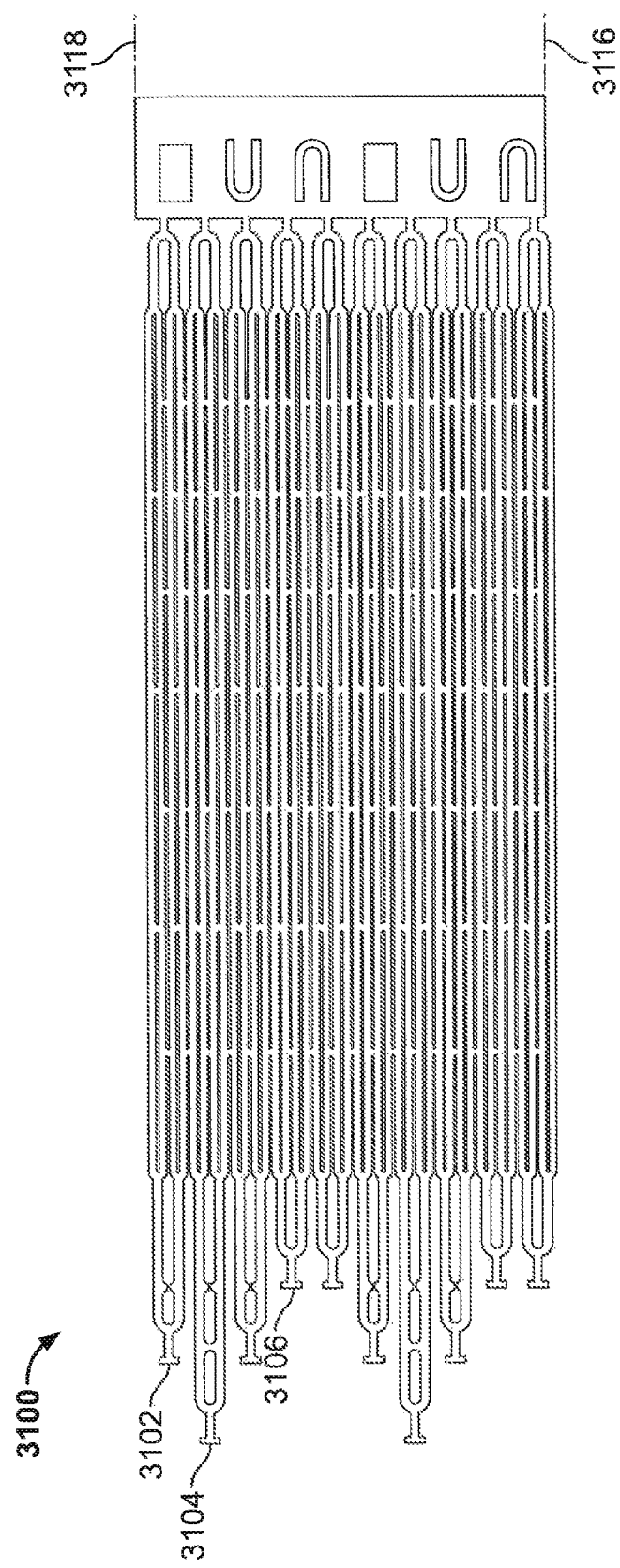
FIG. 31C shows information that may be used to manufacture apparatus in accordance with principles of the invention.

FIG. 31C shows illustrative cut pattern 3100. Cut pattern 3100 may be "rolled" about a longitudinal axis (not shown)

such that edge 3118 is configured to be adjacent to edge 3116. In a "rolled" configuration, cut pattern 3100 may be expandable from the longitudinal axis. To achieve a "rolled" configuration cut pattern 3100 may be cut in a cylindrical tube.

Cut pattern 3100 may include longitudinal cell density 3102. Cut pattern 3100 may include longitudinal cell density 3104. Cut pattern 3100 may include longitudinal cell density 3106.

Cell density 3102 may be configured to expand into a first profile and a second profile. Cell density 3104 may be configured to expand into a first profile, a second profile and a third profile. Cell density 3106 may be configured to expand into a first profile. A first profile may include a substantially conical shape. A third profile may be substantially planar and substantially normal to the longitudinal axis (not shown). A second profile may be configured to bridge between the first profile and the third profile.

Cut pattern 3100 may be configured to be expandable about the longitudinal axis (not shown) into profiles that may include rectangle, rhombic, triangular, oval, round, and/or non-symmetric shapes. Cut pattern 3100 may be expandable about the longitudinal axis (not shown) into profiles that have a cross section that may include rectangle, rhombic, triangular, oval, round, and/or non-symmetric cross shapes.

Figure 32:
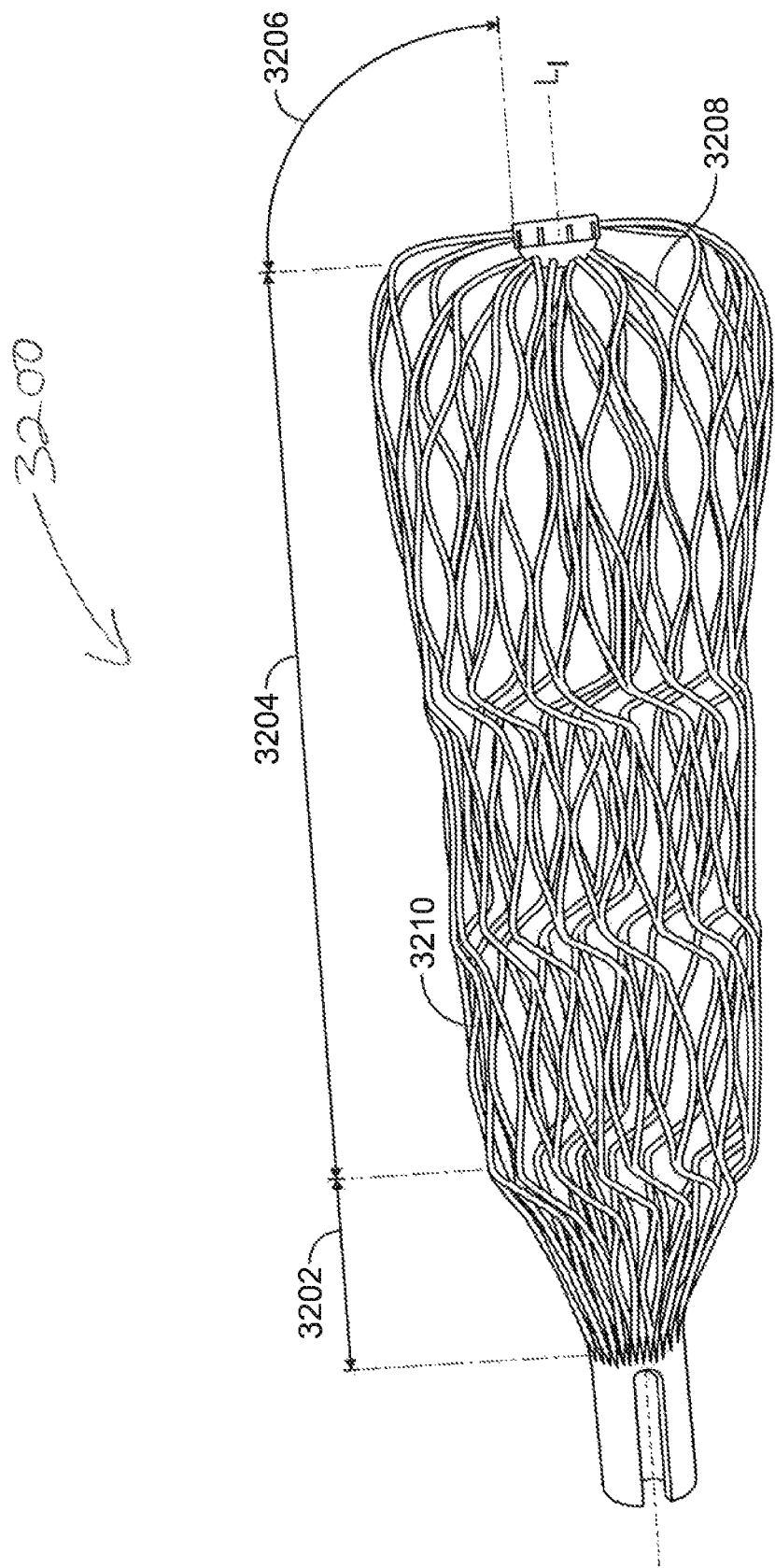
FIG. 32 shows a side view of an illustrative apparatus in accordance with principles of the invention.

FIG. 32 shows illustrative implant 3200. Implant 3200 may include longitudinal axis LI. Implant 3200 may include expandable web 3210 expandable about axis LI. Implant 3200 may include expandable web 3208 expandable about axis LI. Expandable web 3210 may be external to expandable web 3208.

Expandable web 3210 may be configured to expand into profile 3202 about axis LI. Profile 3202 may be substantially conical. Expandable web 3210 may be configured to expand into profile 3206 about axis LI. Profile 3206 may be substantially planar and substantially normal to longitudinal axis LI. Profile 3204 may be configured to expand about axis LI and bridge between profile 3202 and profile 3206.

Figure 33:
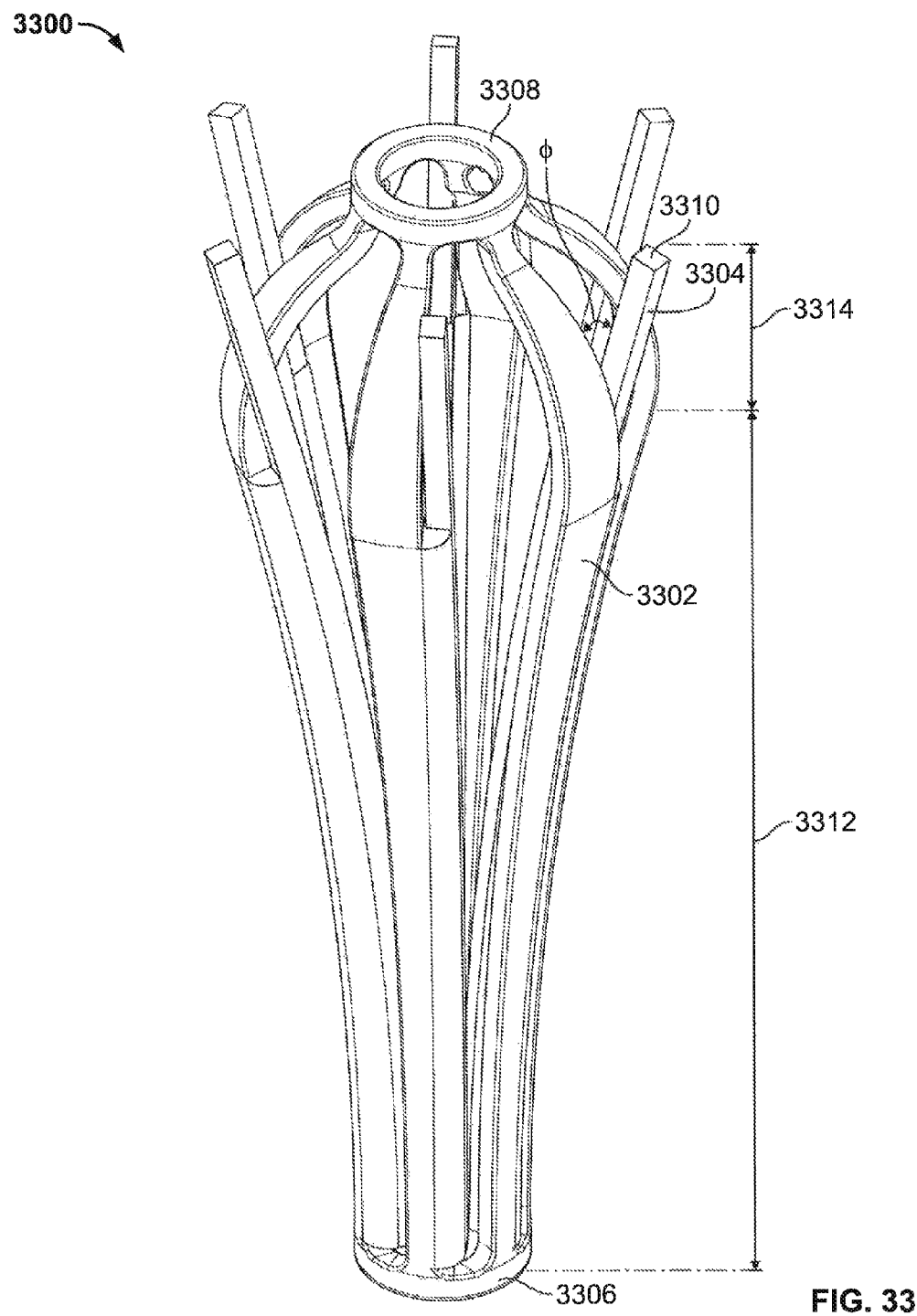
FIG. 33 shows a perspective view of an illustrative apparatus in accordance with principles of the invention.

FIG. 33 shows illustrative implant 3300. Implant 3300 may include supporting member 3302. Supporting member 3302 may extend from proximal end 3306 of implant 3300 to distal end 3308 of implant 3300. Implant 3300 may include bone engaging member 3304. Bone engaging member 3304 may extend from proximal end 3306 of implant 3300 alongside support member 3302 for length 3312. Bone engaging member 3304 may diverge from support member 3302 for length 3314. Bone engaging member 3304 may diverge from support member 3302 at angle φ.

Tip 3310 may be configured to engage cancellous bone BCA of bone B (shown in FIG. 2). Bone engaging member 3304 may be configured to resist translational movement between implant 3300 and bone B. Bone engaging member 3304 may be configured to resist rotational movement between implant 3300 and bone B.

Figure 34:
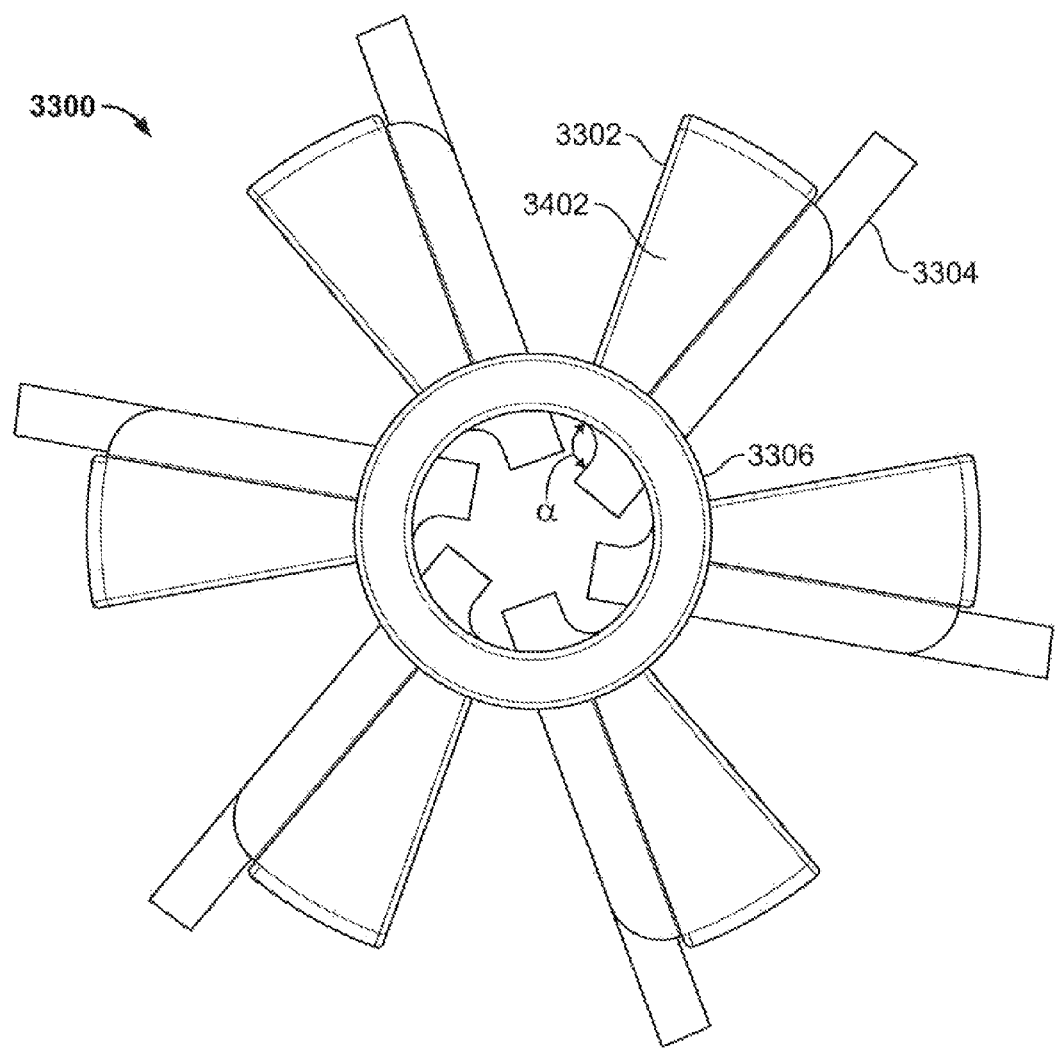
FIG. 34 shows an end view of the apparatus shown in FIG. 33.

FIG. 34 shows a view of implant 3300 from proximal end 3306. Bone engaging member 3304 may be configured to extend alongside support member 3302 in a direction substantially perpendicular to a surface 3402 of support member 3302. Bone engaging member 3304 may be configured to provide axial support to implant 3300 along a longitudinal axis (not shown) of implant 3300. Bone engaging member 3304 may be configured to provide radial support to implant 3300 about a longitudinal axis (not shown) of implant 3300.

Angle α formed between bone engaging member 3304 and support member 3302 may be substantially 90 degrees. Bone engaging member 3304 and support member 3302 may form a "L", "U" or any other suitable shape.

Figure 35:
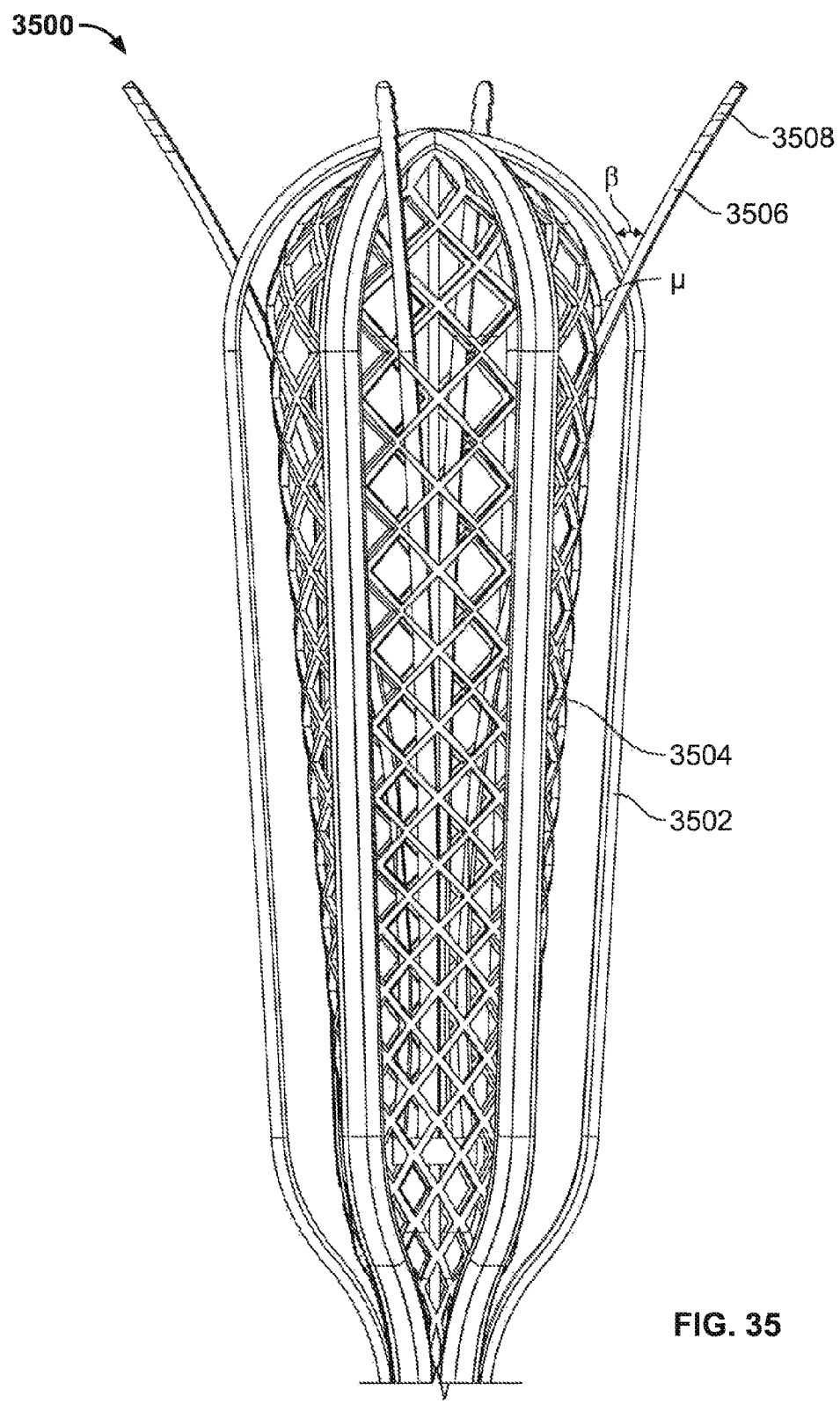
FIG. 35 shows a perspective view of an illustrative apparatus in accordance with principles of the invention.

FIG. 35 shows illustrative implant 3500. Implant 3500 may include web 3504. Implant 3500 may include support structure 3502. Implant 3500 may include bone engaging member 3506. Bone engaging member 3506 may pass through web 3504. Bone engaging member 3506 may pass through web 3504 at angle μ between web 3504 and bone engaging member 3506.

Bone engaging member 3506 may pass through support structure 3502. Bone engaging member 3506 may pass through support structure 3502 at angle β between support structure 3502 and bone engaging member 3506.

Bone engaging member 3502 may be independent of implant 3500. Bone engaging member 3506 may be configured to be inserted into access hole H (showing in FIG. 1) after implant 3500.

Tip 3508 may engage cancellous bone BCA of bone B (shown in FIG. 2). Bone engaging member 3506 may be configured to resist translational movement between implant 3500 and bone B. Bone engaging member 3506 may be configured to resist rotational movement between implant 3500 and bone B.

Figure 36:
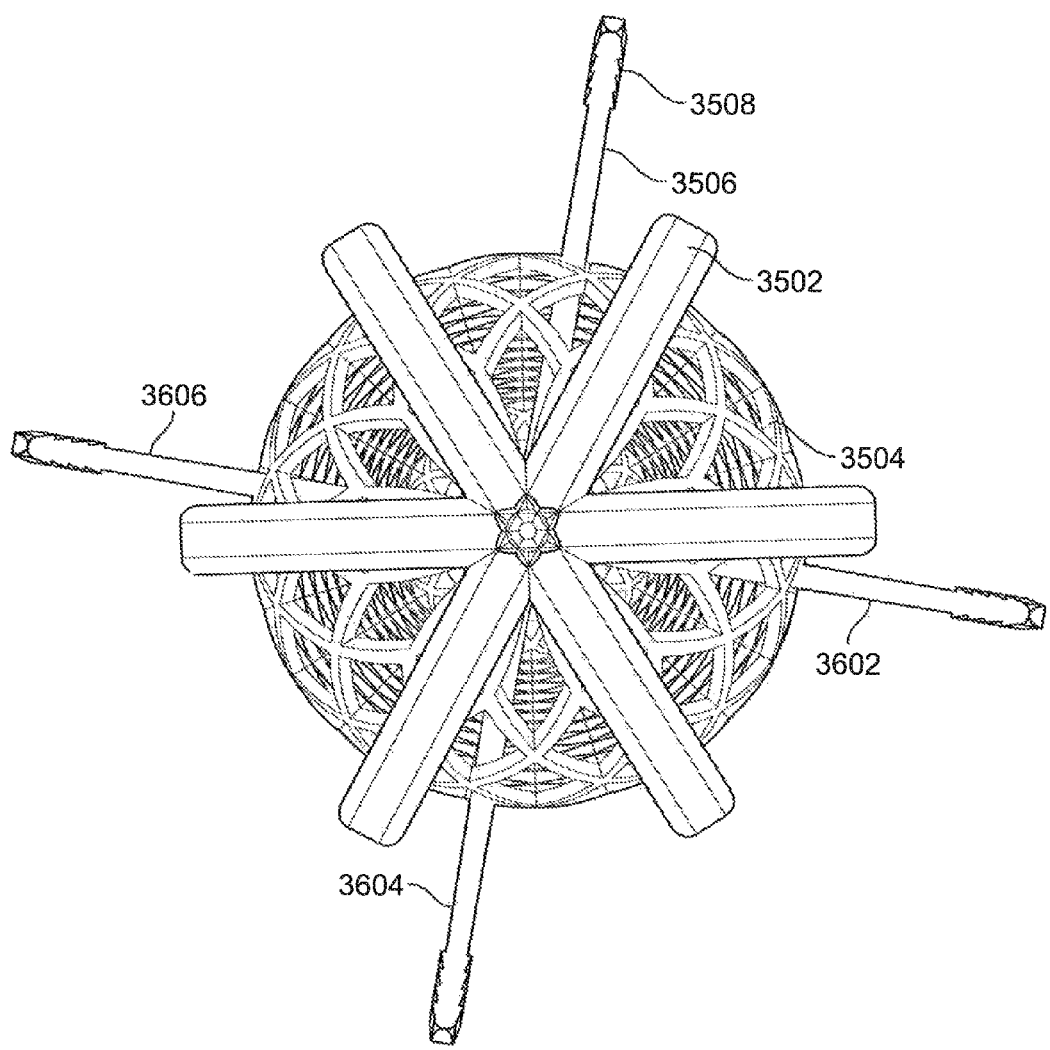
FIG. 36 shows an end view of the apparatus shown in FIG. 35.
Figure 37:
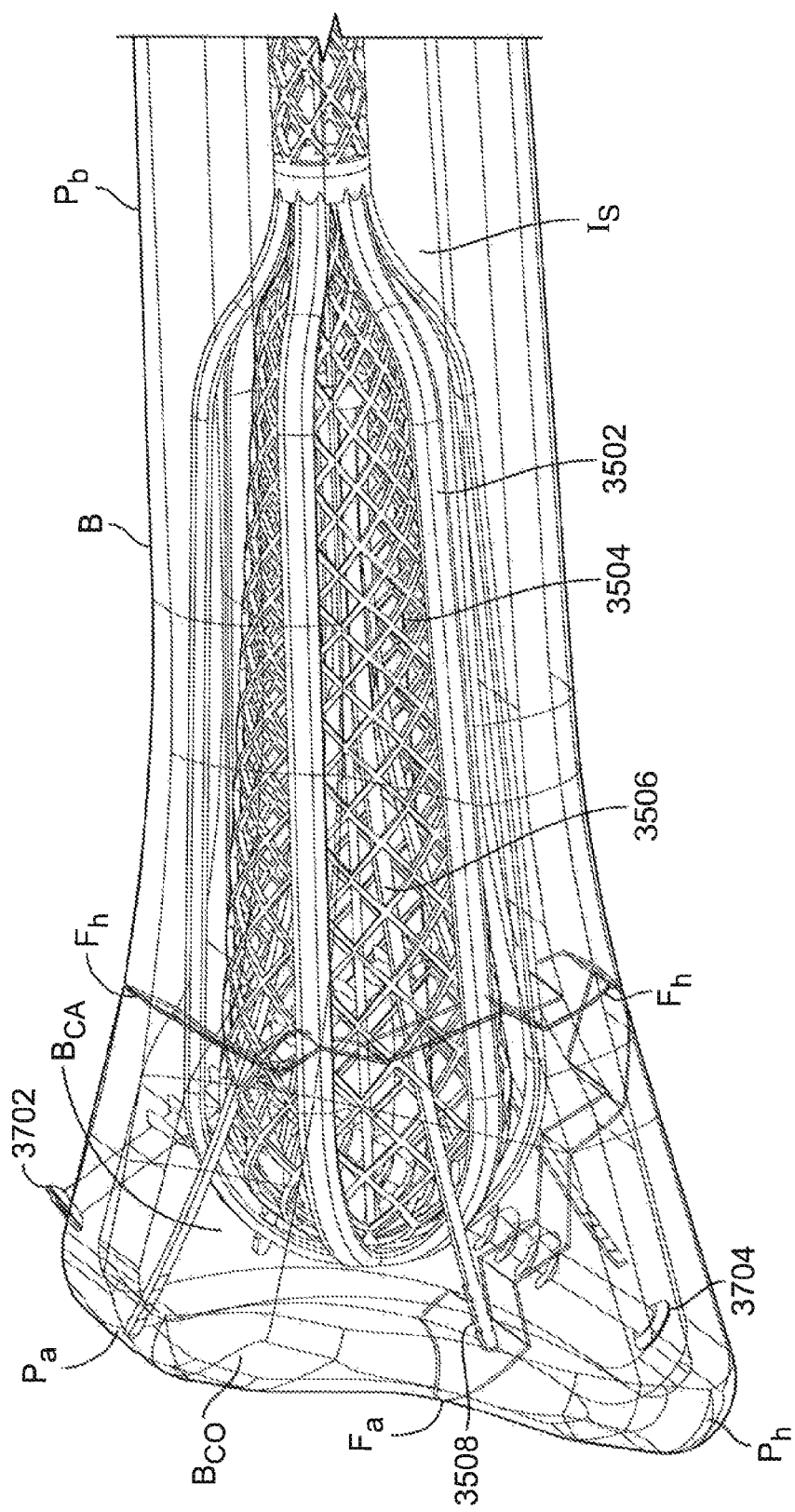
FIG. 37 shows a perspective view of the apparatus shown in FIG. 35 along with illustrative anatomy.

FIG. 36 shows a distal view of illustrative implant 3500. One or more bone engaging member 3505 may be configured to engage cancellous bone BCA. One or more bone engaging members 3506 may FIG. 37 shows illustrative expandable implant 3700 inside bone B (shown in FIG. 2). Bone B is shown with fractures Fh and Fa. Implant 3700 may be configured to repair factures Fh and Fa. Anchors 3702 and 3704 may be configured to fix bone portions Pa and Ph to implant 3700.

Bone engaging member 3506 may be configured to resist translational motion between implant 3700 and bone B. Bone engaging member 3506 may be configured to resist rotational motion between implant 3700 and bone B. Bone engaging member 3606 may engage cancellous bone BCA. Bone engaging member 3506 may engage cortical bone BCO.

Figure 38:
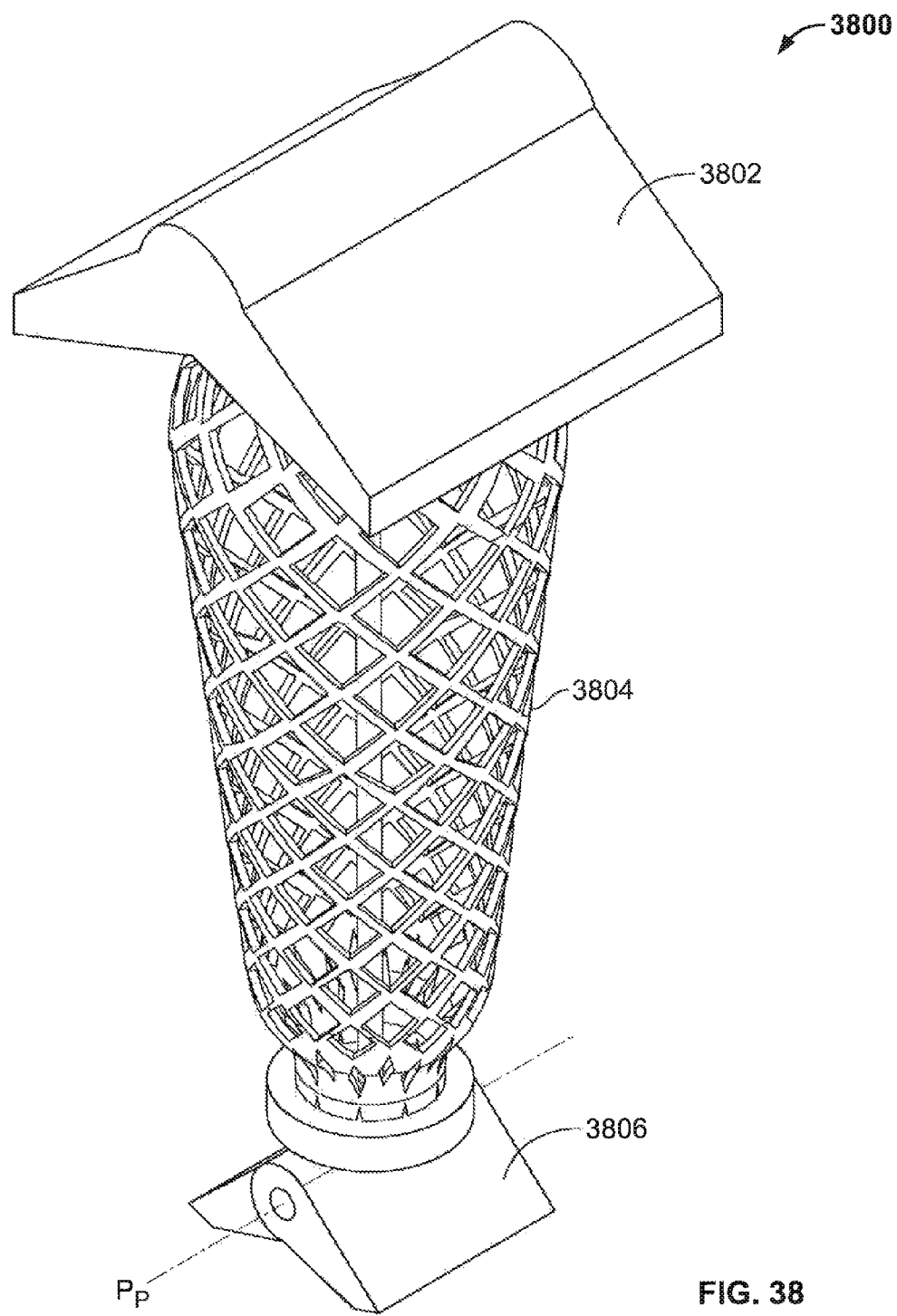
FIG. 38 shows a perspective view of an illustrative apparatus in accordance with principles of the invention.

FIG. 38 shows illustrative implant 3800. Implant 3800 may include expandable web 3804. Implant 3800 may include scissor type locking mechanism 3802. Locking mechanism 3802 may be located at a distal end of implant 3800. Locking mechanism 3802 may be configured to expand. Locking mechanism 3802 may be configured to collapse. Locking mechanism 3802 may be configured to expand and/or collapse by rotating about pivot axis PD.

Scissor type locking mechanism 3802 may be configured to engage bone B. Scissor type locking mechanism 3802 may be configured to fix implant 3800 to bone B. Locking mechanism 3802 may be configured to resist rotational motion between implant 3800 and bone B. Locking mechanism 3802 may be configured to resist translational motion between implant 3800 and bone B.

Implant 3800 may include scissor type locking mechanism 3806. Locking mechanism 3806 may be located at a proximal end of implant 3800. Locking mechanism 3806 may include pivot axis PP. Locking mechanism may expand and/or collapse about axis PP. Locking mechanism 3806 may include one or more of the features of locking mechanism 3802.

Figure 39:
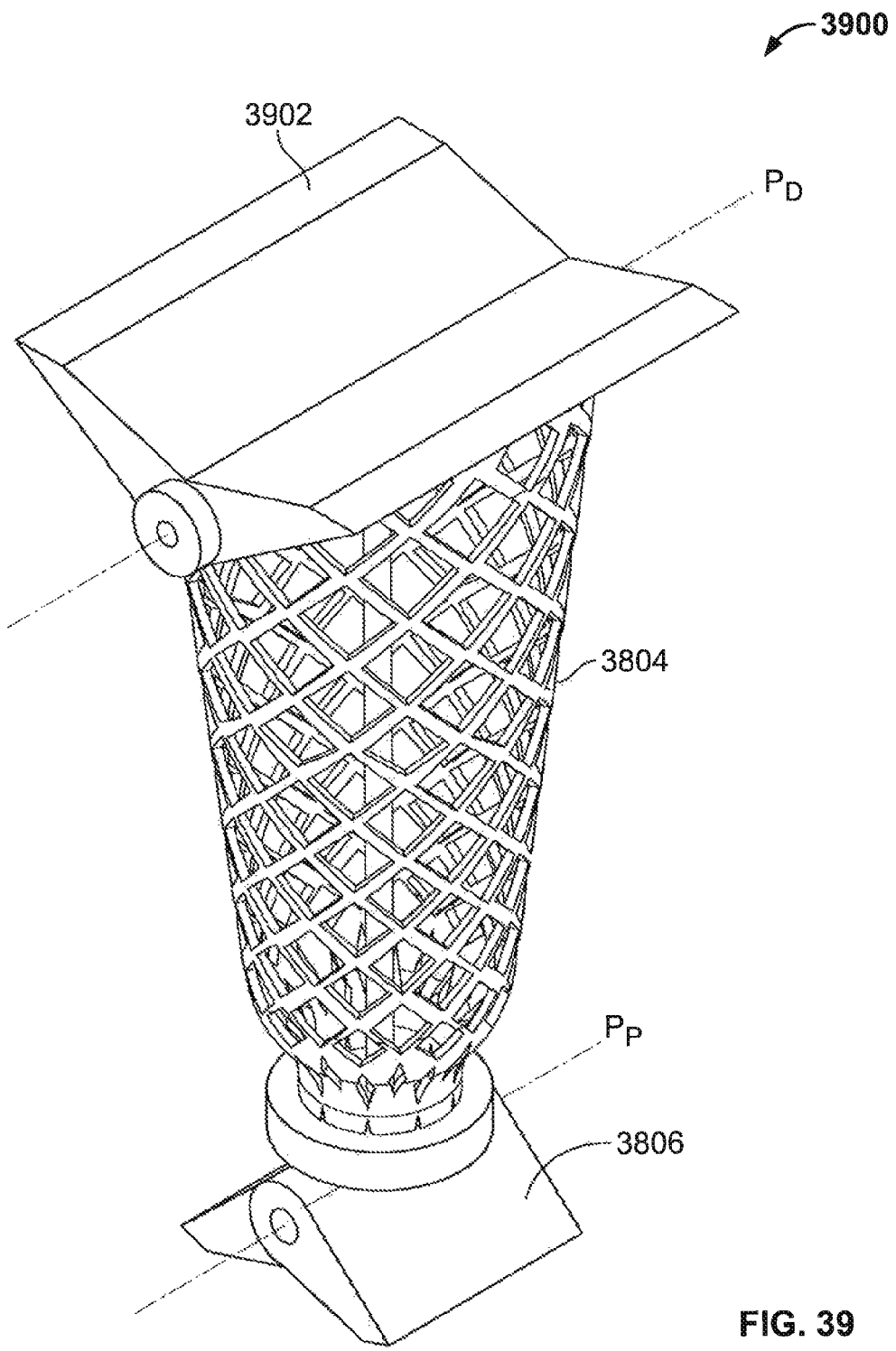
FIG. 39 shows a perspective view of an illustrative apparatus in accordance with principles of the invention.

FIG. 39 shows illustrative implant 3900. Implant 3900 may include expandable web 3804. Implant 3900 may include scissor type locking mechanism 3806. Implant 3900 may include scissor type locking mechanism 3902.

Scissor type locking mechanism 3902 may be configured to fix implant 3900 to bone B (shown in FIG. 2). Locking mechanism 3902 may be configured to pivot about pivot axis PD. Expansion of locking mechanism 3902 against bone B may fix implant 3900 relative to bone B. Locking mechanism 3902 may be configured to resist rotational motion between implant 3900 and bone B. Locking mechanism 3902 may be configured to resist translational motion between implant 3900 and bone B.

FIG. 40 shows illustrative web 4000. Web 4000 may be representative of webs that may be used in connection with implants shown and described herein. For example, a web such as web 4000 may be included in implant 100 (shown in FIG. 1), implant 300 (shown in FIG. 3), implant 1312 (shown in FIG. 13), implant 2100 (shown in FIG. 21), implant 2320 (shown in FIG. 23b), implant 2900 (shown in FIG. 29), implant 3000 (shown in FIG. 30), implant 3130 (shown in FIG. 31a), implant 3200 (shown in FIG. 32), implant 3500 (shown in FIG. 25), implant 3804 (shown in FIG. 38) and any other suitable implants.

Web 4000 may include one or more cells such as cell 4002. Web 4000 may include a front 4010 and a back 4012. Cell 4002 is configured to receive anchor 4004. Anchor 4004 may have one or more features in common with anchors such as anchor 114, 116, and 126 (shown in FIG. 1), 1204 (shown in FIG. 12), 1314 (shown in FIG. 13) and any other suitable anchors. Anchor 4004 may be configured to secure a fragment of bone B to web 4000.

Cell 4002 may have an opening that is large enough to allow passage of anchor root 4006 through cell 4002 without deformation of cell 4002 when anchor 4004 is oriented normal to cell 4002. Such a cell may be referred to as an "open cell." If anchor 4004 were to penetrate cell 4002 at an oblique angle, such that less than the full opening of cell 4002 were present in a plane normal to anchor 4004, cell 4002 may deform to accommodate root 4006.

Cell 4002 may be open by virtue of expansion from a closed state. Cell 4002 may be fabricated in an open state. Cell 4002 may be implanted in bone B (shown in FIG. 2) in an open state. Cell 4002 may be implanted in bone B (shown in FIG. 2) in a closed state. Cell 4002 may be expanded after deployment in bone B.

Anchor 4004 may include engagement feature 4008. Engagement feature 4008 may be configured to engage the back 4012 of cell 4002 and apply tension between cell 4002 and a bone fragment of bone B. Anchor 4004 may be configured to prevent disengagement of engagement feature 4004 from back 4012 of cell 4002 when tension is applied. Cell 4002 may be configured to eb elastically deformed when tension is applied.

Figure 41:
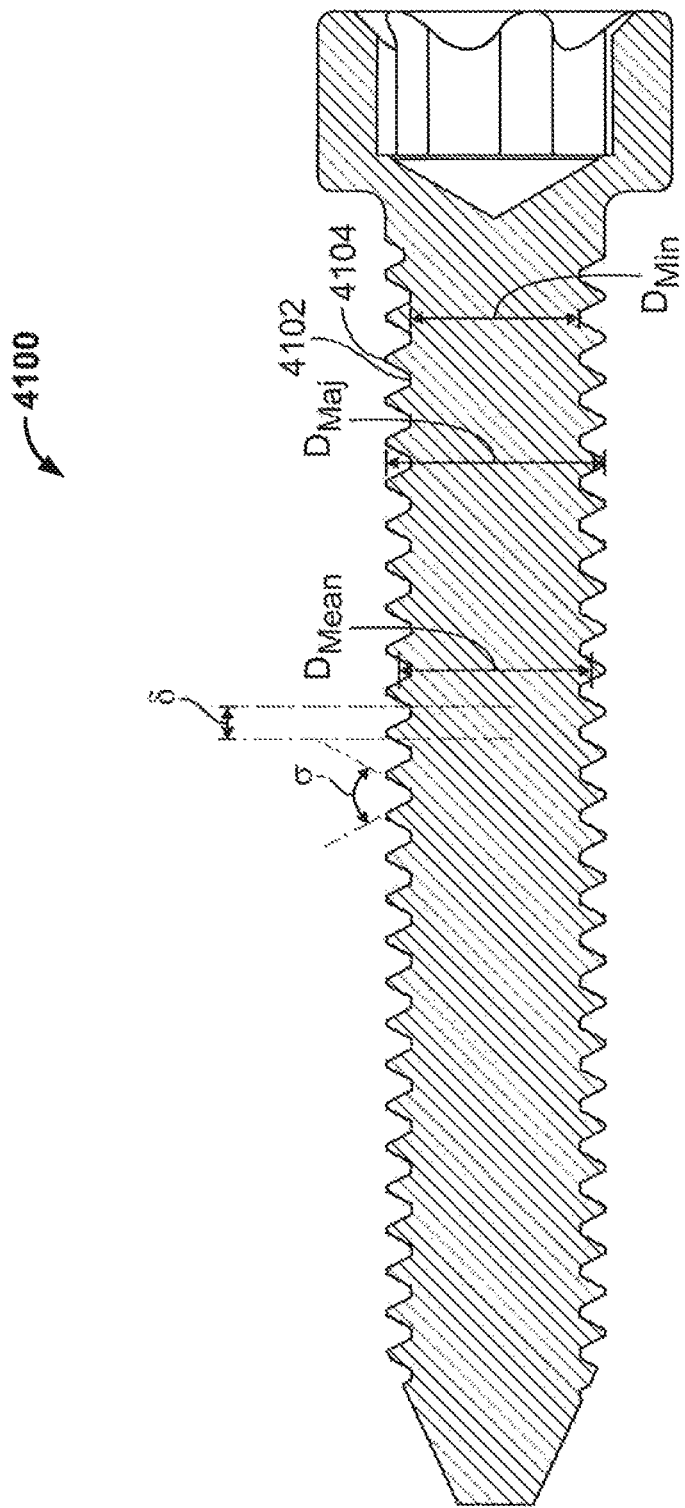
FIG. 41 shows a cross section of a portion of the apparatus shown in FIG. 40.

FIG. 41 shows illustrative threaded anchor 4100. Threaded anchor 4100 may be configured to apply tension between a fragment of bone B and web 4000. Threaded anchor 4100 may be configured to engage cell 4002 based on a metric of threaded anchor 4100. Threaded anchor 4100 may include root 4102. Threaded anchor 4100 may include crest 4104.

A metric of threaded anchor 4100 may include major diameter Dmaj, minor diameter Dmin, mean diameter Dmean, thread angle σ, thread pitch δ. A metric of threaded anchor 4100 may be selected based on a limitation on how much tension may be applied to a cell such as cell 4002.

Figure 42:
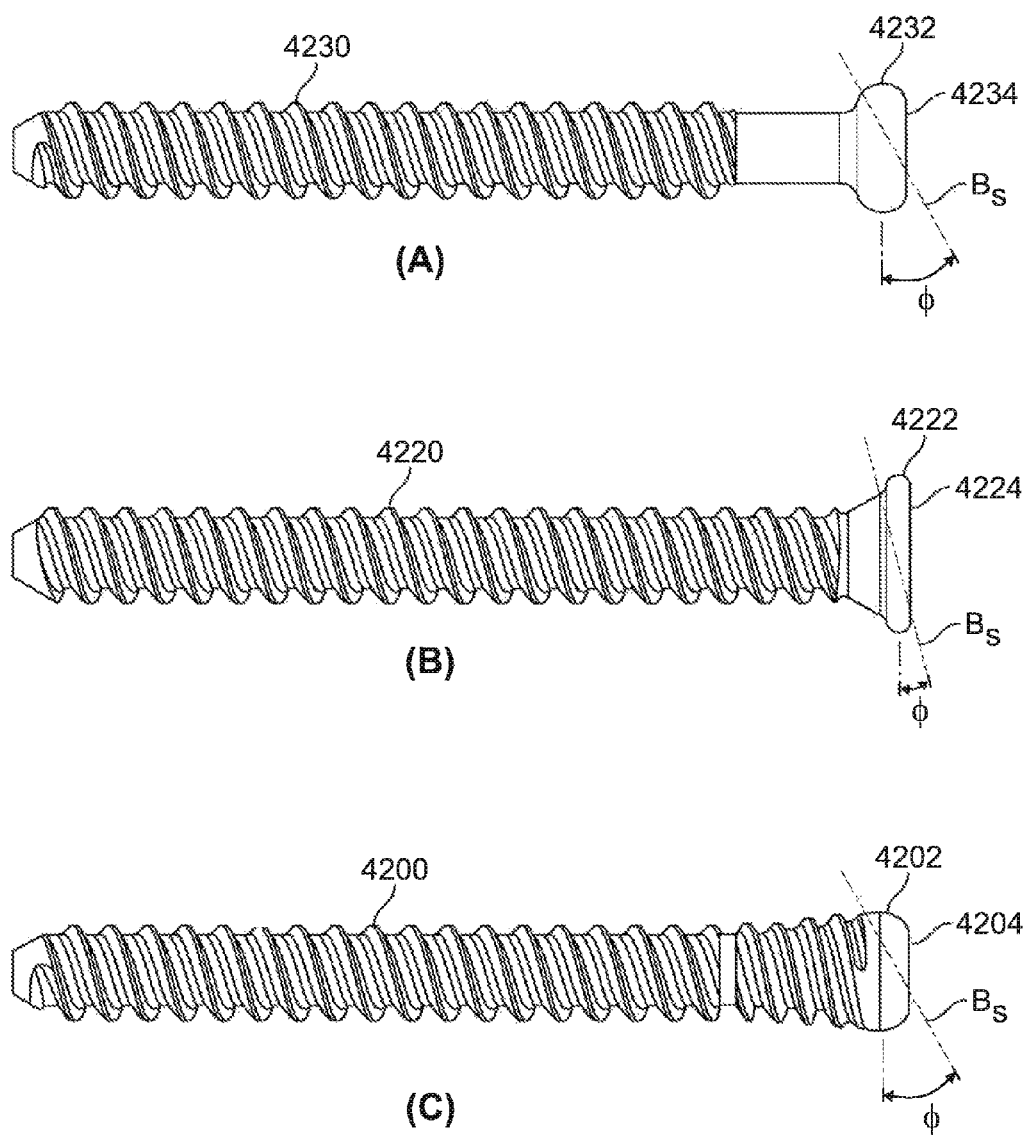
FIGS. 42(A)-(C) show a side view of illustrative apparatus in accordance with principles of the invention.

FIGS. 42(A)-(C) show illustrative threaded anchors 4230, 4220 and 4200. Anchors 4230, 4220 and 4200 may include one or more of the metrics of threaded anchor 4100. Anchor 4230 includes head portion 4234. Head portion 4234 may include axis 4232. Anchor 4220 includes head portion 4224. Head portion 4224 may include axis 4222. Anchor 4200 includes head portion 4204. Head portion 4204 may include axis 4202.

Head portions 4234, 4224 and 4202 may be configured to form an angle Φ with bone surface BS (shown in FIG. 2). Based on angle Φ, an anchor most atraumatic to bone B may be selected.

Figures 43, 44:
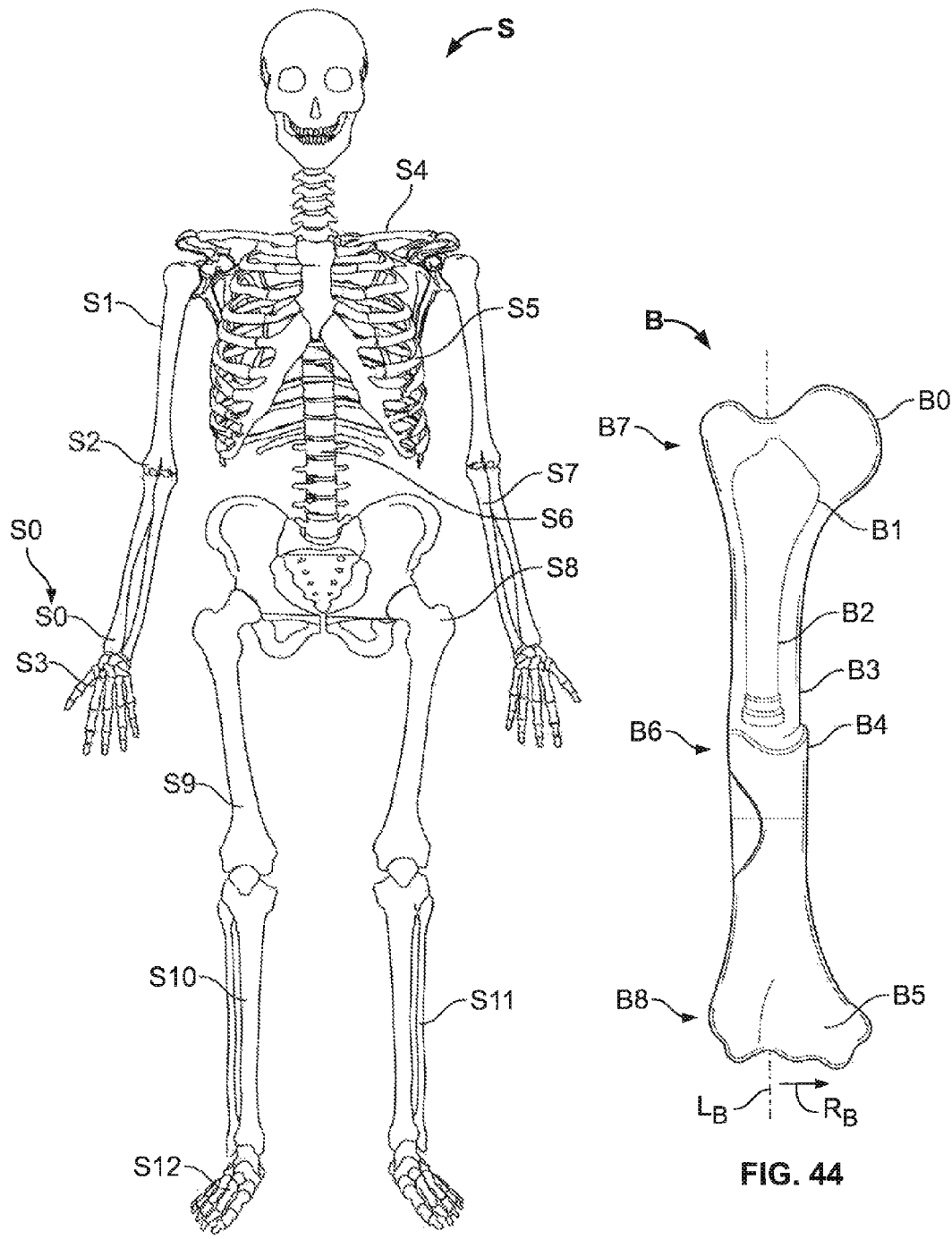
FIG. 43 shows a front view of an illustrative human Skeleton.
FIG. 44 shows a partial sectional view of a fractured bone.

FIG. 43 shows illustrative skeleton S. Skeleton S includes illustrative bones Si in which illustrative implants described herein may be used as shown and described in connection with bone B (shown in FIG. 2). Table 2 includes a partial list of bones Si.

TABLE 2

Bones $S_i$.

| Bone | Reference numeral in FIG. 2 |
|---|---|
| Distal Radius | $S_0$ |
| Humerus | $S_1$ |
| Proximal Radius and Ulna (Elbow) | $S_2$ |
| Metacarpals | $S_3$ |
| Clavicle | $S_4$ |
| Ribs | $S_5$ |
| Vertebrae | $S_6$ |
| Ulna | $S_7$ |
| Hip | $S_8$ |
| Femur | $S_9$ |
| Tibia | $S_{10}$ |
| Fibula | $S_{11}$ |
| Metatarsals | $S_{12}$ |

FIG. 44 schematically shows anatomy of bone B (shown in FIG. 2). Anatomical features of bone B are listed in Table 2. Apparatus and methods in accordance with the principles of the invention may involve one or more of the anatomical features shown in Table 3. Features of bone B may be described in reference to bone axis LB (in which B indicates bone) and radius RB (in which B indicates bone).

TABLE 3

Anatomical features of some of the bone types that may be treated by the apparatus and methods.

| Anatomical feature | Reference numeral in FIG. 44 |
|---|---|
| Articular surface | $B_0$ |
| Cancellous, spongy or trabecular bone | $B_1$ |
| Medullary cavity | $B_2$ |
| Cortical or dense bone | $B_3$ |
| Periosteum | $B_4$ |
| Proximal articular surface | $B_5$ |
| Diaphysis or midshaft | $B_6$ |
| Metaphysis or end region | $B_7$ |
| Epiphysis | $B_8$ |
| Articular surface | $B_9$ |

The terms "end-bone" and "end-bone fracture" may be used to refer to fractures that occur in the epiphyseal or metaphyseal region of long bones. Such fractures include peri-articular and intra-articular fractures.

Figure 45:
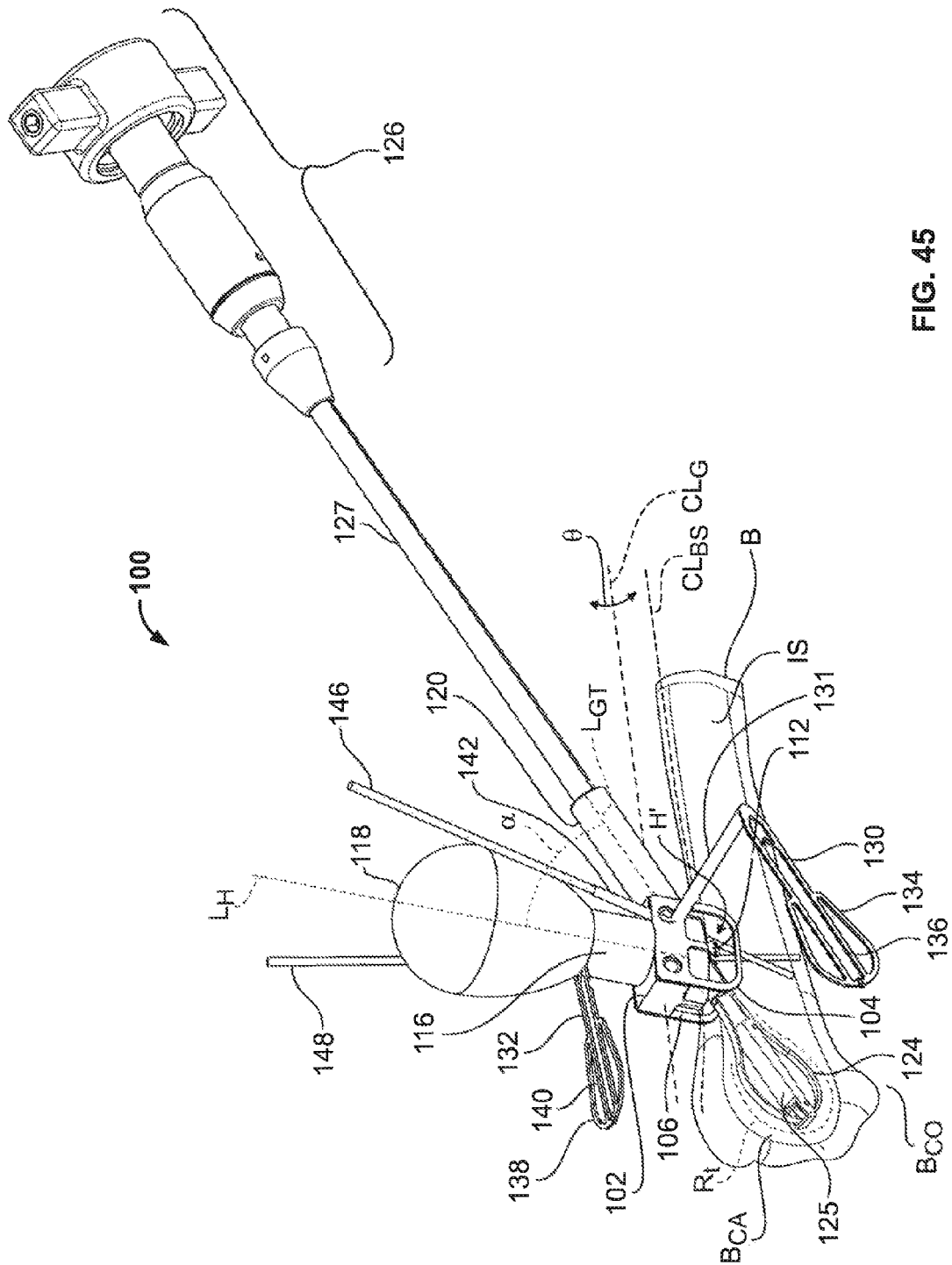
FIG. 45 shows a perspective view of an illustrative apparatus for preparing illustrative anatomy for an apparatus in accordance with principles of the invention.

FIG. 45 shows illustrative instrument guide 4500 for positioned at site H' on bone B. Illustrative instrument guide 4500 may be configured to prepare bone B for delivery of illustrative implants described herein. Broach head 4524 may be delivered through guide 4500 to target region $R_t$ of intramedullary space IS. Target region $R_t$ is illustrated as being within cancellous bone $B_{CA}$, but could be in either, or both, of cancellous bone $B_{CA}$ and cortical bone $B_{CO}$. Side template 4530 and top template 4532 are registered to guide tube 4520. Arm 4531 may support template 4530. A practitioner may position templates 4530 and 4532 such that templates 4530 and 4532 "project" onto target region $R_t$ so that guide 4500 will guide broach head 4524 to target region $R_t$.

Template 4530 may include lobe outline 4534 and shaft outline 4536 for projecting, respectively, a "swept-out" area of broach head 4524 and a location of shaft-like structure 4525. Template 4532 may include lobe outline 4538 and shaft outline 4540 for projecting, respectively, a target "swept-out" area of broach head 4524 and a target location of shaft-like structure 4525. Templates 4530 and 4532 may be configured to project a shape of any suitable instrument that may be deployed, such as a drill, a coring saw, a prosthetic device or any other suitable instrument.

Fluoroscopic imaging may be used to position templates 4530 and 4532 relative to target region $R_t$.

Broach head 4524 may rotate in intramedullary space IS to clear intramedullary bone matter so that a prosthetic device may be implanted. Broach head 4524 may be driven and supported by broach control 4526 and broach sheath 4527.

Guide 4500 may include base 4502. Alignment members 4504 and 4506 may extend from base 4502 to align guide centerline $CL_G$ of guide 4500 with bone centerline $CL_{BS}$ of the top surface of bone B. One or both of alignment members 4504 and 4506 may be resilient. One or both of alignment members 4504 and 4506 may be stiff.

Alignment members 4504 and 4506 (not shown) may be relatively free to slide along surfaces of bone B. Guide 4500 may include contacts 4508 and 4510 that may engage bone B along centerline $CL_{BS}$. Contacts 4508 and 4510 may extend from a bottom surface (not shown) of guide 4500. Contacts 4508 and 4510 may prevent guide centerline $CL_G$ from rotating out of alignment with bone centerline $CL_{BS}$.

Contacts 4508 and 4510 may assure alignment of guide 4500 with the surface of bone B, because two points of contact may be stable on an uneven surface even in circumstances in which 3, 4 or more contacts are not stable.

Guide 4500 may include lateral cleats 4512 and 4514 (not shown). Lateral cleats 4512 and 4514 may engage the surface of bone B to prevent guide 4500 from rotating in direction θ about guide centerline $CL_G$. Lateral cleats 4512 and 4514 may be resilient to allow some sliding over bone B.

When a practitioner positions guide 4500 on bone B, alignment members 4504 and 4506 may be the first components of guide 4500 to engage bone B. Alignment members 4504 and 4506 may bring guide centerline $CL_G$ into alignment with bone centerline $CL_{BS}$ before contacts 4508 and 4510 and cleats 4512 and 4514 engage bone B. Then, in some embodiments, cleats 4512 and 4514 may engage bone B to inhibit rotation in direction θ. Then, in some embodiments, contacts 4508 and 4510 may engage bone B along bone centerline $CL_{BS}$. Contacts 4508 and 4510 may have sharp points to provide further resistance to de-alignment of guide centerline $CL_G$ from bone centerline $CL_{BS}$. In some embodiments, there may be no more than two contacts (e.g., 4508 and 4510) to ensure that the contacts are in line with bone centerline $CL_{BS}$.

Guide 4500 may include stem 4516 and grip 4518. A practitioner may manually grip 4518. In some embodiments, a torque-limiter (not shown) may be provided to limit the torque that the practitioner can apply via grip 4518 to contacts 4508 and 4510.

Guide tube 4520 may receive and guide any suitable instrument. Guide tube 4520 may be oriented at angle α with respect to handle 4516. In some embodiments, angle α may be fixed. In some embodiments, angle α may be adjustable. In some embodiments, templates 4530 and 4532 may be fixed relative to guide tube 4520. In some embodiments, including some embodiments in which α is adjustable and some in which α is not adjustable, guide tube 4520 may be oriented so that the axis $L_{GH}$ of guide tube 4520 intersects bone B at substantially the same point as does axis $L_H$ of stem 4516. Grip 4518 will thus be positioned directly over the center of hole site H'.

Guide 4500 may include channels 4542 and 4544 (not shown). Rods 4546 and 4548 may be inserted through channels 4542 and 4544, respectively, through cortical bone $B_{CO}$. Rods 4546 and 4548 may stabilize guide 4500 on bone B. Rods 4546 and 4548 may be K-wires. Rods 4546 and 4548 may be inserted using a wire drill.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments of the invention may omit steps shown and described in connection with the illustrative methods. Some embodiments of the invention may include steps that are not shown and described in connection with the illustrative methods.

Although the invention has been described in terms of particular embodiments and applications, one of ordinary skill in the art, in light of this teaching, can generate additional embodiments and modifications without departing from the spirit of or exceeding the scope of the principles of the invention. Accordingly, it is to be understood that the drawings and descriptions herein are proffered by way of example to facilitate comprehension of the invention and should not be construed to limit the scope thereof.

Thus, apparatus and methods for fracture repair have been provided. Persons skilled in the art will appreciate that the present invention can be practiced by other than the described embodiments, which are presented for purposes of illustration rather than of limitation. The present invention is limited only by the claims that follow.

What is claimed is:

1. A lock for a bone implant, the implant comprising:
   a proximal base and a distal base that define a longitudinal axis; and
   a web having a proximal end and a distal end, the proximal end fixed to the proximal base and the distal end fixed to the distal base, the web, after being inserted into a bone, urging radially away from the axis;
   the lock comprising:
     a first threaded cannula that is fixed to the proximal base and substantially coaxial with the axis;
     a second threaded cannula that is fixed to the distal base, substantially coaxial with the axis and disposed apart from the first threaded cannula; and
     a screw that is configured to be advanced into the first threaded cannula after the web reaches an expanded state inside the bone, advanced along the axis to the second threaded cannula and advanced into the second threaded cannula without substantially changing a distance between the first threaded cannula and the second threaded cannula;
   wherein engagement of the screw with the first threaded cannula and the second threaded cannula locks the web in the expanded state.

2. The lock of claim 1 wherein, when the web is a first web, the implant includes second web that is disposed between the longitudinal axis and the first web.

3. The lock of claim 2 wherein, when the distance is fixed, the second web is slidable along the longitudinal axis and rotatable about the longitudinal axis.

4. The lock of claim 3 wherein, when the distance is fixed, the second web is expandable about the longitudinal axis.

5. The lock of claim 2 wherein, when the distance is fixed, the second web is slidable along the longitudinal axis and expandable about the longitudinal axis.

6. The lock of claim 5 wherein, when the distance is fixed, the second web is rotatable about the longitudinal axis.

7. The lock of claim 2 wherein the first web is, relative to the longitudinal axis, at a greater radial distance than is the second web.

8. The lock of claim 1 wherein the screw is configured to apply tension between the first threaded cannula and the second threaded cannula when the web bears a radial load.

9. The lock of claim 8 wherein:
the screw is of unified construction;
and,
of all the structures that are configured to operate in conjunction with the implant, the screw alone is configured to apply the tension.

10. The lock of claim 1 wherein the engagement of the screw with the first threaded cannula and the second threaded cannula fixes the distance.

11. The lock of claim 1 wherein:
the distance comprises:
a maximum value that corresponds to a fully collapsed state of the web; and
a minimum value that corresponds to a fully expanded state of the web;
the screw is configured to longitudinally fix the distance at any value in the range from about the maximum value to about the minimum value;
the fully collapsed state corresponds to a state in which the implant is configured to pass through an access hole in the bone; and
the fully expanded state corresponds to a state in which the implant is expanded outside the bone at standard temperature and pressure.

12. The lock of claim 1 wherein the engagement of the screw is configured to lock the web in the expanded state such that when the web bears a radial load the web deforms and the distance does not change.

13. The lock of claim 1 wherein the distance corresponds to a radial distance of the web from the longitudinal axis.

14. The lock of claim 1 wherein:
the screw is of unified construction;
of all the structures that are configured to operate in conjunction with the implant, the screw alone is configured to fix the distance.

15. The lock of claim 1 wherein the distance corresponds to the expanded state, the expanded state configured to provide structural support for the bone and substantially eliminating residual outward radial pressure on an inside wall of the bone.

16. The lock of claim 1 wherein the screw comprises a thread that is sufficiently fine to avoid substantially changing the distance when the screw engages the second threaded cannula.

17. The lock of claim 1 wherein, when the second threaded cannula has an outer diameter, the first threaded cannula includes:
a threaded portion that is configured to engage the screw; and
an unthreaded portion that has an inner diameter that is greater than the outer diameter of the second threaded cannula, the unthreaded portion being configured to receive a portion of the second threaded cannula.

18. The lock of claim 1 wherein:
a tab extends from one or both of the proximal base and the web;
a pocket is present in one or both of the proximal base and the web;
the tab is biased such that it engages the pocket; and
the web is substantially longitudinally and rotationally fixed to the proximal base by the engagement of the tab and the pocket.

19. A lock for a bone implant, the implant comprising:
a proximal base and a distal base that define a longitudinal axis; and
a web having a proximal end and a distal end, the proximal end fixed to the proximal base and the distal end fixed to the distal base, the web, after being inserted into a bone, urging radially away from the axis;
the lock comprising:
a first threaded cannula that is fixed to the proximal base and is substantially coaxial with the axis;
a second threaded cannula that is fixed to the distal base, is spaced apart from the first threaded cannula and is substantially coaxial with the axis; and
a screw that is configured to:
engage the first threaded cannula after the web expands inside the bone and the first and second threaded cannulas have moved toward each other until they are separated by a distance;
traverse the distance; and,
then, lock the web in an expanded state by engaging the second threaded cannula without substantially moving the second threaded cannula relative to the first threaded cannula.

20. The lock of claim 19 wherein, when the web is a first web, the implant includes a second web that is disposed between the longitudinal axis and the first web.

21. The lock of claim 20 wherein, when the distance is fixed, the second web is slidable along the longitudinal axis and rotatable about the longitudinal axis.

22. The lock of claim 21 wherein, when the distance is fixed, the second web is expandable about the longitudinal axis.

23. The lock of claim 20 wherein, when the distance is fixed, the second web is slidable along the longitudinal axis and expandable about the longitudinal axis.

24. The lock of claim 23 wherein, when the distance is fixed, the second web is rotatable about the longitudinal axis.

25. The lock of claim 20 wherein the first web is, relative to the longitudinal axis, at a greater radial distance than is the second web.

26. The lock of claim 19 wherein the screw is configured to apply tension between the first threaded cannula and the second threaded cannula when the web bears a radial load.

27. The lock of claim 26 wherein:
the screw is of unified construction;
and,
of all the structures that are configured to operate in conjunction with the implant, the screw alone is configured to apply the tension.

28. The lock of claim 19 wherein the engagement of the screw with the first threaded cannula and the second threaded cannula fixes the distance.

29. The lock of claim 19 wherein:
the distance comprises:
a maximum value that corresponds to a fully collapsed state of the web; and
a minimum value that corresponds to a fully expanded state of the web;
the screw is configured to longitudinally fix the distance at any value in the range from about the maximum value to about the minimum value;
the fully collapsed state corresponds to a state in which the implant is configured to pass through an access hole in the bone; and the fully expanded state corresponds to a state in which the implant is expanded outside the bone at standard temperature and pressure.

30. The lock of claim 19 wherein the engagement of the screw with the first threaded cannula and the second threaded cannula is configured to lock the web such that, when the web bears a radial load the web deforms and the distance does not change.

31. The lock of claim 19 wherein the distance corresponds to a radial distance of the web from the longitudinal axis.

32. The lock of claim 19 wherein:
the screw is of unified construction;
of all the structures that are configured to operate in conjunction with the implant, the screw alone is configured to fix the distance.

33. The lock of claim 19 wherein the distance corresponds to the expanded state, the expanded state providing structural support for the bone and substantially eliminating residual outward radial pressure on an inside wall of the bone.

34. The lock of claim 19 wherein the screw comprises a thread that is sufficiently fine to avoid substantially changing the distance when the screw engages the second threaded cannula.

35. The lock of claim 19 wherein, when the second threaded cannula has an outer diameter, the first threaded cannula includes:
a threaded portion that is configured to engage the screw; and
an unthreaded portion that has an inner diameter that is greater than the outer diameter of the second threaded cannula, the unthreaded portion being configured to receive a portion of the second threaded cannula.

36. The lock of claim 19 wherein:
a tab extends from one or both of the proximal base and the web;
a pocket is present in one or both of the proximal base and the web;
the tab is biased such that it engages the pocket; and
the web is substantially longitudinally and rotationally fixed to the proximal base by the engagement of the tab and the pocket.

37. A bone implant comprising:
a proximal base and a distal base that define a longitudinal axis; and
a web having a proximal end and a distal end, the proximal end fixed to the proximal base and the distal end fixed to the distal base, the web, after being inserted into a bone, urging radially away from the axis;
a first threaded cannula that is fixed to the proximal base and is substantially coaxial with the axis;
a second threaded cannula that is fixed to the distal base, substantially coaxial with the axis and spaced apart from the first threaded cannula;
wherein the first and second threaded cannulas are configured such that a screw, advanced along the axis after the web reaches an expanded state, engages the first threaded cannula, then advances from the first threaded cannula to the second threaded cannula and then engages the second threaded cannula without substantially changing a distance between the first threaded cannula and the second threaded cannula;
wherein engagement of the screw with the first threaded cannula and the second threaded cannula locks the web in the expanded state.

38. The bone implant of claim 37 wherein, when the web is a first web, the bone implant includes a second web that is disposed between the longitudinal axis and the first web.

39. The bone implant of claim 38 wherein, when the distance is fixed, the second web is slidable along the longitudinal axis and rotatable about the longitudinal axis.

40. The bone implant of claim 39 wherein, when the distance is fixed, the second web is expandable about the longitudinal axis.

41. The lock of claim 38 wherein, when the distance is fixed, the second web is slidable along the longitudinal axis and expandable about the longitudinal axis.

42. The lock of claim 41 wherein, when the distance is fixed, the second web is rotatable about the longitudinal axis.

43. The bone implant of claim 38 wherein the first web is, relative to the longitudinal axis, at a greater radial distance than is the second web.

44. The bone implant of claim 37 wherein the screw is configured to apply tension between the first threaded cannula and the second threaded cannula when the web bears a radial load.

45. The bone implant of claim 44 wherein:
the screw is of unified construction;
and,
of all the structures that are configured to operate in conjunction with the implant, the screw alone is configured to apply the tension.

46. The bone implant of claim 37 wherein the engagement of the screw with the first threaded cannula and the second threaded cannula fixes the distance.

47. The bone implant of claim 37 wherein:
the distance comprises:
a maximum value that corresponds to a fully collapsed state of the web; and
a minimum value that corresponds to a fully expanded state of the web;
the screw is configured to longitudinally fix the distance at any value in the range from about the maximum value to about the minimum value;
the fully collapsed state corresponds to a state in which the bone implant is configured to pass through an access hole in the bone; and
the fully expanded state corresponds to a state in which the bone implant is expanded outside the bone at standard temperature and pressure.

48. The bone implant of claim 37 wherein the engagement of the screw with the first threaded cannula and the second threaded cannula is configured to lock the web such that, when the web bears a radial load the web deforms and the distance does not change.

49. The bone implant of claim 37 wherein the distance corresponds to a radial distance of the web from the longitudinal axis.

50. The bone implant of claim 37 wherein:
the screw is of unified construction;
of all the structures that are configured to operate in conjunction with the implant, the screw alone is configured to fix the distance.

51. The bone implant of claim 37 wherein the distance corresponds to the expanded state, the expanded state providing structural support for the bone and substantially eliminating residual outward radial pressure on an inside wall of the bone.

52. The bone implant of claim 37 wherein the screw comprises a thread that is sufficiently fine to avoid substantially changing the distance when the screw engages the second threaded cannula.

53. The lock of claim 37 wherein, when the second threaded cannula has an outer diameter, the first threaded cannula includes:

a threaded portion that is configured to engage the screw; and an unthreaded portion that has an inner diameter that is greater than the outer diameter of the second threaded cannula, the unthreaded portion being configured to receive a portion of the second threaded cannula.

54. The bone implant of claim 37 wherein:

a tab extends from one or both of the proximal base and the web;

a pocket is present in one or both of the proximal base and the web;

the tab is biased such that it engages the pocket; and the web is substantially longitudinally and rotationally fixed to the proximal base by the engagement of the tab and the pocket.

\* \* \* \* \*